United States Patent
Choi et al.

(10) Patent No.: US 11,066,382 B2
(45) Date of Patent: Jul. 20, 2021

(54) ORGANIC COMPOUND AND ORGANIC ELECTROLUMINESCENT DEVICE COMPRISING SAME

(71) Applicant: SOLUS ADVANCED MATERIALS CO., LTD., Iksan-si (KR)

(72) Inventors: Tae Jin Choi, Yongin-si (KR); Jae Hoon Lee, Yongin-si (KR); Young Bae Kim, Yongin-si (KR)

(73) Assignee: SOLUS ADVANCED MATERIALS CO., LTD., Iksan-si (KR)

( * ) Notice: Subject to any disclaimer, the term of this patent is extended or adjusted under 35 U.S.C. 154(b) by 330 days.

(21) Appl. No.: 15/781,862

(22) PCT Filed: Dec. 23, 2016

(86) PCT No.: PCT/KR2016/015200
§ 371 (c)(1),
(2) Date: Jun. 6, 2018

(87) PCT Pub. No.: WO2017/111544
PCT Pub. Date: Jun. 29, 2017

(65) Prior Publication Data
US 2018/0346439 A1 Dec. 6, 2018

(30) Foreign Application Priority Data

Dec. 24, 2015 (KR) .................. 10-2015-0185976

(51) Int. Cl.
| | | |
|---|---|---|
| *C07D 319/24* | (2006.01) |
| *C07D 319/14* | (2006.01) |
| *C07D 333/76* | (2006.01) |
| *C07D 209/82* | (2006.01) |
| *C07D 307/91* | (2006.01) |
| *C07D 405/14* | (2006.01) |
| *H05B 33/20* | (2006.01) |
| *C07D 405/04* | (2006.01) |
| *C07D 405/10* | (2006.01) |
| *C07D 407/04* | (2006.01) |
| *C07D 407/10* | (2006.01) |
| *C07D 409/04* | (2006.01) |
| *C07D 409/10* | (2006.01) |
| *C07D 413/10* | (2006.01) |
| *C07D 417/10* | (2006.01) |
| *H01L 51/00* | (2006.01) |
| *H01L 51/50* | (2006.01) |

(52) U.S. Cl.
CPC ......... *C07D 319/24* (2013.01); *C07D 209/82* (2013.01); *C07D 307/91* (2013.01); *C07D 319/14* (2013.01); *C07D 333/76* (2013.01); *C07D 405/04* (2013.01); *C07D 405/10* (2013.01); *C07D 405/14* (2013.01); *C07D 407/04* (2013.01); *C07D 407/10* (2013.01); *C07D 409/04* (2013.01); *C07D 409/10* (2013.01); *C07D 413/10* (2013.01); *C07D 417/10* (2013.01); *H01L 51/0069* (2013.01); *H01L 51/0073* (2013.01); *H05B 33/20* (2013.01); *H01L 51/0061* (2013.01); *H01L 51/0067* (2013.01); *H01L 51/0072* (2013.01); *H01L 51/0074* (2013.01); *H01L 51/5012* (2013.01); *H01L 51/5056* (2013.01); *H01L 51/5072* (2013.01)

(58) Field of Classification Search
None
See application file for complete search history.

(56) References Cited

U.S. PATENT DOCUMENTS

2015/0137111 A1* 5/2015 Ryu .................. H01L 51/0069
257/40

FOREIGN PATENT DOCUMENTS

| KR | 10-2013-0078439 A | 7/2013 |
| KR | 10-2014-0042554 A | 4/2014 |
| KR | 10-2014-0054132 A | 5/2014 |
| KR | 10-2015-0117130 A | 10/2015 |
| KR | 10-2015-0128583 A | 11/2015 |
| WO | 2014/010910 A1 | 1/2014 |
| WO | 2015/012618 A1 | 1/2015 |
| WO | 2015/174682 A1 | 11/2015 |

OTHER PUBLICATIONS

Chemical Abstract Compound RN 1423138-63-9, STN Express, Entered STN: Mar. 13, 2013, 1 Page. (Year: 2013).*
STN structure search for U.S. Appl. No. 15/781,862 conducted by the Examiner. All Pages, 2020. (Year: 2020).*
Chemical Abstract Compound, STN Express, Entered STN:, RN 1423138-63-9, Mar. 13, 2013, 1 page.
CAS Registry No. 1423138-63-9, STN, Jun. 6, 2017, 3 pages.
International Search Report for PCT/KR2016/015200 dated Apr. 17, 2017 [PCT/ISA/210].

* cited by examiner

*Primary Examiner* — Daniel P Malley, Jr.
(74) *Attorney, Agent, or Firm* — Sughrue Mion, PLLC

(57) ABSTRACT

The present disclosure relates to a novel compound, and an organic electroluminescent device including the same, and by using the compound according to the present disclosure in an organic material layer, preferably a light emitting layer or an auxiliary light emitting layer, of an organic electroluminescent device, light emission efficiency, a driving voltage, a lifetime and the like of the organic electroluminescent device may be enhanced.

11 Claims, No Drawings

ORGANIC COMPOUND AND ORGANIC ELECTROLUMINESCENT DEVICE COMPRISING SAME

CROSS REFERENCE TO RELATED APPLICATIONS

This application is a National Stage of International Application No. PCT/KR2016/015200, filed on Dec. 23, 2016, which claims priority from Korean Patent Application No. 10-2015-0185976, filed on Dec. 24, 2015.

TECHNICAL FIELD

The present disclosure relates to a novel organic compound capable of being used as a material for an organic electroluminescent device, and an organic electroluminescent device including the same.

BACKGROUND ART

With the observation of organic thin film light emission made by Bernanose in 1950s as a start, studies on organic electroluminescent (EL) devices have been continued leading to blue electroluminescence using a single anthracene crystal in 1965, and in 1987, an organic electroluminescent device having a laminated structure divided into functional layers of a hole layer and a light emitting layer has been proposed by Tang. After that, in order to manufacture organic electroluminescent devices with high efficiency and long lifetime, development has been made in the form of introducing each characteristic organic material layer into the device, which leads to the development of specialized materials used therein.

When a voltage is applied between the two electrodes in an organic electroluminescent device, holes and electrons are injected to an organic material layer from the anode and the cathode, respectively. When the injected holes and electrons meet, excitons are formed, and light emits when these excitons fall back to the ground state. Herein, materials used as the organic material layer may be divided into light emitting materials, hole injection materials, hole transport materials, electron transport materials, electron injection materials and the like depending on the function.

The light emitting material may be divided into, depending on the light emitting color, blue, green and red light emitting materials, and yellow and orange light emitting materials for obtaining better natural colors. In addition, in order to increase color purity and increase light emission efficiency through energy transfer, host/dopant series may be used as the light emitting material.

The dopant material may be divided into fluorescent dopants using organic materials and phosphorescent dopants using metal complex compounds including heavy atoms such as Ir or Pt. Herein, development of phosphorescent materials may enhance light emission efficiency up to 4 times compared to fluorescence theoretically, and therefore, studies on phosphorescent host materials have been widely progressed as well as on phosphorescent dopants.

So far, NPB, BCP, Alq$_3$ and the like have been widely known as materials of a hole injection layer, a hole transport layer, a hole blocking layer and an electron transport layer, and anthracene derivatives have been reported as a material of a light emitting layer. Particularly, among light emitting layer materials, metal complex compounds including Ir such as Firpic, Ir(ppy)$_3$ or (acac)Ir(btp)$_2$ having advantages in terms of efficiency enhancement have been used as blue, green and red phosphorescent dopant materials, and 4,4-dicarbazolylbiphenyl (CBP) has been used as a phosphorescent host material.

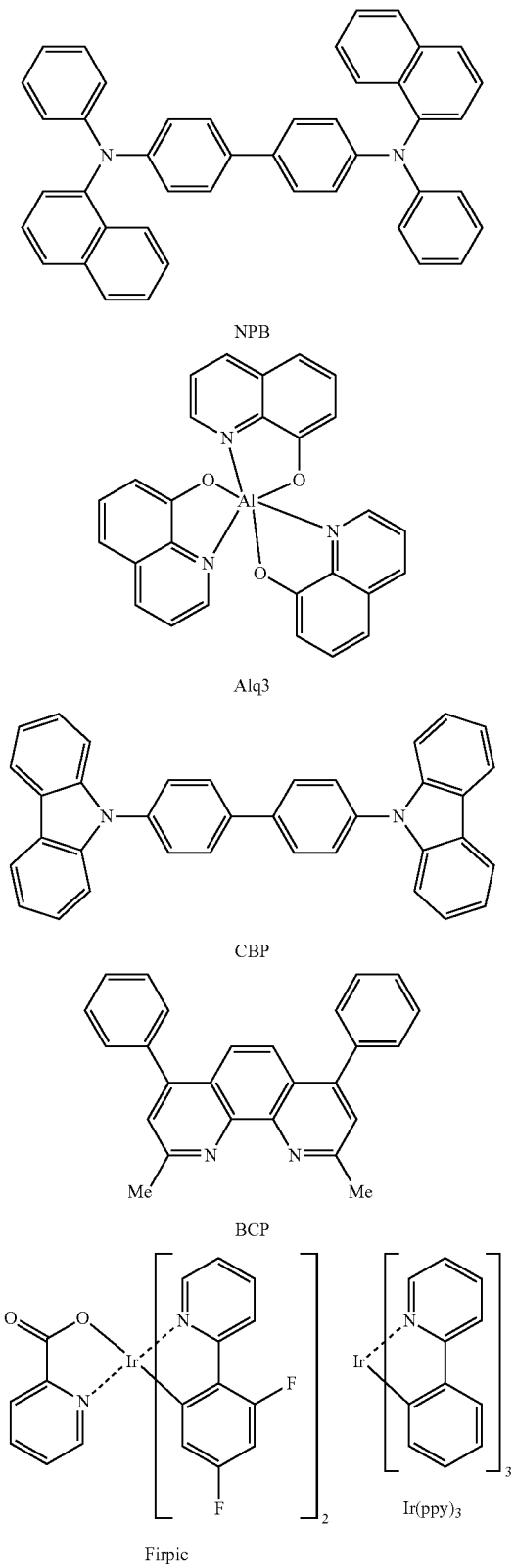

NPB

Alq3

CBP

BCP

Firpic

Ir(ppy)$_3$

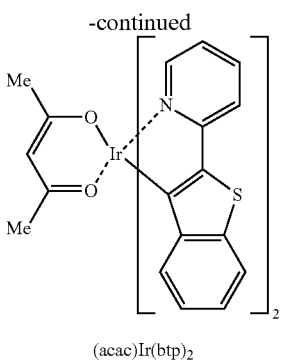

(acac)Ir(btp)₂

However, although being advantageous in terms of light emission properties, existing organic material layer materials have a low glass transition temperature and have very unfavorable thermal stability, and therefore, competency has not been obtained in terms of an organic electroluminescent device life. Accordingly, development of organic material layer materials having superior performance has been required.

DISCLOSURE

Technical Problem

The present disclosure is directed to providing a novel compound capable of enhancing efficiency, lifetime, stability and the like of an organic electroluminescent device, and an organic electroluminescent device using the compound.

Technical Solution

In view of the above, one embodiment of the present disclosure provides a compound represented by the following Chemical Formula 1:

[Chemical Formula 1]

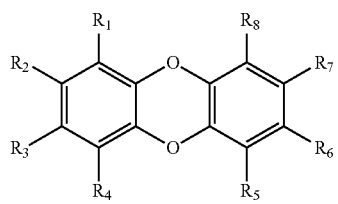

in Chemical Formula 1, at least one of $R_1$ and $R_2$, $R_2$ and $R_3$, $R_3$ and $R_4$, $R_5$ and $R_6$, $R_6$ and $R_7$, and $R_7$ and $R_8$ is fused with a ring represented by the following Chemical Formula 2 to form a fused ring;

$R_1$ to $R_8$ that do not form a fused ring with the ring represented by the following Chemical Formula 2 may be each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylamine group, or may bond to adjacent groups to form a fused ring;

the $R_1$ to $R_8$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, and when substituted with a plurality of substituents, these may be the same as or different from each other;

[Chemical Formula 2]

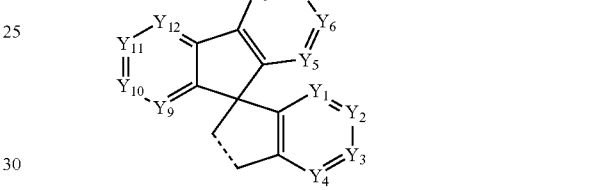

in Chemical Formula 2, a broken line means a part that is fused;

$Y_1$ to $Y_{12}$ are each independently N or C($R_9$);

$R_9$ may be selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylamine group, or may bond to adjacent groups to form a fused ring, and when $R_9$ is present in plural numbers, these are the same as or different from each other; and the $R_9$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, and when substituted with a plurality of substituents, these may be the same as or different from each other.

Another embodiment of the present disclosure provides an organic electroluminescent device including an anode, a cathode and one or more organic material layers provided between the anode and the cathode, wherein at least one of the one or more organic material layers includes the compound of Chemical Formula 1.

In the present disclosure, the "adjacent group" means substituents substituting neighboring carbons like $R_1$ and $R_2$, $R_2$ and $R_3$, $R_3$ and $R_4$, $R_5$ and $R_6$, $R_6$ and $R_7$, $R_7$ and $R_8$ or the like.

In the present disclosure, the "alkyl" is a monovalent substituent derived from linear or branched saturated hydrocarbon having 1 to 40 carbon atoms. Examples thereof may include methyl, ethyl, propyl, isobutyl, sec-butyl, pentyl, iso-amyl, hexyl and the like, but are not limited thereto.

In the present disclosure, the "alkenyl" is a monovalent substituent derived from linear or branched unsaturated hydrocarbon having 2 to 40 carbon atoms and having one or more carbon-carbon double bonds. Examples thereof may include vinyl, allyl, isopropenyl, 2-butenyl and the like, but are not limited thereto.

In the present disclosure, the "alkynyl" is a monovalent substituent derived from linear or branched unsaturated hydrocarbon having 2 to 40 carbon atoms and having one or more carbon-carbon triple bonds. Examples thereof may include ethynyl, 2-propynyl and the like, but are not limited thereto.

In the present disclosure, the "aryl" means a monovalent substituent derived from aromatic hydrocarbon having 6 to 60 carbon atoms and having a single ring or a combination of two or more rings. In addition, a monovalent substituent having two or more rings being fused with each other, including only carbon (for example, the number of carbon atoms may be from 8 to 60) as a ring-forming atom, and with the whole molecule having non-aromacity may also be included. Examples of such aryl may include phenyl, naphthyl, phenanthryl, anthryl, fluorenyl and the like, but are not limited thereto.

In the present disclosure, the "heteroaryl" means a monovalent substituent derived from monoheterocyclic or polyheterocyclic aromatic hydrocarbon having 5 to 60 nuclear atoms. Herein, one or more carbons, preferably, 1 to 3 carbons in the ring are substituted with heteroatoms selected from among N, O, P, S and Se. In addition, a monovalent group having two or more rings being simply attached (pendant) or fused, including heteroatoms selected from among N, O, P, S and Se other than carbon as a ring-forming atom, and with the whole molecule having non-aromacity is construed as being included as well. Examples of such heteroaryl may include 6-membered monocyclic rings such as pyridyl, pyrazinyl, pyrimidinyl, pyridazinyl or triazinyl; polycyclic rings such as phenoxathienyl, indolizinyl, indolyl, purinyl, quinolyl, benzothiazole or carbazolyl; 2-furanyl, N-imidazolyl, 2-isoxazolyl, 2-pyridinyl, 2-pyrimidinyl and the like, but are not limited thereto.

In the present disclosure, the "aryloxy" is a monovalent substituent represented by RO—, and R means aryl having 5 to 60 carbon atoms. Examples of such aryloxy may include phenyloxy, naphthyloxy, diphenyloxy and the like, but are not limited thereto.

In the present disclosure, the "alkyloxy" is a monovalent substituent represented by R'O—, and R' means alkyl having 1 to 40 carbon atoms and is construed as including a linear, branched or cyclic structure. Examples of such alkyloxy may include methoxy, ethoxy, n-propoxy, 1-propoxy, t-butoxy, n-butoxy, pentoxy and the like, but are not limited thereto.

In the present disclosure, the "arylamine" means amine substituted with aryl having 6 to 60 carbon atoms.

In the present disclosure, the "cycloalkyl" means a monovalent substituent derived from monocyclic or polycyclic non-aromatic hydrocarbon having 3 to 40 carbon atoms. Examples of such cycloalkyl may include cyclopropyl, cyclopentyl, cyclohexyl, norbomyl, adamantine and the like, but are not limited thereto.

In the present disclosure, the "heterocycloalkyl" means a monovalent substituent derived from non-aromatic hydrocarbon having 3 to 40 nuclear atoms, and one or more carbons, preferably, 1 to 3 carbons in the ring are substituted with heteroatoms such as N, O, S or Se. Examples of such heterocycloalkyl may include morpholine, piperazine and the like, but are not limited thereto.

In the present disclosure, the "alkylsilyl" means silyl substituted with alkyl having 1 to 40 carbon atoms, and the "arylsilyl" means silyl substituted with aryl having 5 to 60 carbon atoms.

In the present disclosure, the "fused ring" means a fused aliphatic ring, a fused aromatic ring, a fused heteroaliphatic ring, a fused heteroaromatic ring or a combined form thereof.

Advantageous Effects

A compound of the present disclosure has excellent thermal stability, carrier transport ability, light emitting ability and the like, and therefore, is useful as a material of an organic material layer of an organic electroluminescent device.

In addition, an organic electroluminescent device including a compound of the present disclosure in an organic material layer exhibits greatly enhanced light emitting performance, driving voltage, lifetime, efficiency and the like, and can be effectively used in a full color display panel and the like.

MODE FOR DISCLOSURE

The present disclosure provides a compound represented by the following Chemical Formula 1:

[Chemical Formula 1]

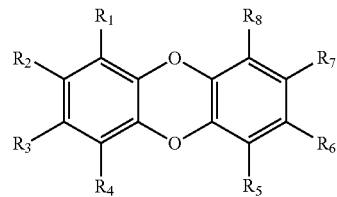

in Chemical Formula 1, at least one of $R_1$ and $R_2$, $R_2$ and $R_3$, $R_3$ and $R_4$, $R_5$ and $R_6$, $R_6$ and $R_7$, and $R_7$ and $R_8$ is fused with a ring represented by the following Chemical Formula 2 to form a fused ring;

$R_1$ to $R_8$ that do not form a fused ring with the ring represented by the following Chemical Formula 2 may be each independently selected from the group consisting of hydrogen, deuterium, halogen, a cyano group, a nitro group, a $C_1{\sim}C_{40}$ alkyl group, a $C_2{\sim}C_{40}$ alkenyl group, a $C_2{\sim}C_{40}$ alkynyl group, a $C_3{\sim}C_{40}$ cycloalkyl group, a heterocycloalkyl group having 3 to 40 nuclear atoms, a $C_6{\sim}C_{60}$ aryl group, a heteroaryl group having 5 to 60 nuclear atoms, a $C_1{\sim}C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylamine group, or may bond to adjacent groups to form a fused ring;

the $R_1$ to $R_8$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, and when substituted with a plurality of substituents, these may be the same as or different from each other;

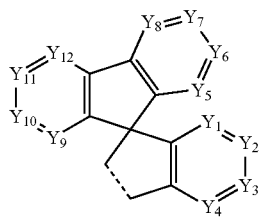

[Chemical Formula 2]

in Chemical Formula 2,
a broken line means a part that is fused;
$Y_1$ to $Y_{12}$ are each independently N or $C(R_9)$;
$R_9$ may be selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylamine group, or may bond to adjacent groups to form a fused ring, and when $R_9$ is present in plural numbers, these are the same as or different from each other; and the $R_9$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, and when substituted with a plurality of substituents, these may be the same as or different from each other.

Hereinafter, the present disclosure will be described in detail.

1. Novel Organic Compound

The novel compound of the present disclosure has a structure in which a basic skeleton is formed by fusing a spirofluorene moiety to dibenzo[b,e][1,4]dioxine, and various substituents bond or are fused to such a basic skeleton, and is represented by the following Chemical Formula 1:

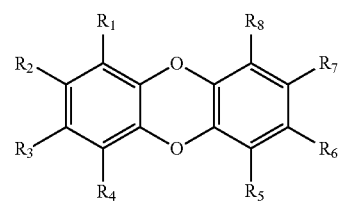

[Chemical Formula 1]

in Chemical Formula 1,
at least one of $R_1$ and $R_2$, $R_2$ and $R_3$, $R_3$ and $R_4$, $R_5$ and $R_6$, $R_6$ and $R_7$, and $R_7$ and $R_8$ is each independently fused with a ring represented by the following Chemical Formula 2 to form a fused ring, and when at least two of $R_1$ and $R_2$, $R_2$ and $R_3$, $R_3$ and $R_4$, $R_5$ and $R_6$, $R_6$ and $R_7$, and $R_7$ and $R_8$ are fused with the ring represented by the following Chemical Formula 2 to form a fused ring, the fused rings are the same as or different from each other;

$R_1$ to $R_8$ that do not form a fused ring with the ring represented by the following Chemical Formula 2 may be each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylamine group, or may bond to adjacent groups (for example, any one substituent among other adjacent $R_1$ to $R_8$, or the like) to form a fused ring;

the $R_1$ to $R_8$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, and when substituted with a plurality of substituents, these may be the same as or different from each other;

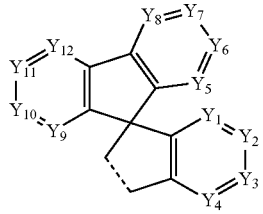

[Chemical Formula 2]

in Chemical Formula 2,
a broken line means a part that is fused;
$Y_1$ to $Y_{12}$ are each independently N or $C(R_9)$;
$R_9$ may be selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylamine group, or may bond to adjacent groups (for example, other adjacent $R_9$, or the like) to form a fused ring, and when $R_9$ is present in plural numbers, these are the same as or different from each other; and
the $R_9$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, and when substituted with a plurality of substituents, these may be the same as or different from each other.

A phosphorescent light emitting layer among organic material layers included in an organic electroluminescent device generally includes a host and a dopant in order to increase color purity and increase light emission efficiency. Herein, the host needs to have a higher triplet energy gap than the dopant. In other words, in order to effectively provide phosphorescent light emission from a dopant, energy of a lowest excited state of a host needs to be higher than energy in a lowest emission state of the dopant. In the compound represented by Chemical Formula 1 of the present disclosure, a dibenzo[b,e][1,4]dioxine part has a wide singlet energy level and a high triplet energy level. By introducing specific substituents to a spirofluorene moiety and the like fused to such dibenzo[b,e][1,4]dioxine, the compound of Chemical Formula 1 is able to have a higher energy level than a dopant when used as a host of a light emitting layer.

In addition, the compound represented by Chemical Formula 1 has high triplet energy as described above, and therefore, is capable of preventing excitons produced in the light emitting layer from being diffused (moved) to an adjacent electron transport layer or hole transport layer.

Accordingly, when forming an organic material layer (hereinafter, referred to as 'an auxiliary light emitting layer') between the hole transport layer and the light emitting layer, or forming an organic material layer (hereinafter, referred to as 'an auxiliary electron transport layer') between the light emitting layer and the electron transport layer using the compound of Chemical Formula 1, diffusion of excitons may be prevented by the compound, and therefore, unlike existing organic electroluminescent devices that do not include the auxiliary light emitting layer or the auxiliary electron transport layer, the number of excitons actually contributing to light emission in the light emitting layer increases, which may improve light emission efficiency of a device.

In addition, the compound represented by Chemical Formula 1 may have HOMO and LUMO energy levels controlled depending on the substituent introduced to the basic skeleton, and therefore, may have a wide band gap and high carrier transportability.

Moreover, the compound of the present disclosure may be useful as a hole transport layer material when an electron donating group (EDG) having a high electron providing property bonds to the basic skeleton due to high hole transport capability of the oxygen atom in the dibenzo[b,e][1,4]dioxine. In addition, when an electron withdrawing group (EWG) having a high electron absorbing property bonds to the basic skeleton, the whole molecule has a bipolar property increasing binding strength between holes and electrons.

According to one preferred embodiment of the present disclosure, the compound represented by Chemical Formula 1 may be a compound represented by any one of the following Chemical Formulae 3 to 5, but is not limited thereto:

[Chemical Formula 3]

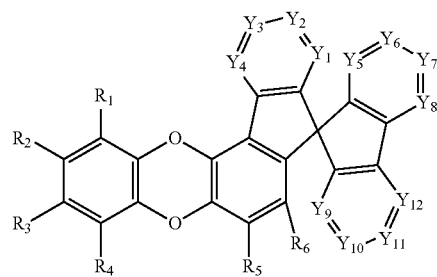

[Chemical Formula 4]

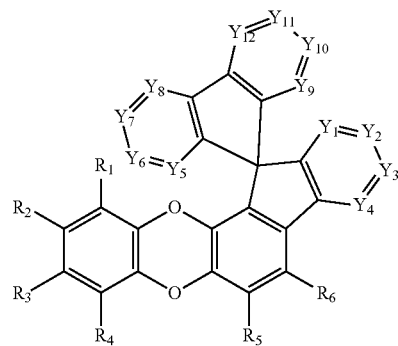

-continued

[Chemical Formula 5]

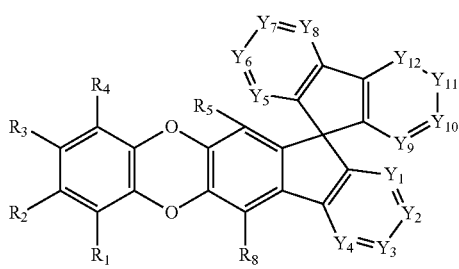

in Chemical Formulae 3 to 5, $Y_1$ to $Y_{12}$ and $R_1$ to $R_8$ each have the same definition as in Chemical Formula 1.

According to one preferred embodiment of the present disclosure, in Chemical Formulae 3 to 5, at least one of $Y_1$ to $Y_4$ is $C(R_9)$, and when $R_9$ is present in plural numbers, these are the same as or different from each other, and $R_9$ has the same definition as in Chemical Formula 2.

According to one preferred embodiment of the present disclosure, in Chemical Formulae 3 to 5, $Y_1$ to $Y_{12}$ are all $C(R_9)$, and herein, a plurality of $R_9$s are the same as or different from each other, and $R_9$ has the same definition as in Chemical Formula 2.

According to one preferred embodiment of the present disclosure, $R_9$ is preferably a substituent represented by the following Chemical Formula 6 in terms of light emission efficiency, but is not limited thereto:

[Chemical Formula 6]

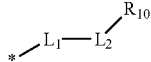

In Chemical Formula 6,

* means a part where a bond is formed;

$L_1$ and $L_2$ are each independently selected from the group consisting of a direct bond, a $C_6$~$C_{18}$ arylene group and a heteroarylene group having 5 to 18 nuclear atoms;

$R_{10}$ may be selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylamine group, or may bond to adjacent groups (for example, $L_1$ or $L_2$, other neighboring $R_9$, $R_{10}$, or the like) to form a fused ring; and the $L_1$ and $L_2$ arylene group and heteroarylene group, and the $R_{10}$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, and when substituted with a plurality of substituents, these may be the same as or different from each other.

According to one preferred embodiment of the present disclosure, $R_{10}$ may be selected from the group consisting of hydrogen, deuterium (D), a $C_6$~$C_{60}$ aryl group, a heteroaryl group having 5 to 60 nuclear atoms and a $C_6$~$C_{60}$ arylamine group.

By introducing various substituents, particularly an aryl group and/or a heteroaryl group, to the basic skeleton, the compound represented by Chemical Formula 1 of the present disclosure has a significantly increased molecular weight, and thereby has an enhanced glass transition temperature, and may resultingly have higher thermal stability than existing organic material layer materials (for example, CBP). In addition, the compound represented by Chemical Formula 1 is effective in suppressing crystallization of an organic material layer.

As described above, when using the compound represented by Chemical Formula 1 of the present disclosure as an organic material layer material, preferably a light emitting layer material (blue, green and/or red phosphorescent host material), an electron transport layer/injection layer material, a hole transport layer/injection layer material, an auxiliary light emitting layer material or a lifetime improving layer material, of an organic electroluminescent device, performance and lifetime properties of the organic electroluminescent device may be greatly enhanced. Such an organic electroluminescent device may ultimately maximize performance of a full-color organic light emitting panel.

According to one preferred embodiment of the present disclosure, $L_1$ and $L_2$ are preferably each independently a linker represented by any one of the following Chemical Formulae 7 to 11 in terms of light emission efficiency, but is not limited thereto:

[Chemical Formula 7]

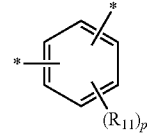

[Chemical Formula 8]

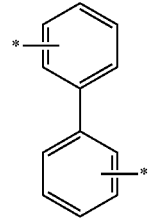

[Chemical Formula 9]

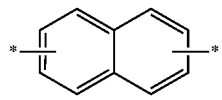

[Chemical Formula 10]

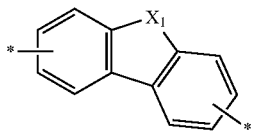

[Chemical Formula 11]

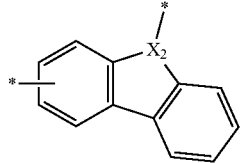

in Chemical Formulae 7 to 11,

* means a part where a bond is formed;

$X_1$ is O, S, $N(R_{12})$ or $C(R_{13})(R_{14})$;

$X_2$ is N or $C(R_{15})$;

p is an integer of 0 to 4;

$R_{11}$ may be selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylamine group, or may bond to adjacent groups (for example, $L_1$ or $L_2$, or other neighboring $R_9$, $R_{10}$, $R_{11}$ or the like) to form a fused ring, and when $R_{11}$ is present in plural numbers, these are the same as or different from each other;

$R_{12}$ to $R_{15}$ may be each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_3$~$C_{40}$ cycloalkyl group, a heterocycloalkyl group having 3 to 40 nuclear atoms, a $C_6$~$C_{60}$ arylamine group, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, or may bond to adjacent groups (for example, $L_1$ or $L_2$, or other neighboring $R_9$, $R_{10}$, $R_{11}$ or the like) to form a fused ring; and the $R_{11}$ to $R_{15}$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, and when substituted with a plurality of substituents, these may be the same as or different from each other.

According to one preferred embodiment of the present disclosure, $R_{10}$ is preferably a substituent represented by any one of the following Chemical Formulae 12 to 14 in terms of light emission efficiency, but is not limited thereto:

[Chemical Formula 12]

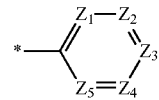

[Chemical Formula 13]

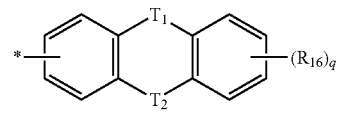

[Chemical Formula 14]

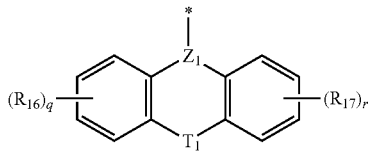

in Chemical Formulae 12 to 14,

* means a part where a bond is formed;

$Z_1$ to $Z_5$ are each independently N or $C(R_{18})$;

$T_1$ and $T_2$ are each independently selected from the group consisting of a direct bond, $C(R_{19})(R_{20})$, $N(R_{21})$, O and S, however, $T_1$ and $T_2$ are not both a direct bond;

q and r are each independently an integer of 0 to 4;

$R_{16}$ and $R_{17}$ may be each independently selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_3$~$C_{40}$ cycloalkyl group, a heterocycloalkyl group having 3 to 40 nuclear atoms, a $C_6$~$C_{60}$ arylamine group, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, or may bond to adjacent groups to form a fused ring, and when each of $R_{16}$ and $R_{17}$ is present in plural numbers, these are the same as or different from each other;

$R_{18}$ to $R_{21}$ may be each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_3$~$C_{40}$ cycloalkyl group, a heterocycloalkyl group having 3 to 40 nuclear atoms, a $C_6$~$C_{60}$ arylamine group, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, or may bond to adjacent groups to form a fused ring, and when each of $R_{18}$ to $R_{21}$ is present in plural numbers, these are the same as or different from each other; and the $R_{16}$ to $R_{21}$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1\sim C_{40}$ alkyl group, a $C_2\sim C_{40}$ alkenyl group, a $C_2\sim C_{40}$ alkynyl group, a $C_6\sim C_{60}$ aryl group, a heteroaryl group having 5 to 60 nuclear atoms, a $C_6\sim C_{60}$ aryloxy group, a $C_1\sim C_{40}$ alkyloxy group, a $C_6\sim C_{60}$ arylamine group, a $C_3\sim C_{40}$ cycloalkyl group, a heterocycloalkyl group having 3 to 40 nuclear atoms, a $C_1\sim C_{40}$ alkylsilyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphynyl group and a $C_6\sim C_{60}$ arylsilyl group, and when substituted with a plurality of substituents, these may be the same as or different from each other.

According to one preferred embodiment of the present disclosure, the substituents represented by Chemical Formulae 12 to 14 may be a substituent represented by any one of the following Chemical Formulae A-1 to A-24, but are not limited thereto:

A-1

A-2

A-3

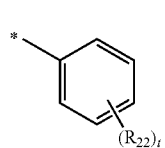

A-4

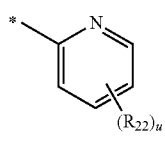

A-5

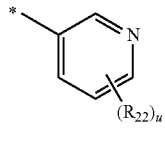

A-6

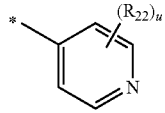

A-7

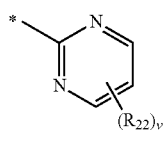

A-8

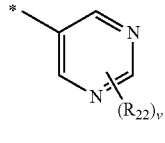

-continued

A-9

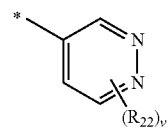

A-10

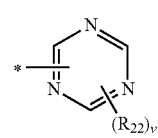

A-11

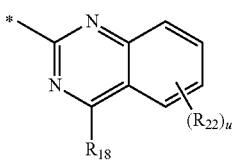

A-12

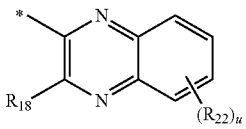

A-13

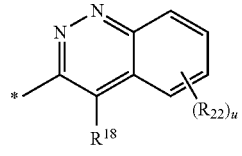

A-14

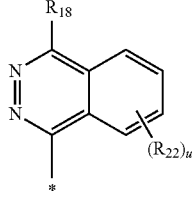

A-15

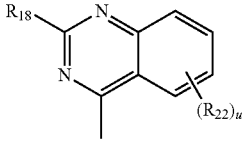

A-16

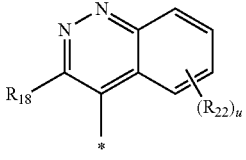

A-17

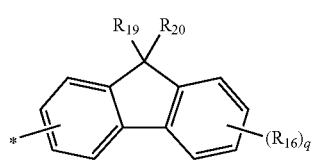

in Chemical Formulae A-1 to A-24,
* means a part where a bond is formed;
t is an integer of 0 to 5,
u is an integer of 0 to 4;
v is an integer of 0 to 3;
w is an integer of 0 to 2;
$R_{22}$ may be selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_3$~$C_{40}$ cycloalkyl group, a heterocycloalkyl group having 3 to 40 nuclear atoms, a $C_6$~$C_{60}$ arylamine group, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, or may bond to adjacent groups (for example, any one of $L_1$ or $L_2$, or other adjacent $R_{22}$, $R_{16}$ to $R_{21}$ or the like) to form a fused ring, and when $R_{22}$ is present in plural numbers, these are the same as or different from each other;

the $R_{22}$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, and when substituted with a plurality of substituents, these may be the same as or different from each other; and $R_{16}$ to $R_{21}$, p and q have the same definitions as in Chemical Formulae 12 to 14.

According to one preferred embodiment of the present disclosure, $R_{10}$ is preferably a substituent represented by the following Chemical Formula 15 in terms of increasing light emission efficiency, but is not limited thereto:

[Chemical Formula 15]

$$*-N\begin{subarray}{l}R_{23}\\R_{24}\end{subarray}$$

in Chemical Formula 15,
* means a part where a bond is formed;
$R_{23}$ and $R_{24}$ may be each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_3$~$C_{40}$ cycloalkyl group, a heterocycloalkyl group having 3 to 40 nuclear atoms, a $C_6$~$C_{60}$ arylamine group, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, or may bond to adjacent groups (for example, $R_{23}$ and $R_{24}$ bond to each other) to form a fused ring; and the $R_{23}$ and $R_{24}$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, and when substituted with a plurality of substituents, these may be the same as or different from each other.

According to one preferred embodiment of the present disclosure, $R_{23}$ and $R_{24}$ may be each independently selected from the group consisting of hydrogen, a $C_1$~$C_{40}$ alkyl group, a $C_6$~$C_{60}$ aryl group, a heteroaryl group having 5 to 60 nuclear atoms and a $C_6$~$C_{60}$ arylamine group.

According to one preferred embodiment of the present disclosure, $R_{23}$ and $R_{24}$ may be each independently selected from the group consisting of hydrogen, a phenyl group, a biphenyl group, a terphenyl group, a naphthylenyl group, a fluorenyl group, and a substituent represented by the following Chemical Formula 16, but is not limited thereto:

[Chemical Formula 16]

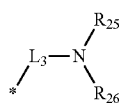

in Chemical Formula 16,

* means a part where a bond is formed;

$L_3$ is each independently selected from the group consisting of a direct bond, a $C_6$~$C_{18}$ arylene group and a heteroarylene group having 5 to 18 nuclear atoms;

$R_{25}$ and $R_{26}$ may be each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylamine group, or may bond to adjacent groups (for example, $L_3$ or other neighboring $R_{23}$, $R_{24}$ or the like, or $R_{25}$ and $R_{26}$ bond to each other) to form a fused ring; and the $L_3$ arylene group and heteroarylene group, and the $R_{25}$ and $R_{26}$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, and when substituted with a plurality of substituents, these may be the same as or different from each other.

The compound represented by Chemical Formula 1 of the present disclosure may be represented by the following compounds, but is not limited thereto:

Cpd 1

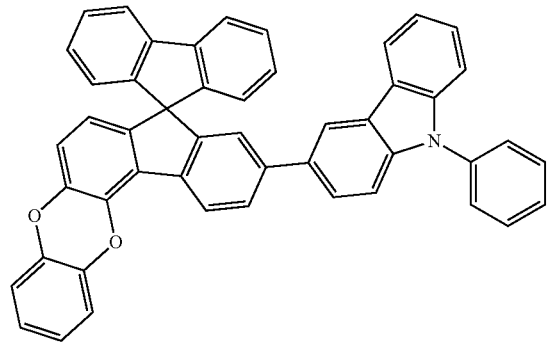

Cpd 2

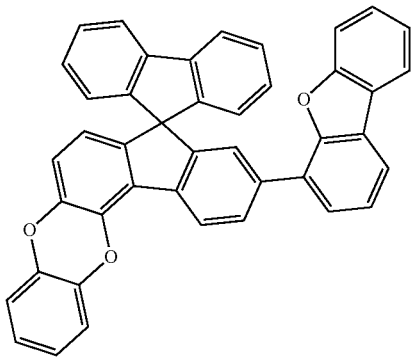

Cpd 3

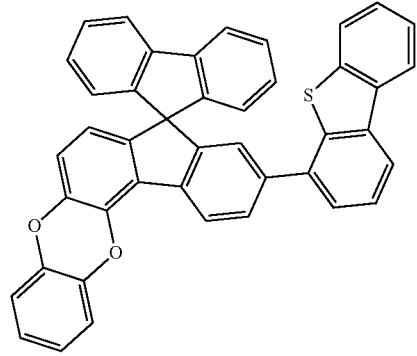

Cpd 4

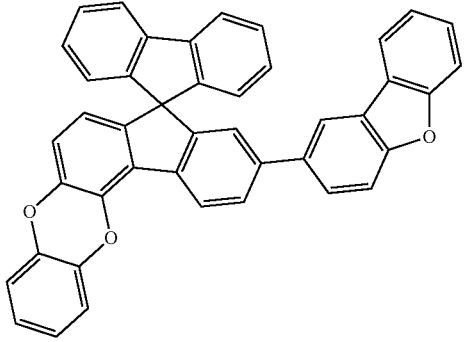

-continued
Cpd 5
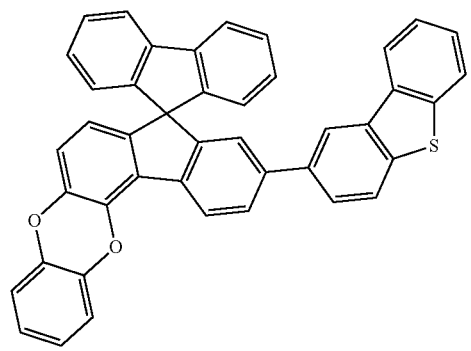
Cpd 6
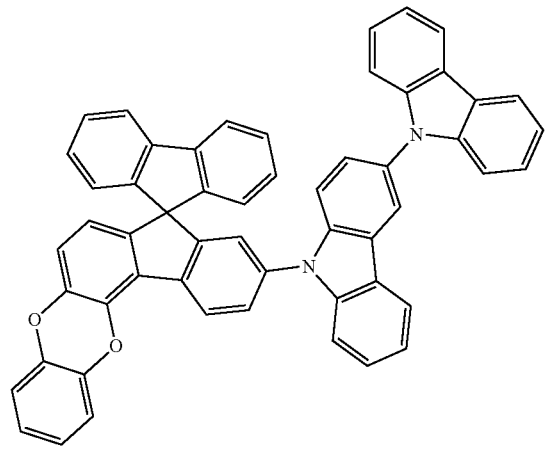
Cpd 7
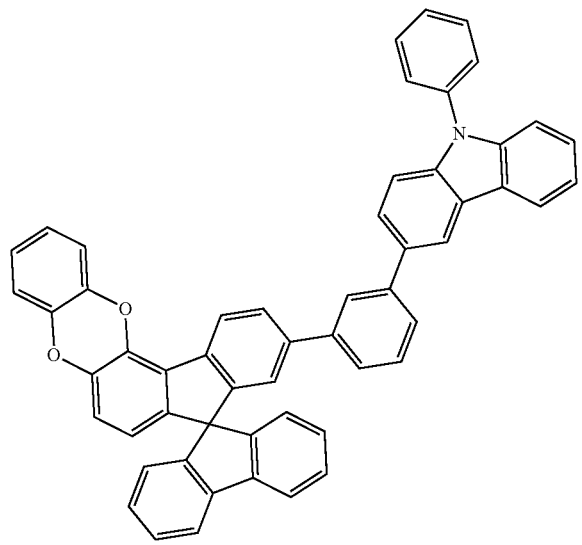
Cpd 8
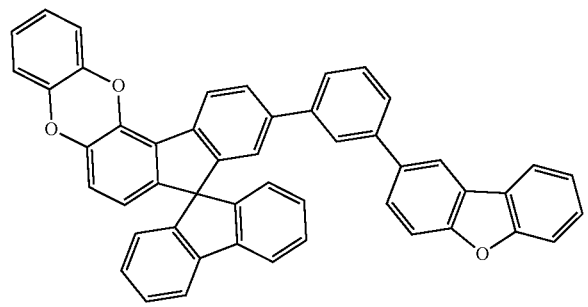
Cpd 9
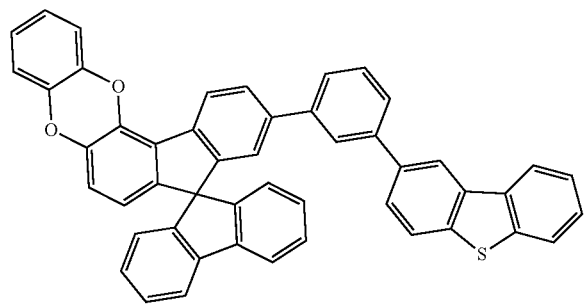
Cpd 10
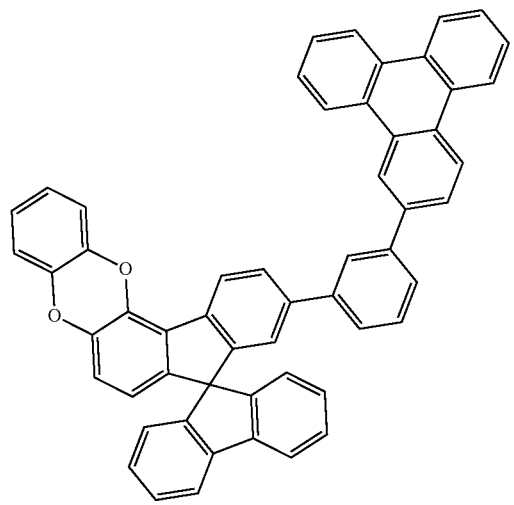

-continued
Cpd 11
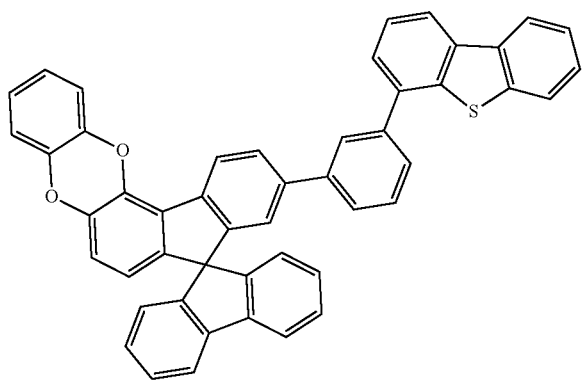
Cpd 12
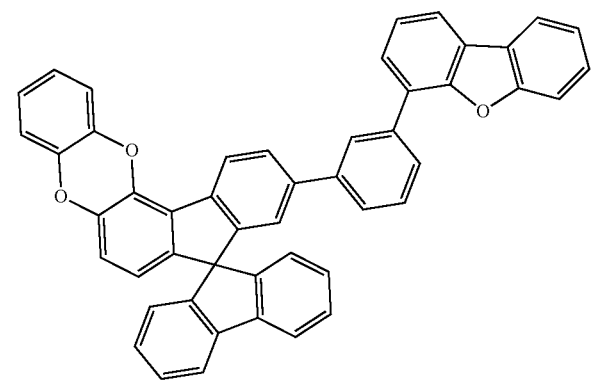
Cpd 13
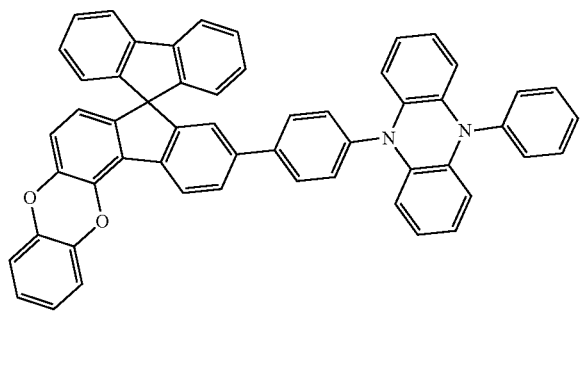
Cpd 14
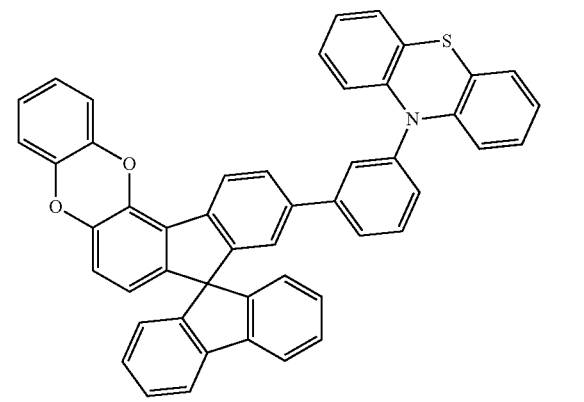
Cpd 15
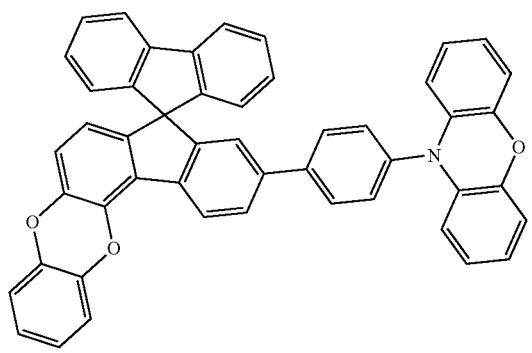
Cpd 16
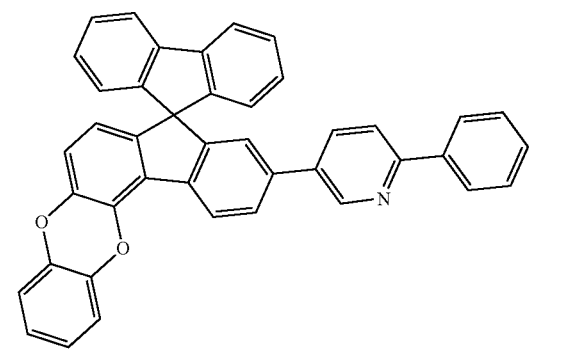
Cpd 17
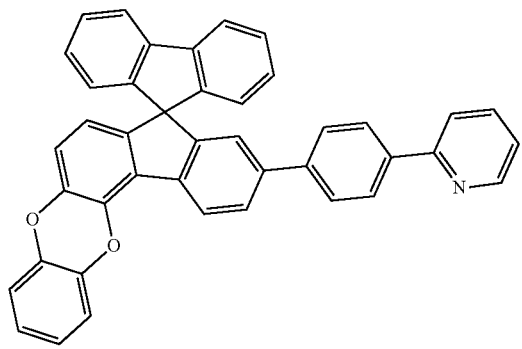
Cpd 18
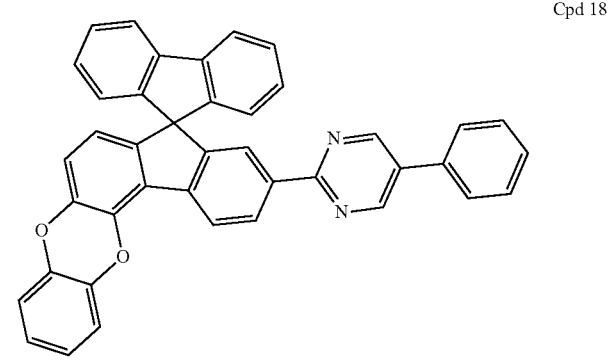

-continued
Cpd 19
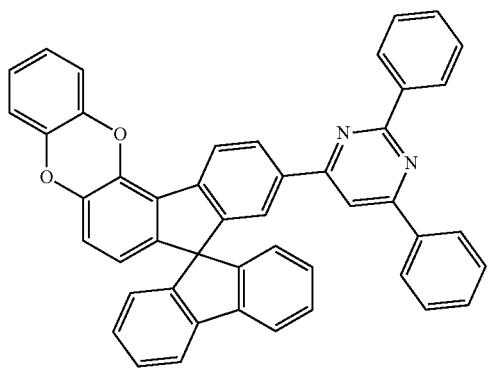
Cpd 20
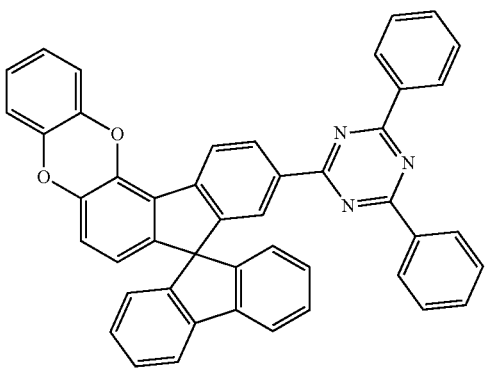
Cpd 21
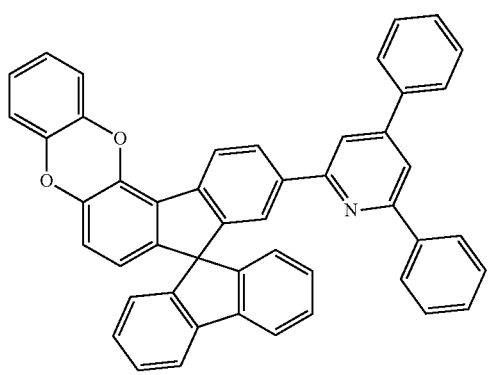
Cpd 22
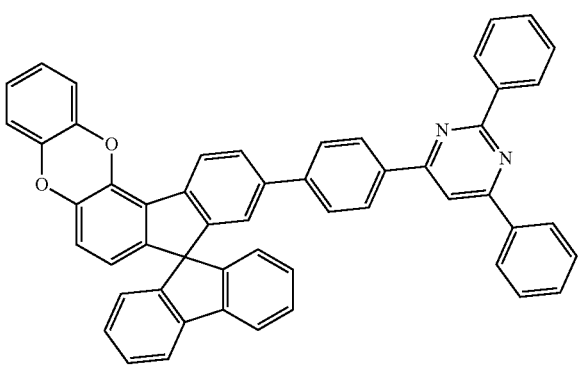
Cpd 23
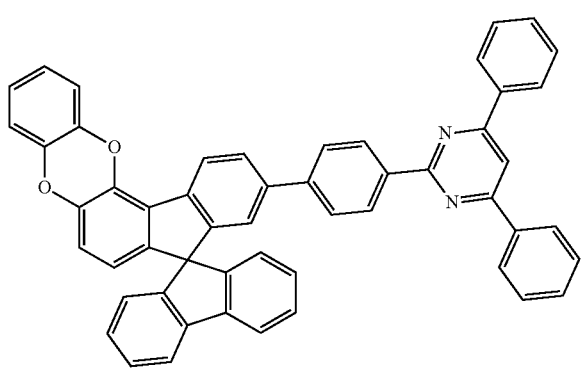
Cpd 24
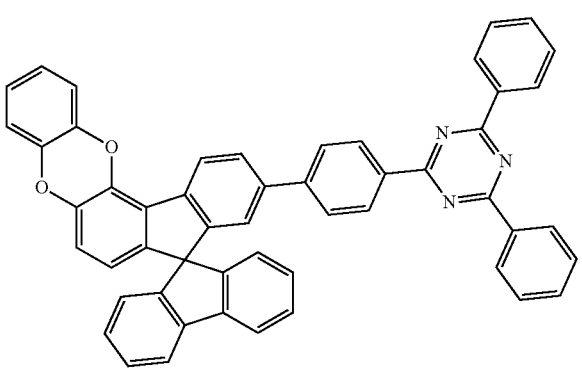
Cpd 25
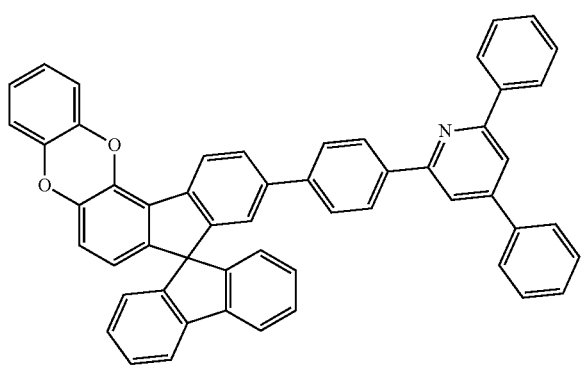
Cpd 26
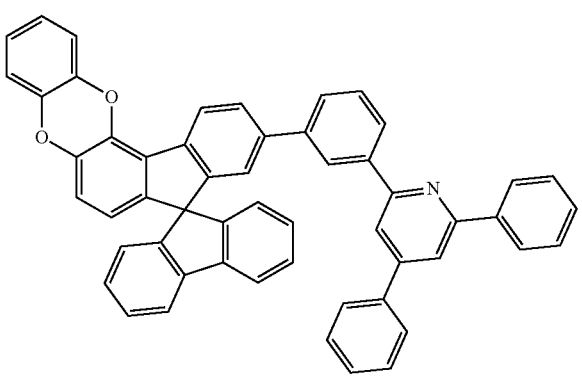

-continued
Cpd 27
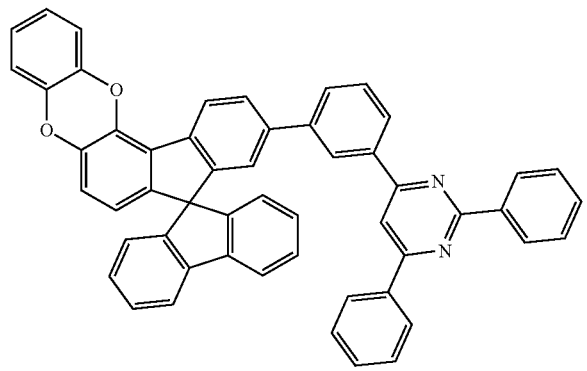
Cpd 28
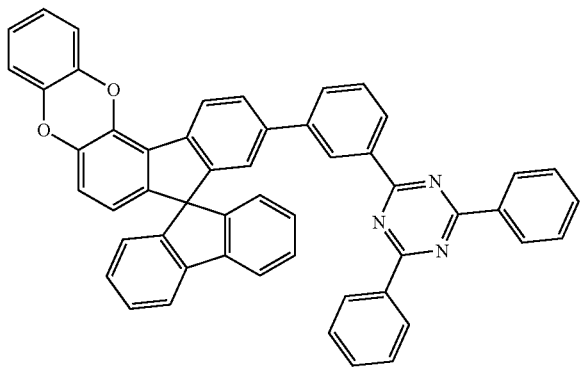
Cpd 29
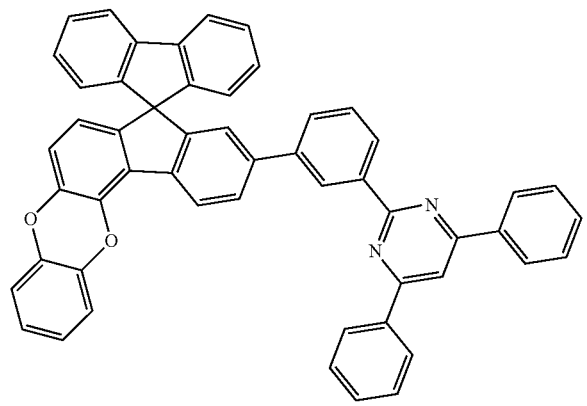
Cpd 30
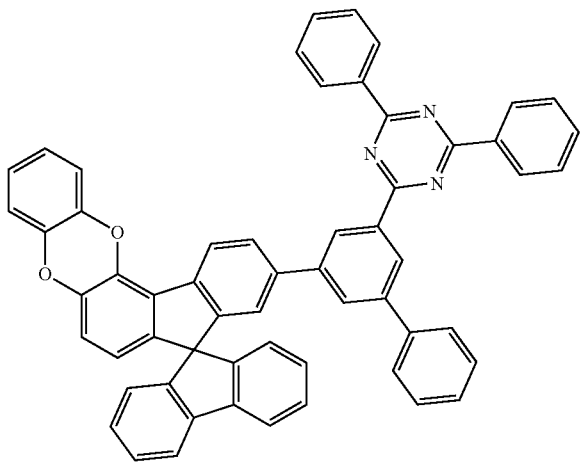
Cpd 31
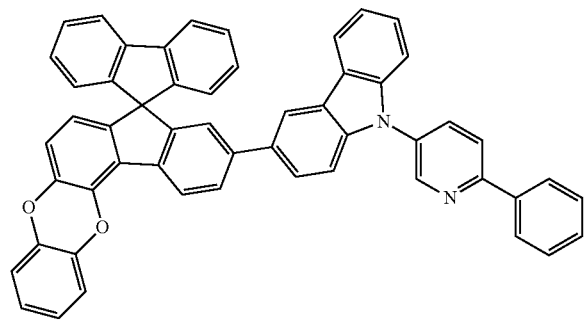
Cpd 32
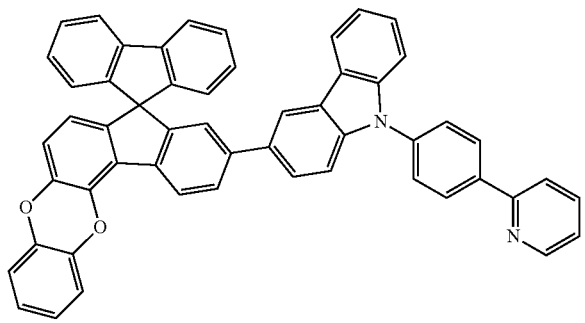
Cpd 33
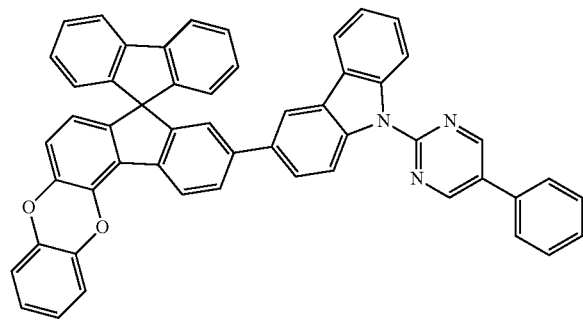
Cpd 34
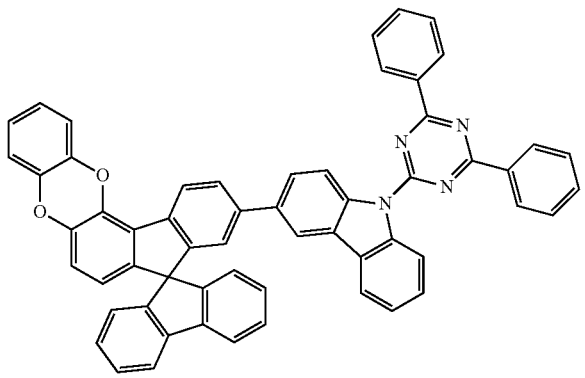

-continued
Cpd 35
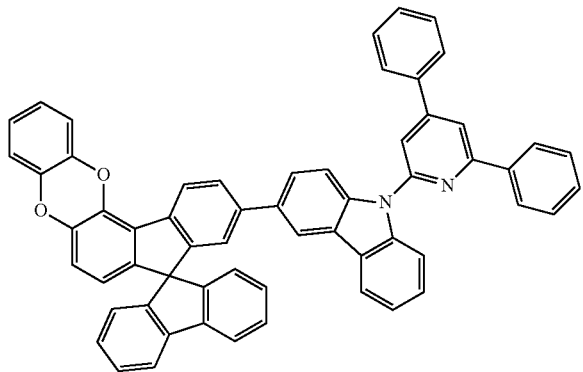
Cpd 36
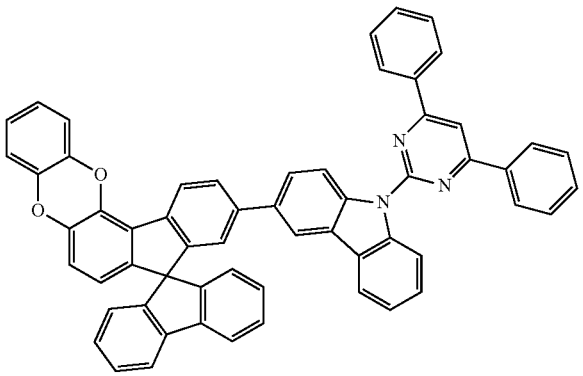
Cpd 37
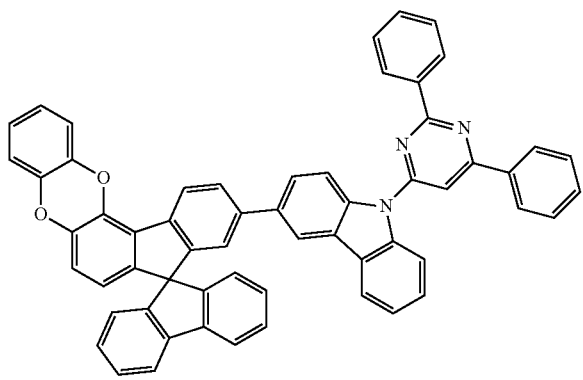
Cpd 38
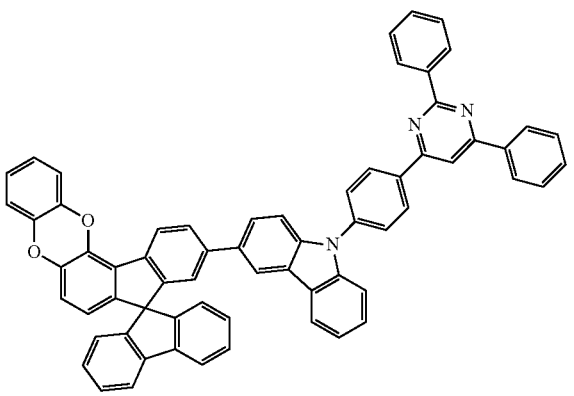
Cpd 39
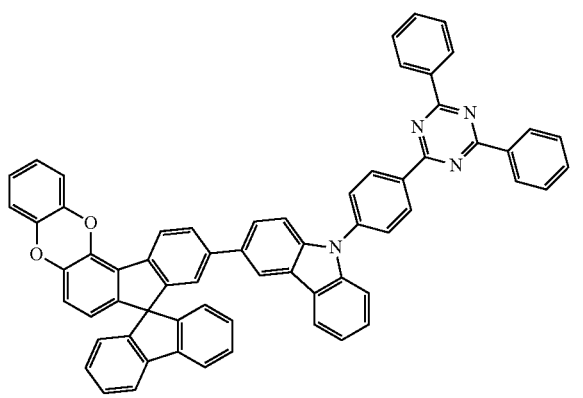
Cpd 40
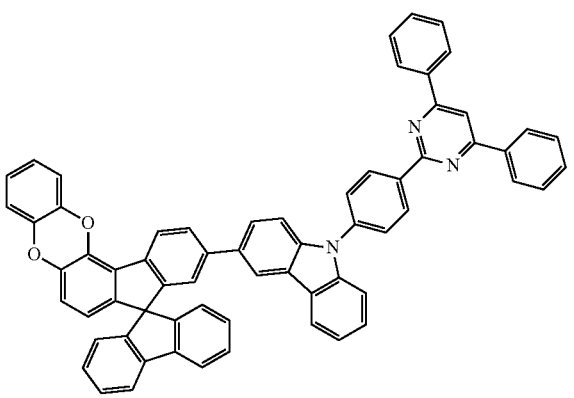
Cpd 41
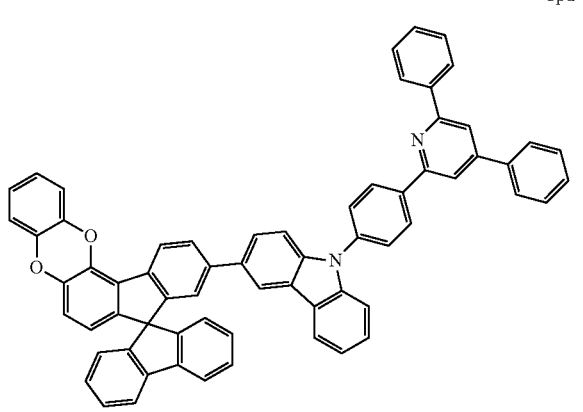
Cpd 42
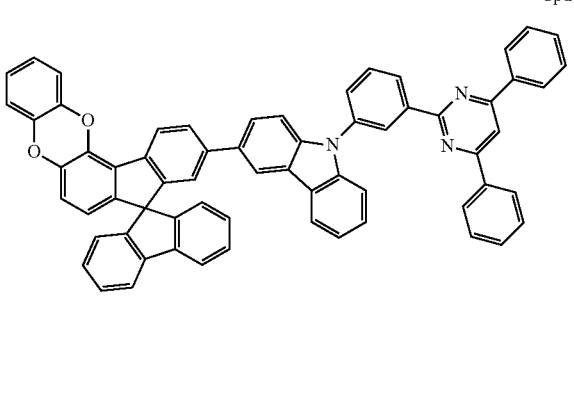

-continued
Cpd 43
Cpd 44
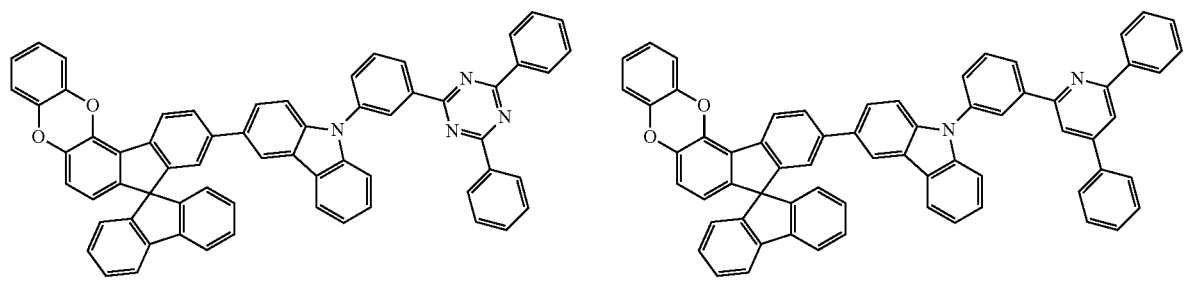
Cpd 45
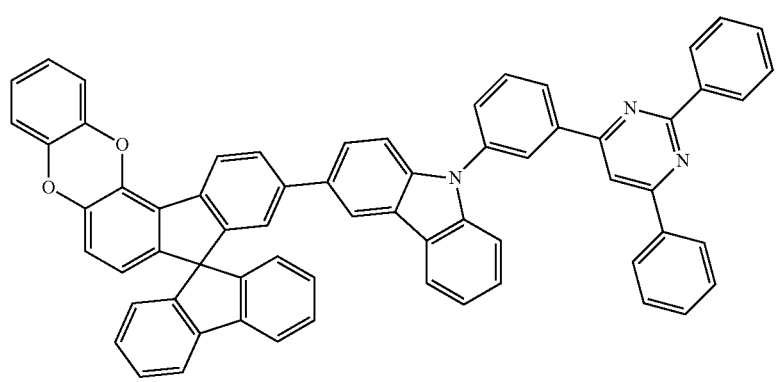
Cpd 46
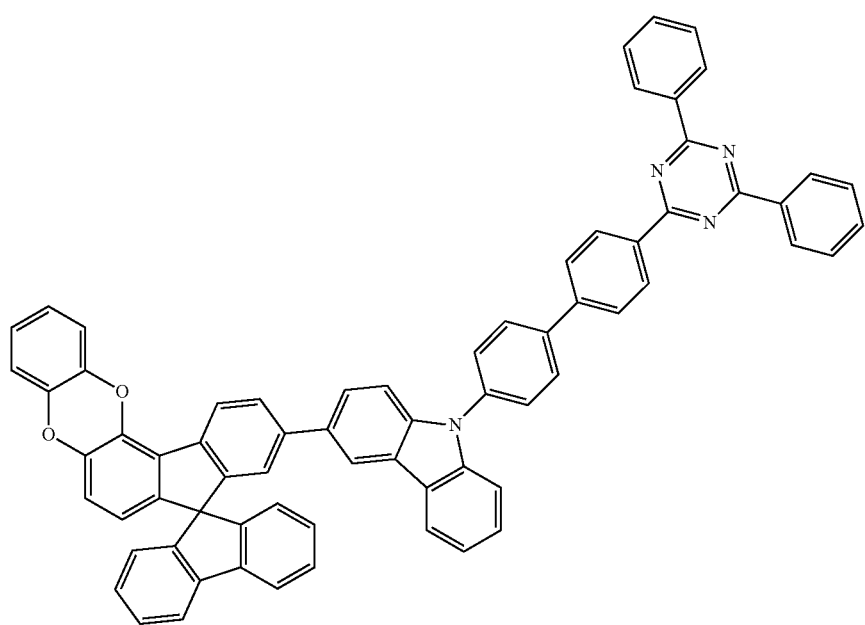

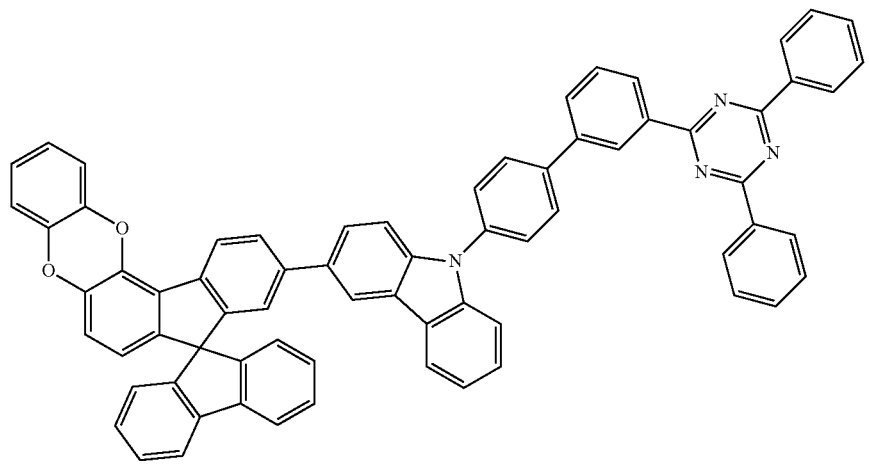

-continued
Cpd 52
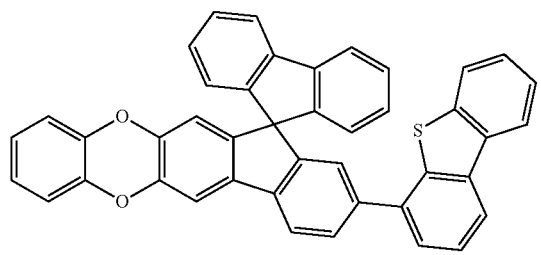
Cpd 53
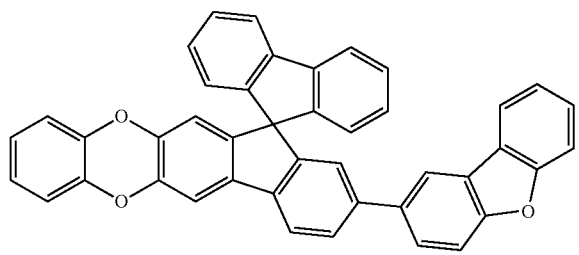
Cpd 54
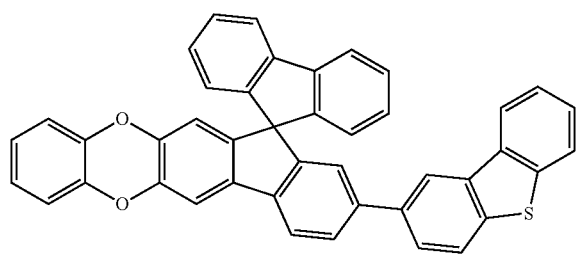
Cpd 55
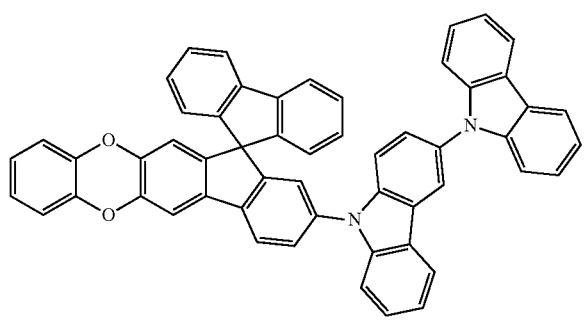
Cpd 56
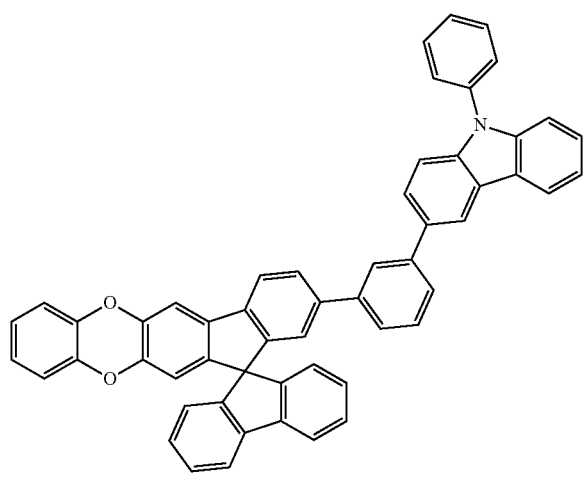
Cpd 57
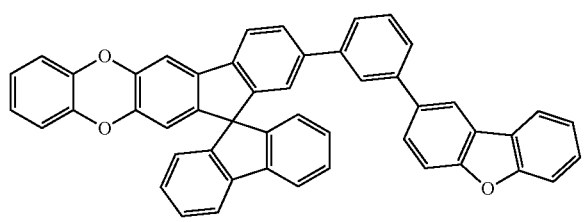
Cpd 58
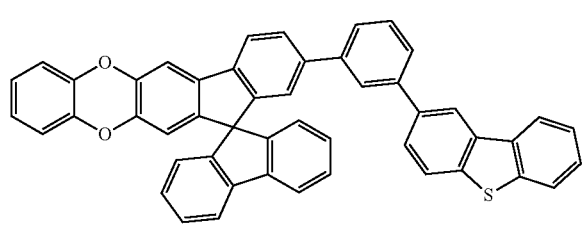
Cpd 59
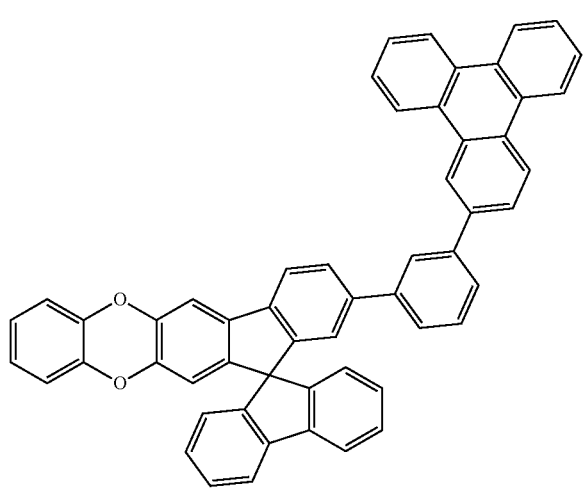

-continued
Cpd 60
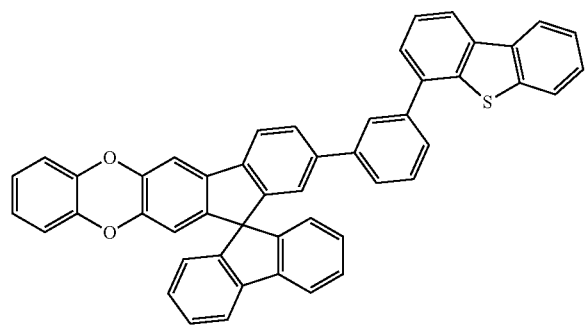
Cpd 61
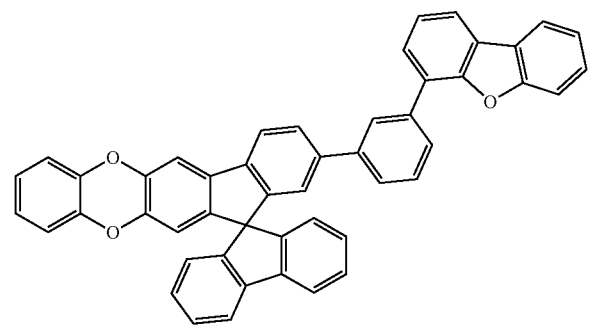
Cpd 62
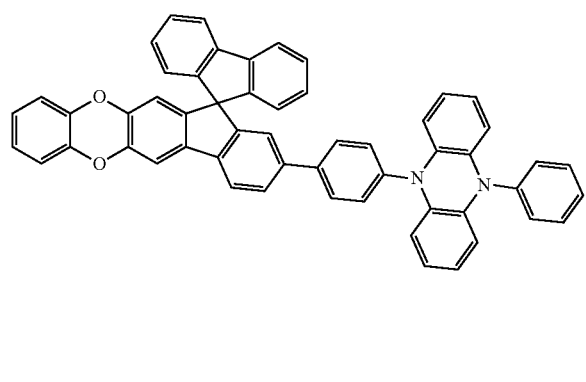
Cpd 63
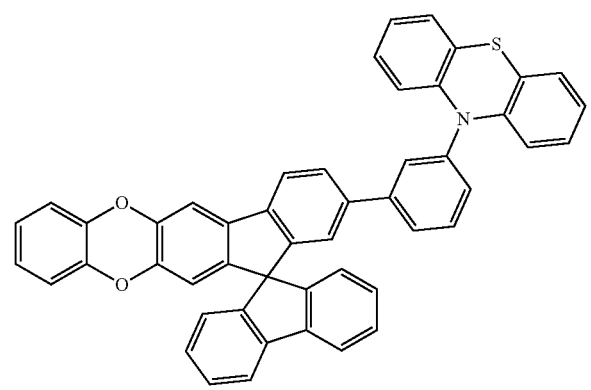
Cpd 64
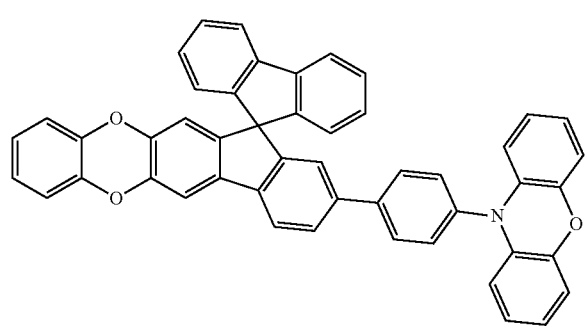
Cpd 65
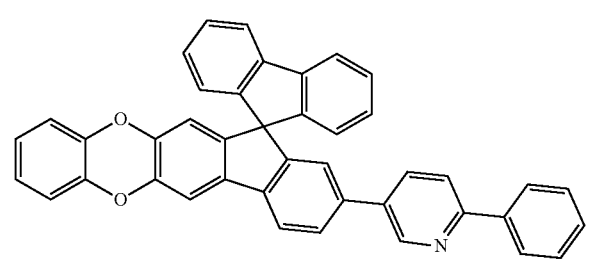
Cpd 66
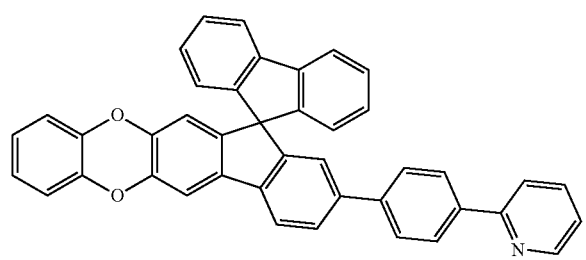
Cpd 67
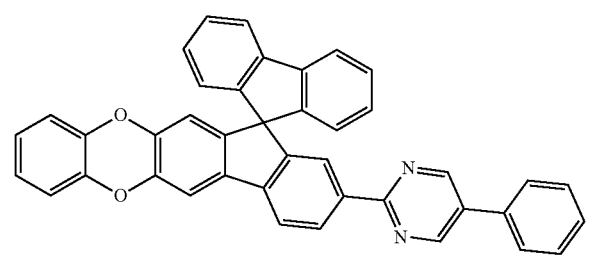

-continued
Cpd 68
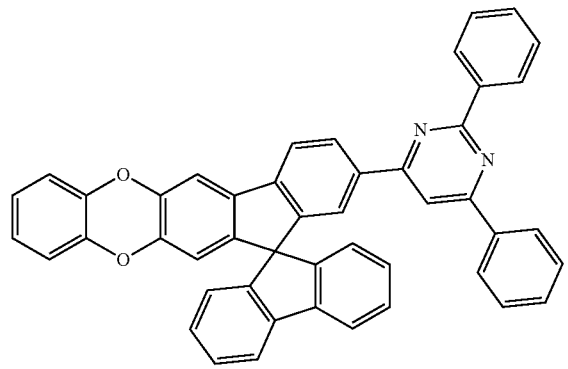
Cpd 69
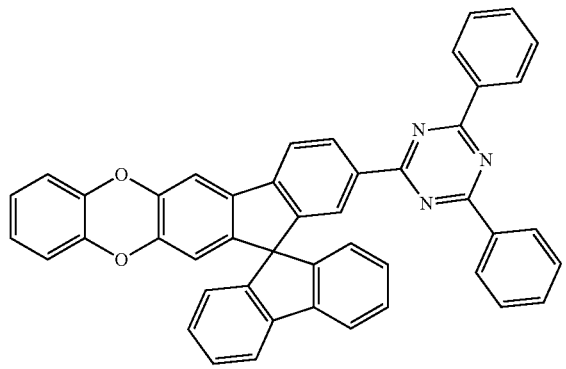
Cpd 70
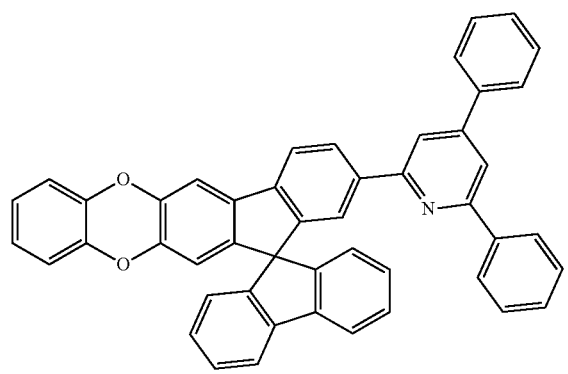
Cpd 71
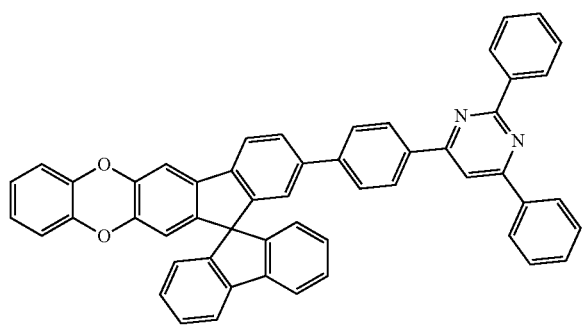
Cpd 72
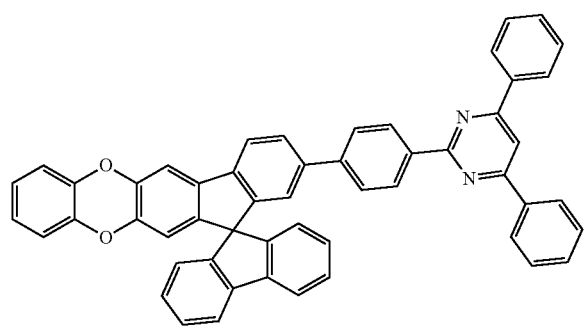
Cpd 73
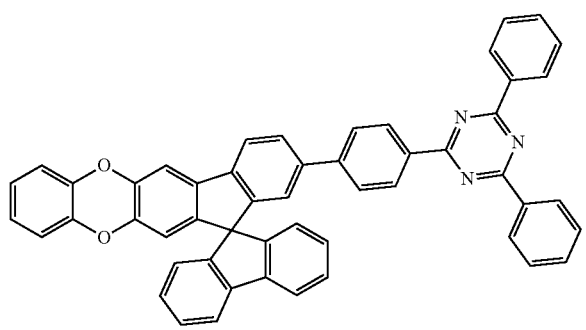
Cpd 74
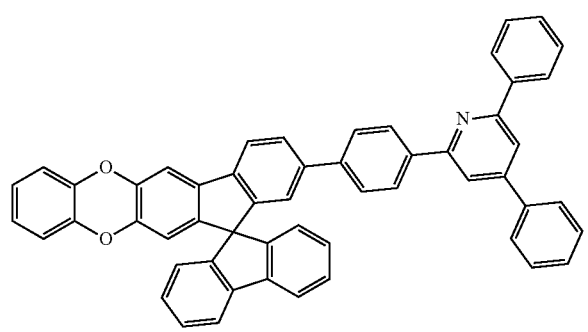
Cpd 75
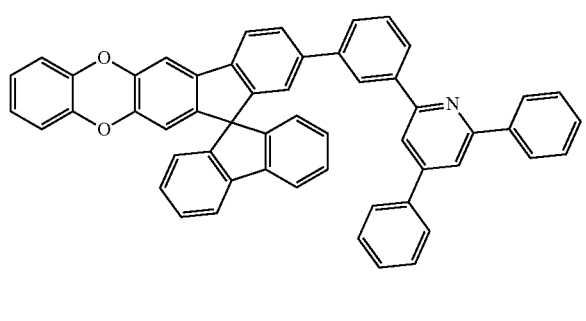

-continued
Cpd 76
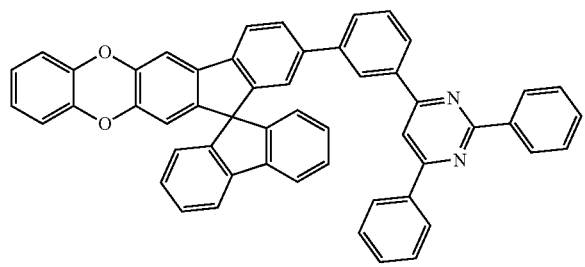
Cpd 77
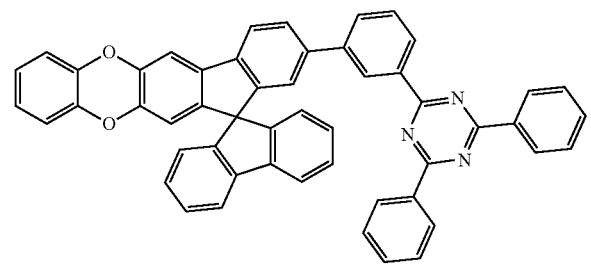
Cpd 78
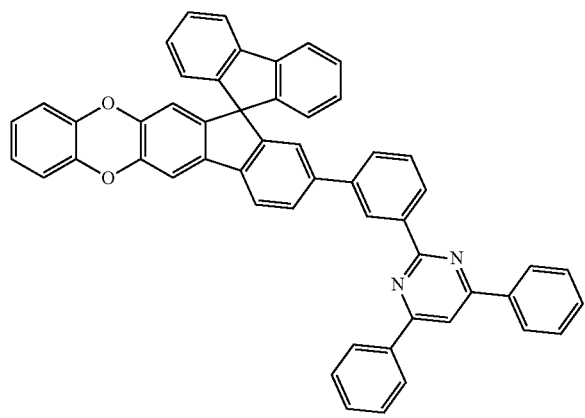
Cpd 79
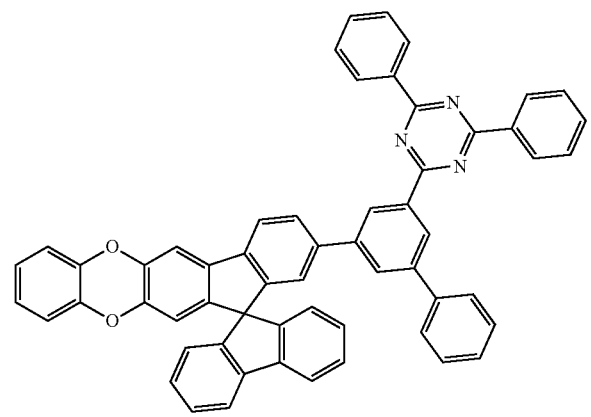
Cpd 80
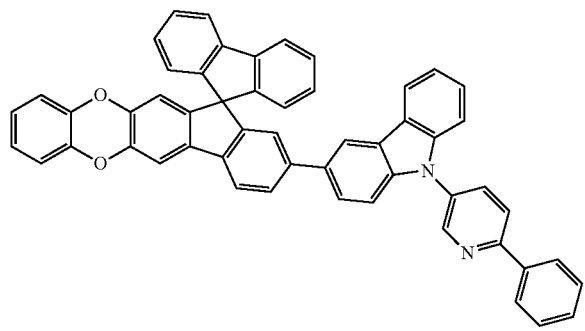
Cpd 81
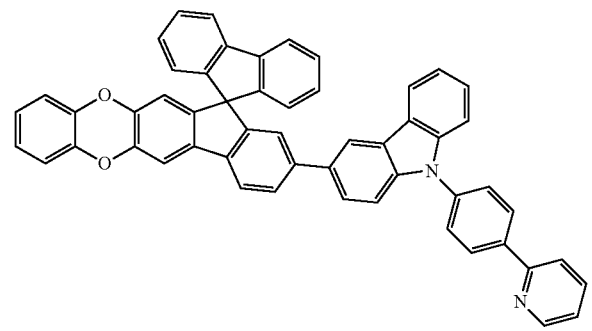
Cpd 82
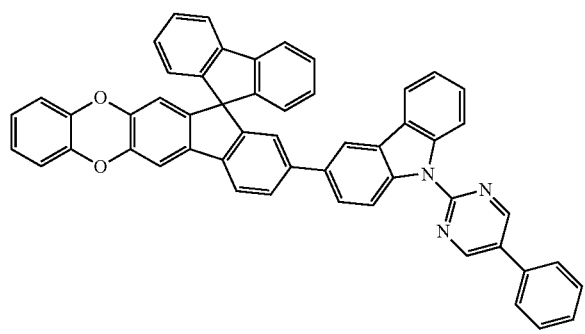
Cpd 83
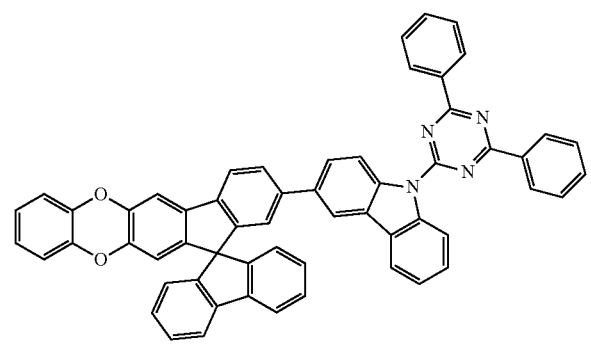

-continued
Cpd 84
Cpd 85
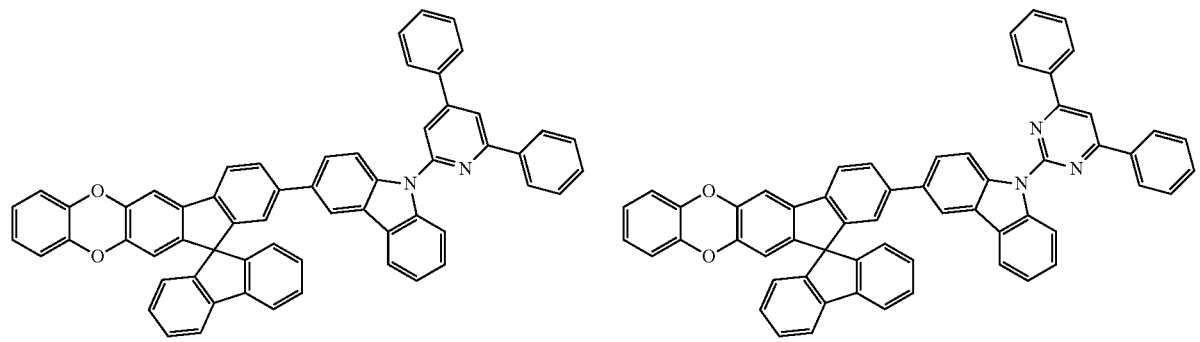
Cpd 86
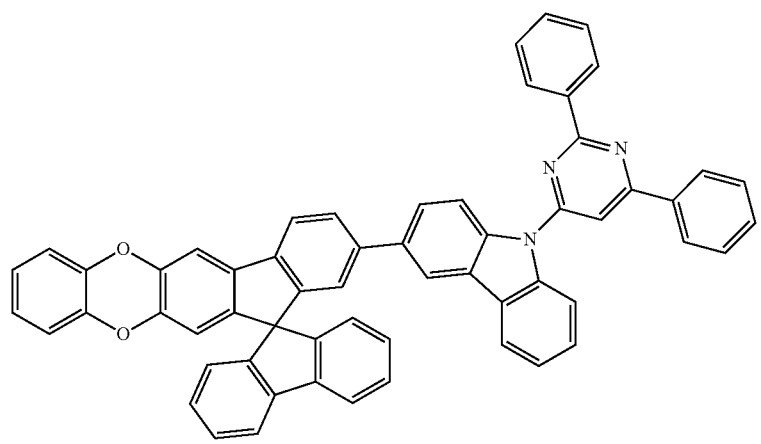
Cpd 87
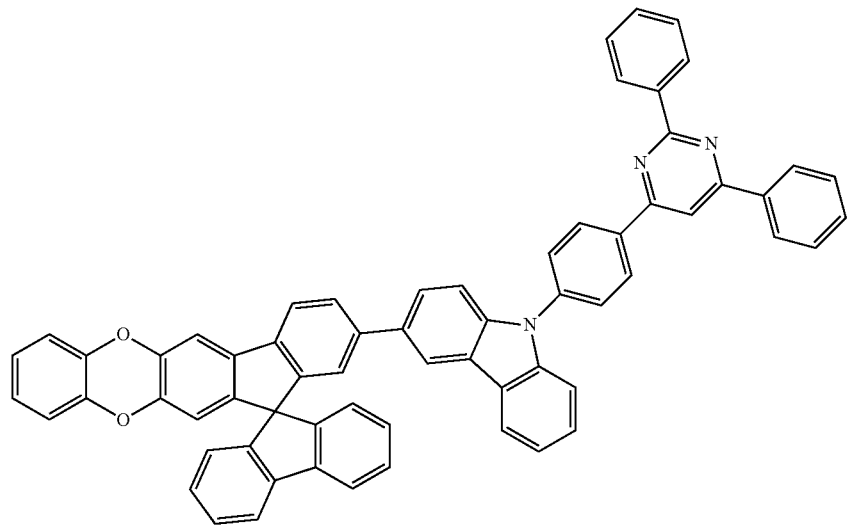

-continued
Cpd 88
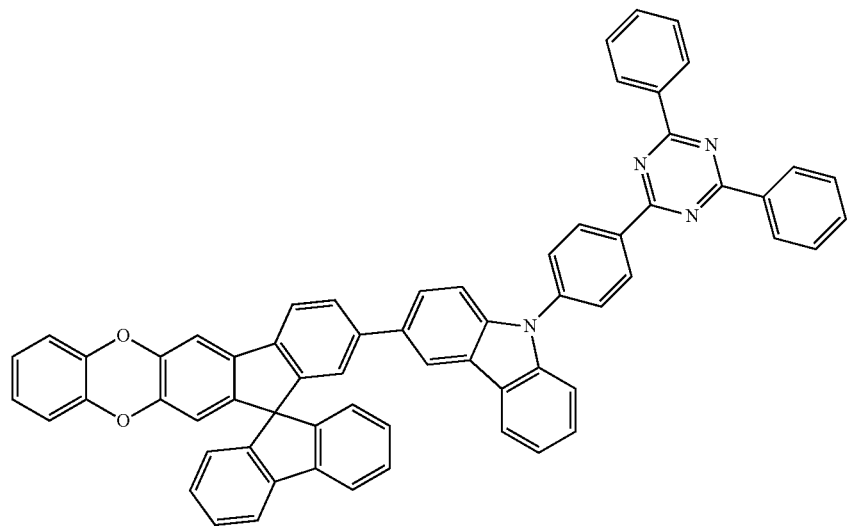
Cpd 89
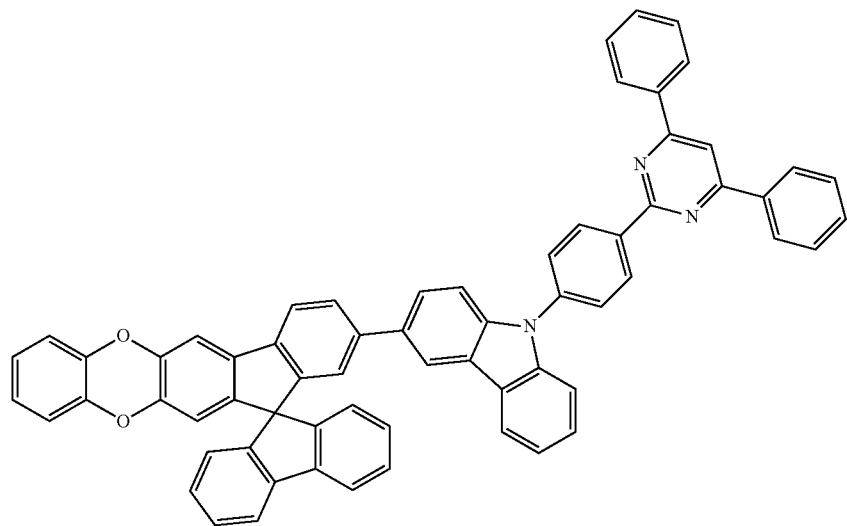
Cpd 90
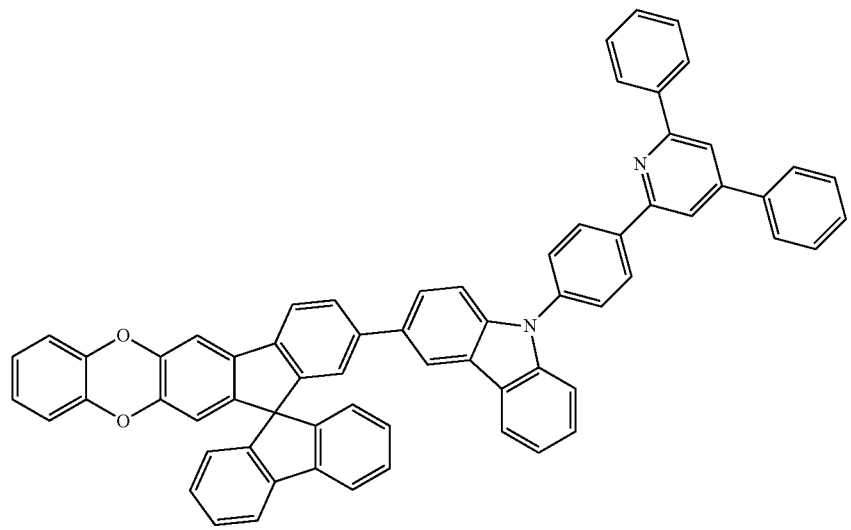

-continued
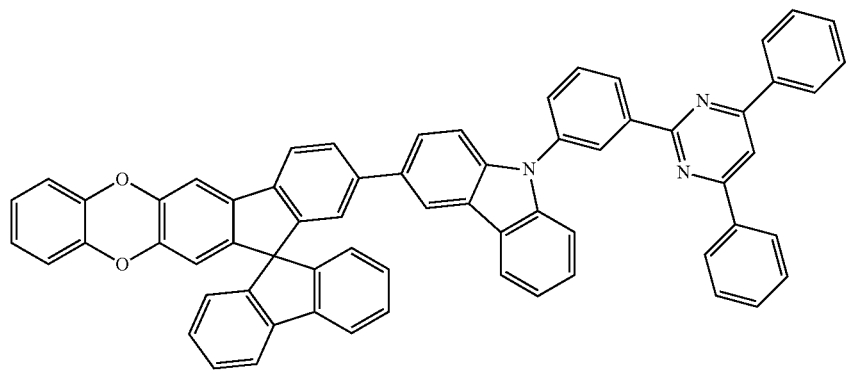
Cpd 91
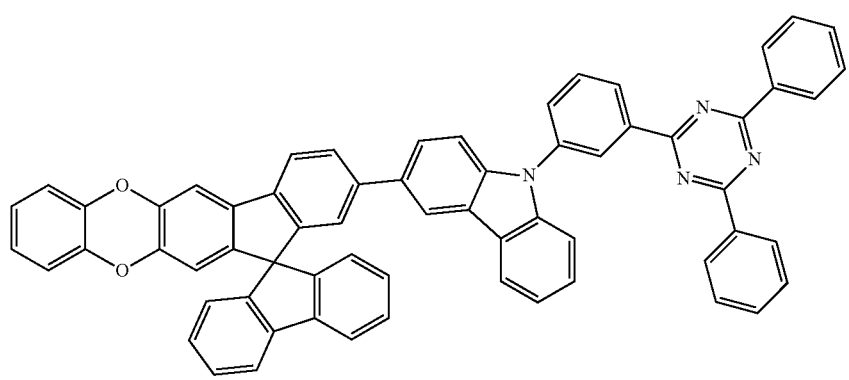
Cpd 92
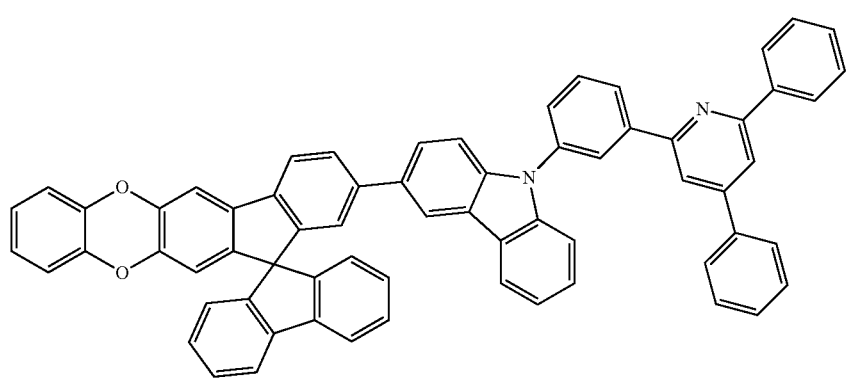
Cpd 93
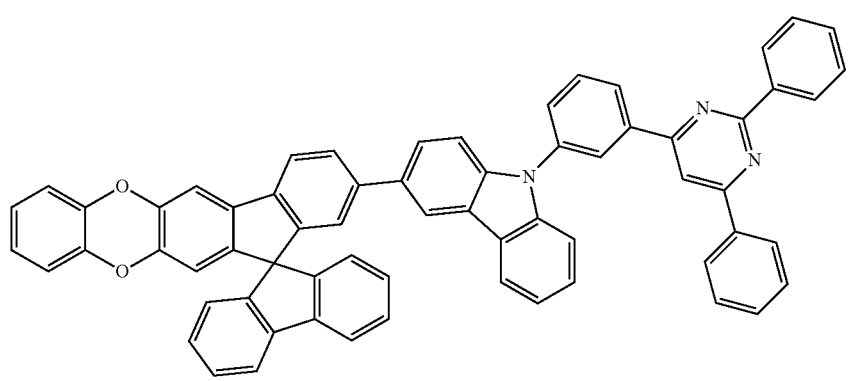
Cpd 94

-continued
Cpd 95
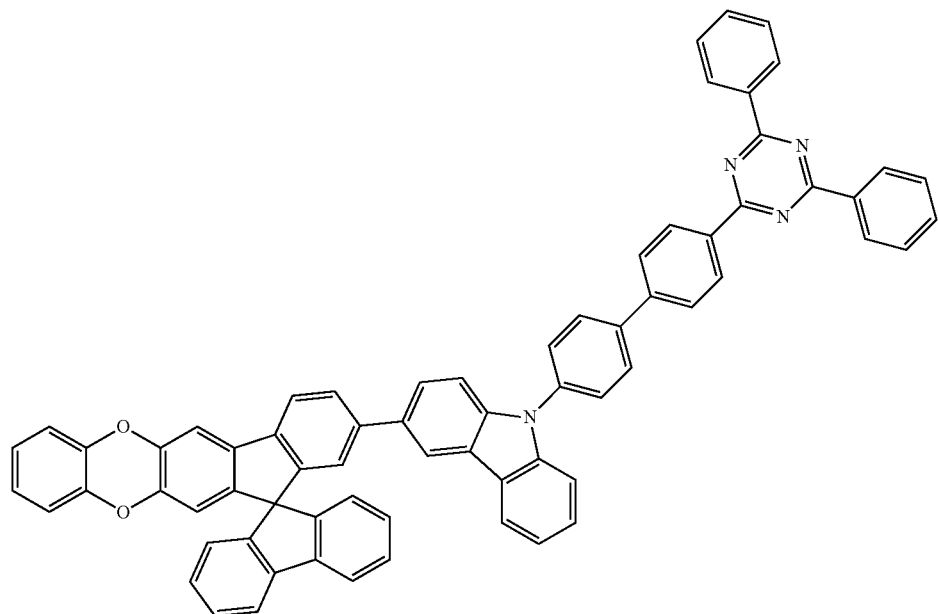
Cpd 96
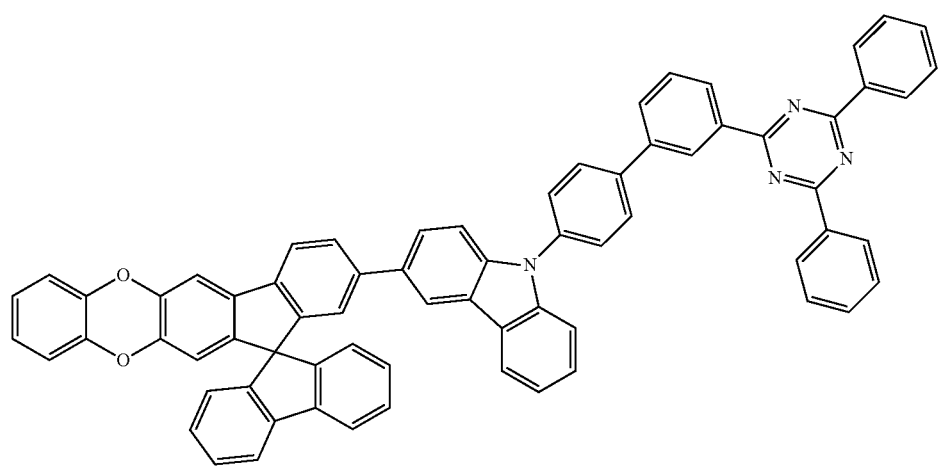
Cpd 97
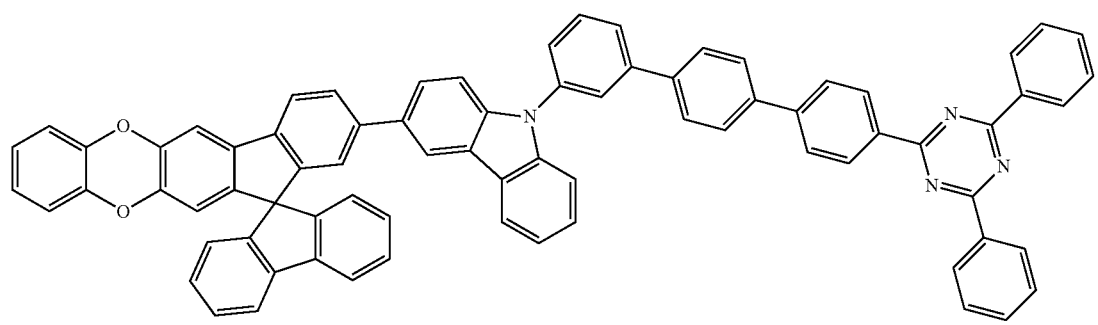

-continued
Cpd 98
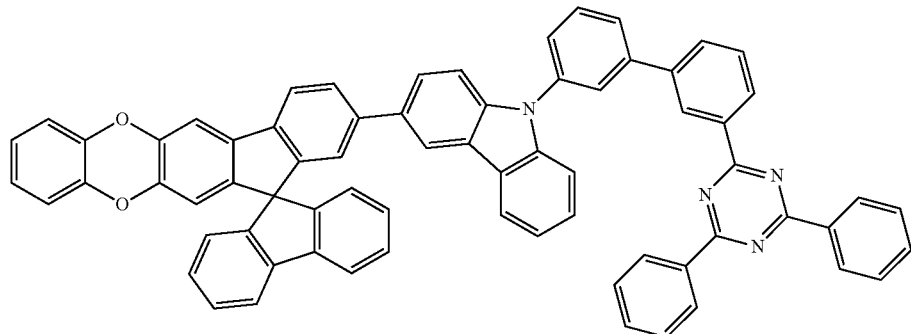
Cpd 99
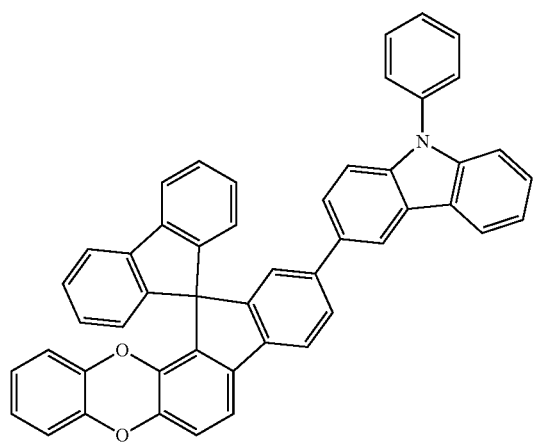
Cpd 100
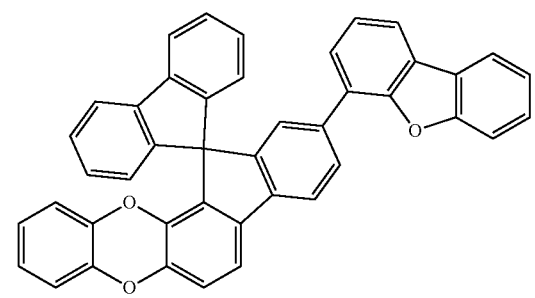
Cpd 101
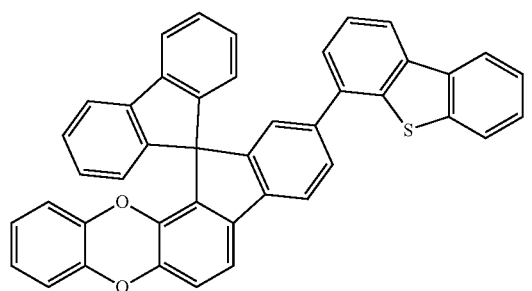
Cpd 102
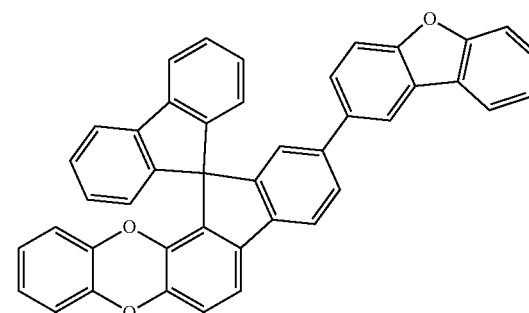
Cpd 103
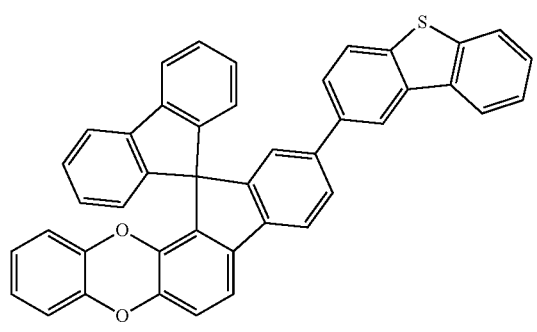
Cpd 104
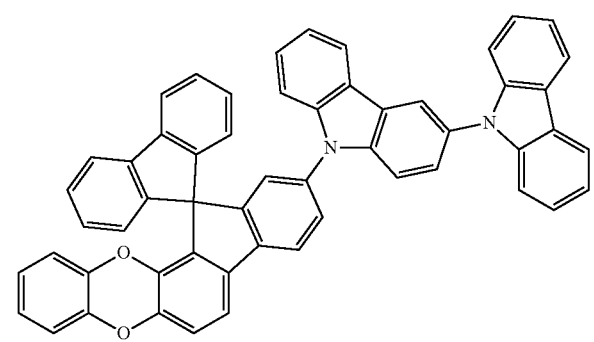

-continued
Cpd105
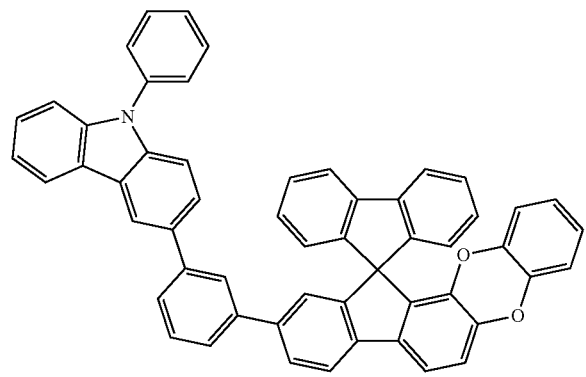
Cpd 106
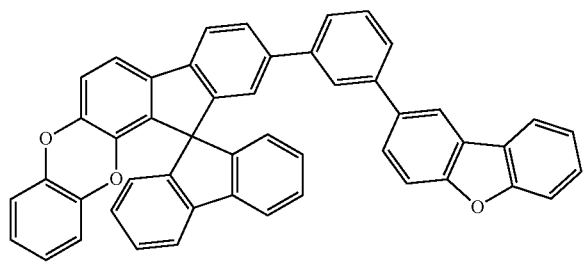
Cpd 107
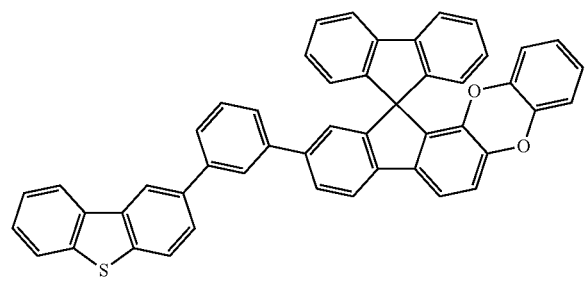
Cpd 108
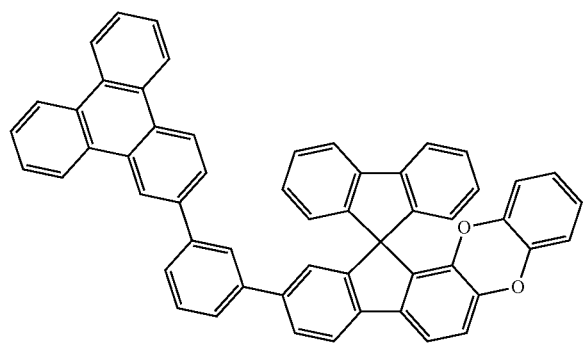
Cpd 109
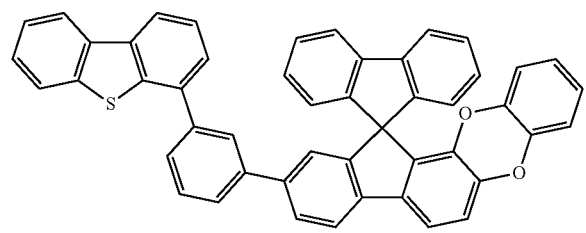
Cpd 110
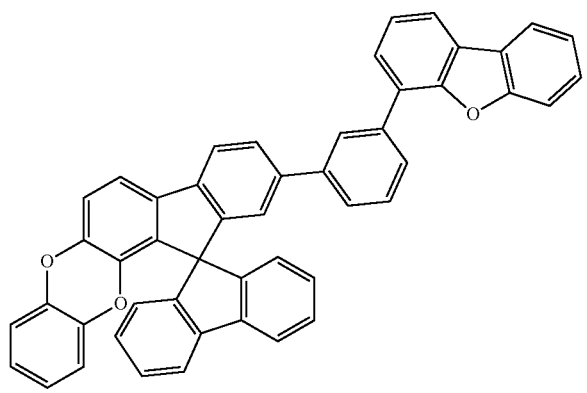

-continued
Cpd 111
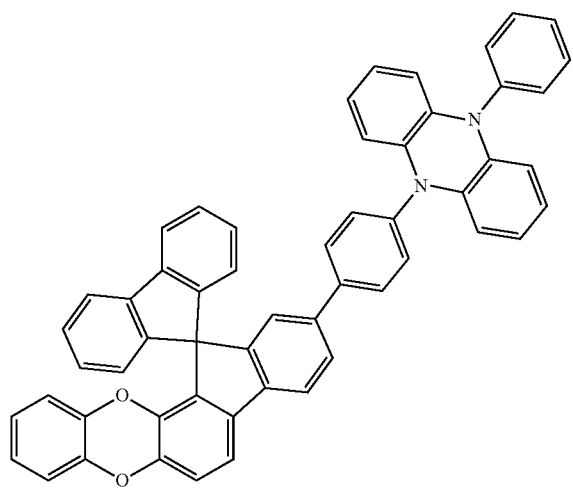
Cpd 112
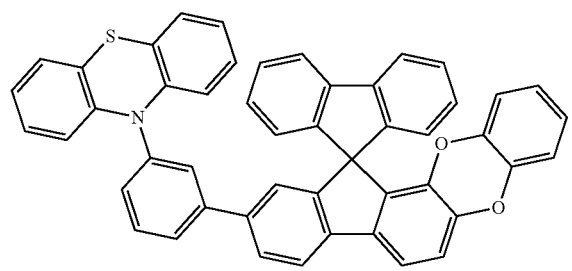
Cpd 113
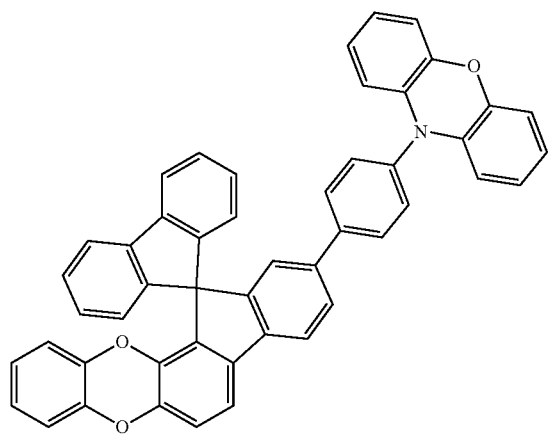
Cpd 114
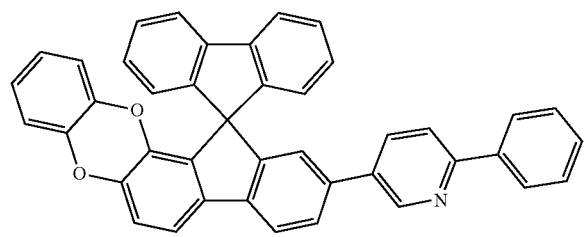
Cpd 115
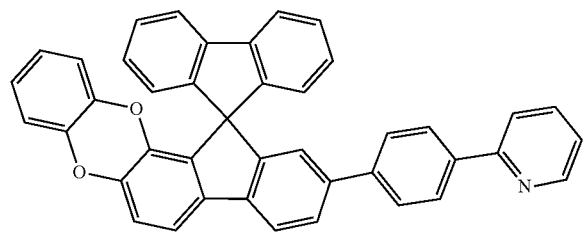
Cpd 116
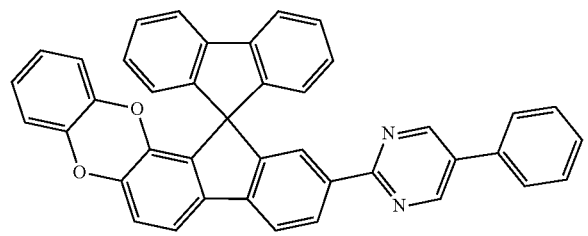
Cpd 117
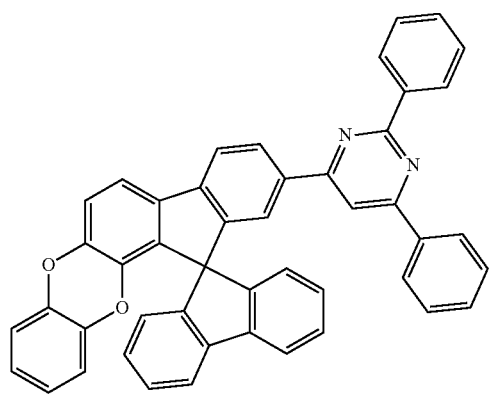
Cpd 118
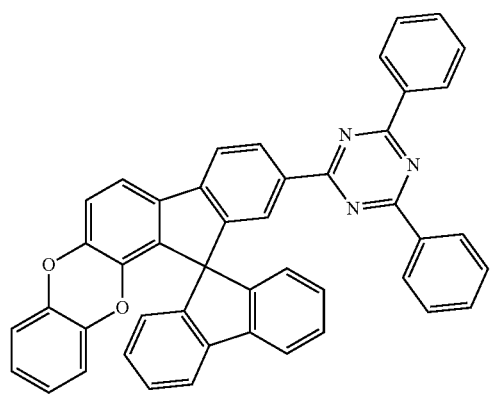

-continued
Cpd 119
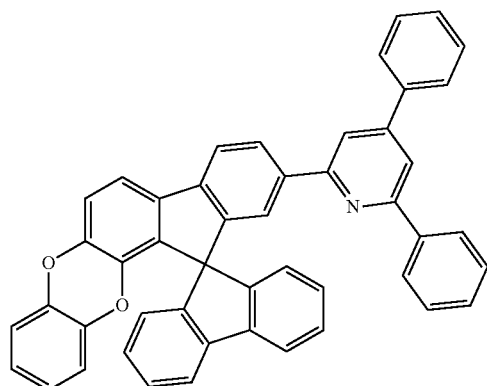
Cpd 120
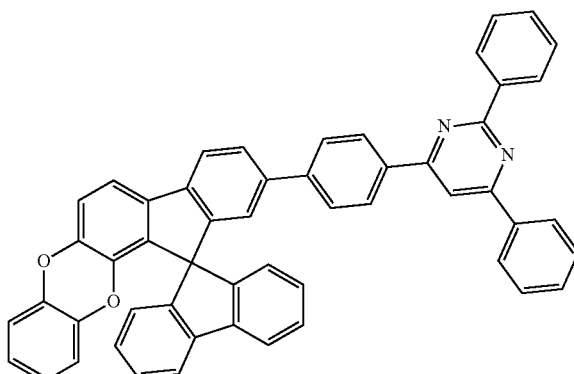
Cpd 121
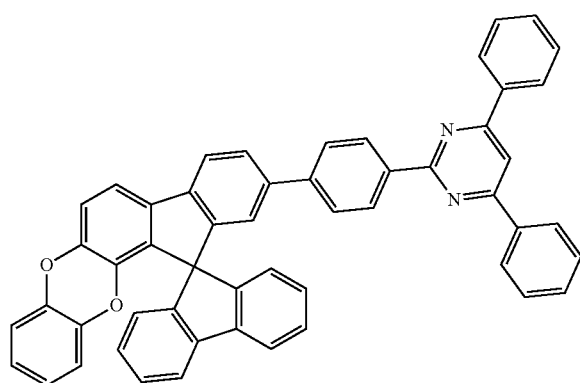
Cpd 122
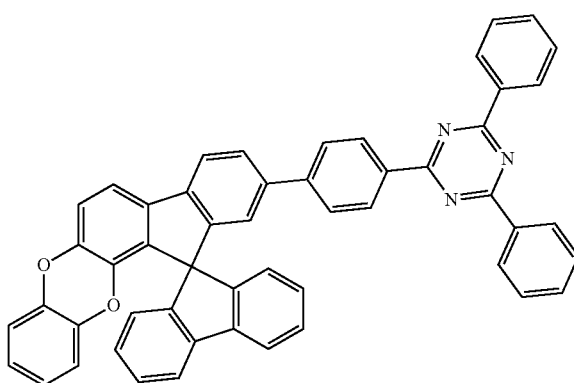
Cpd 123
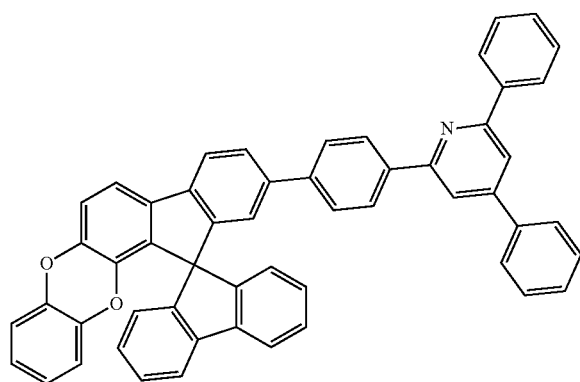
Cpd 124
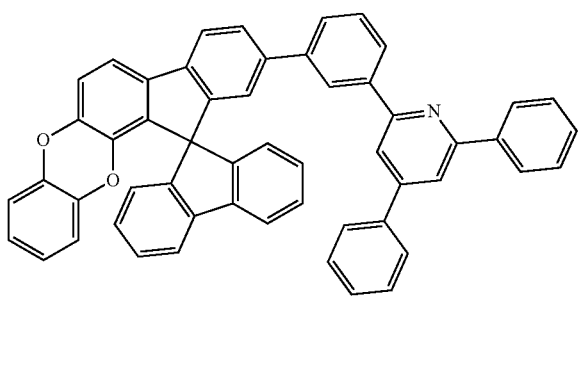
Cpd 125
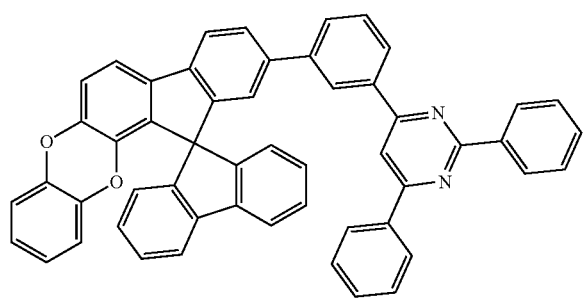
Cpd 126
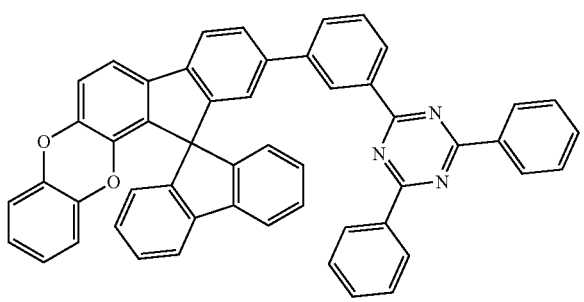

-continued
Cpd 127
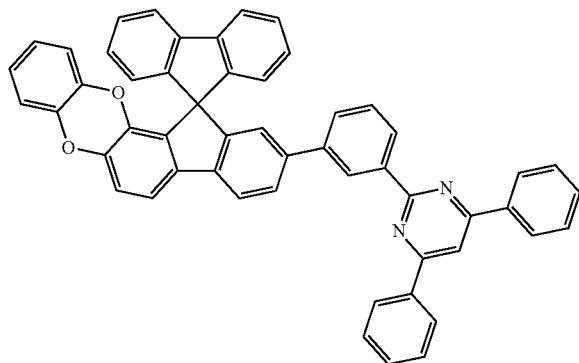
Cpd 128
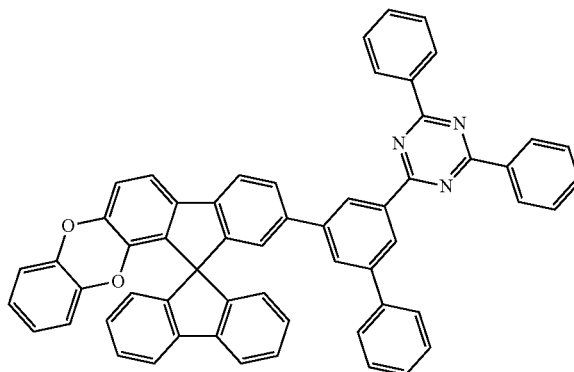
Cpd 129
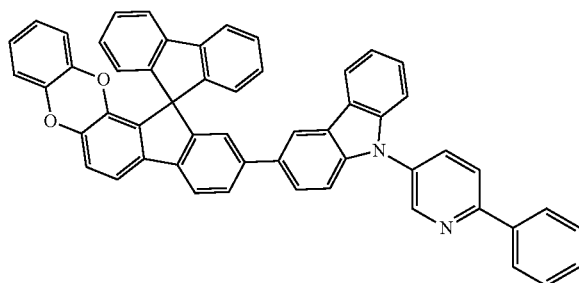
Cpd 130
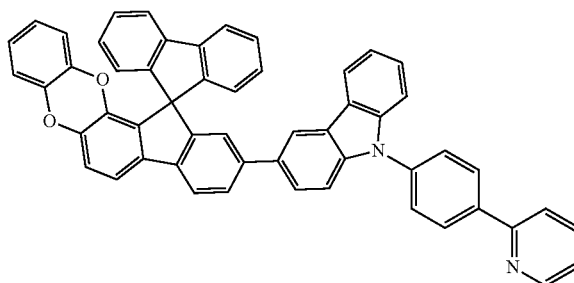
Cpd 131
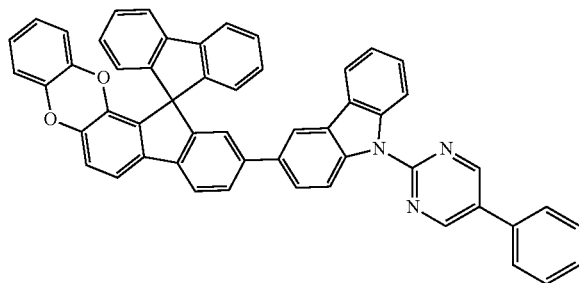
Cpd 132
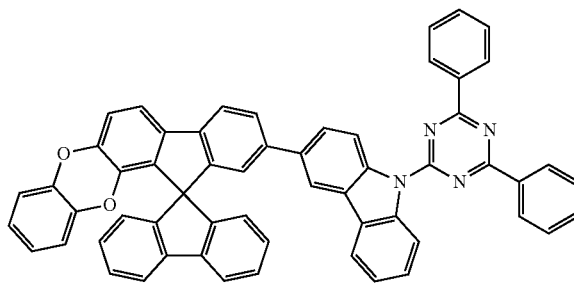
Cpd 133
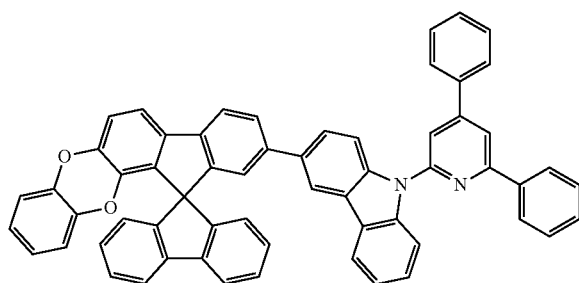
Cpd 134
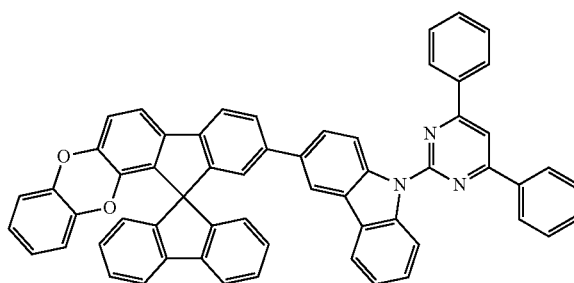

Cpd 135
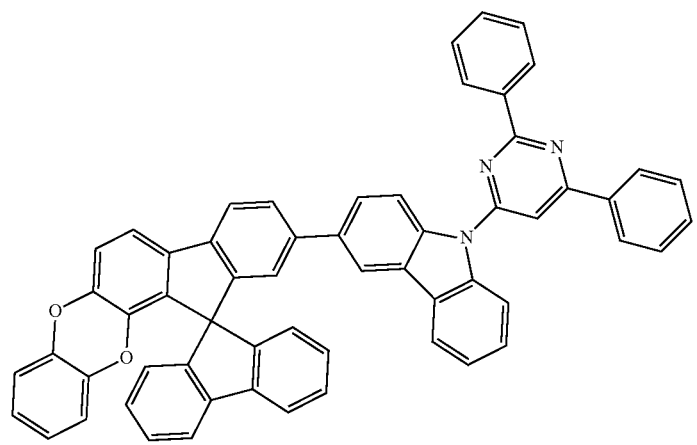
Cpd 136
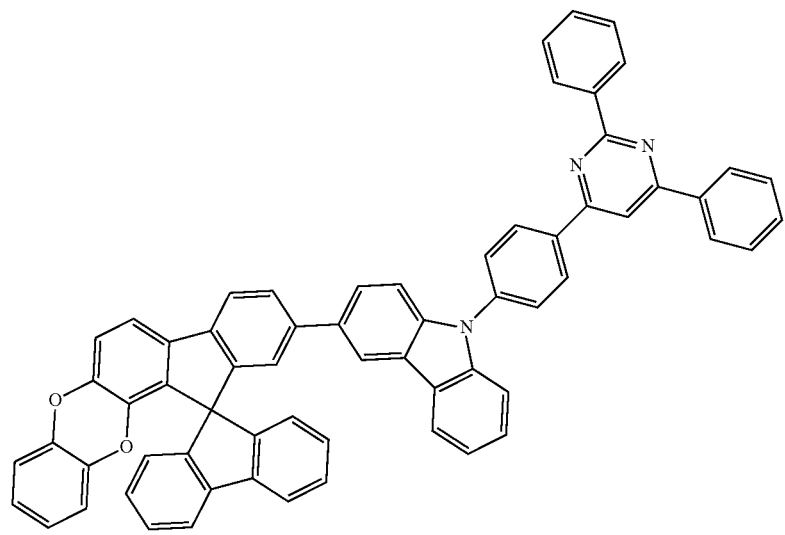
Cpd 137
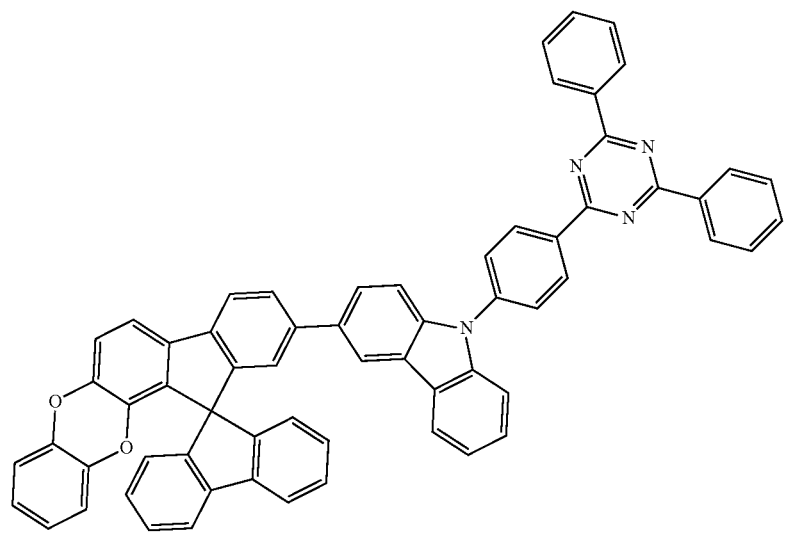

Cpd 138
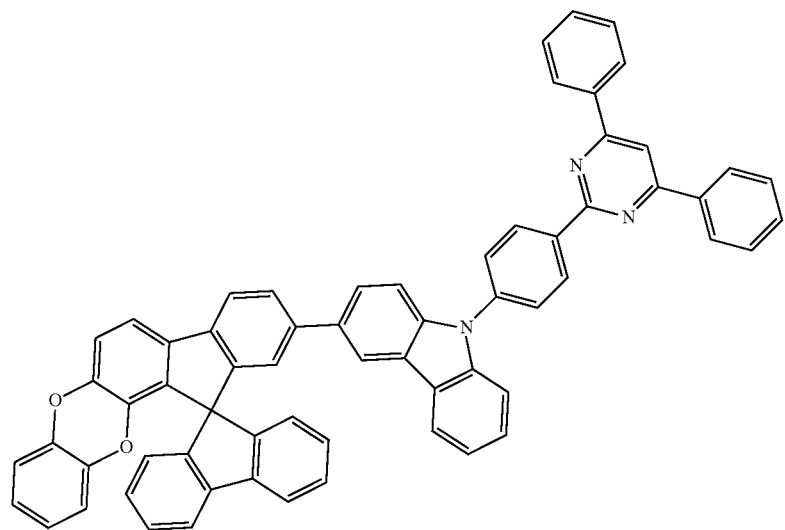
Cpd 139
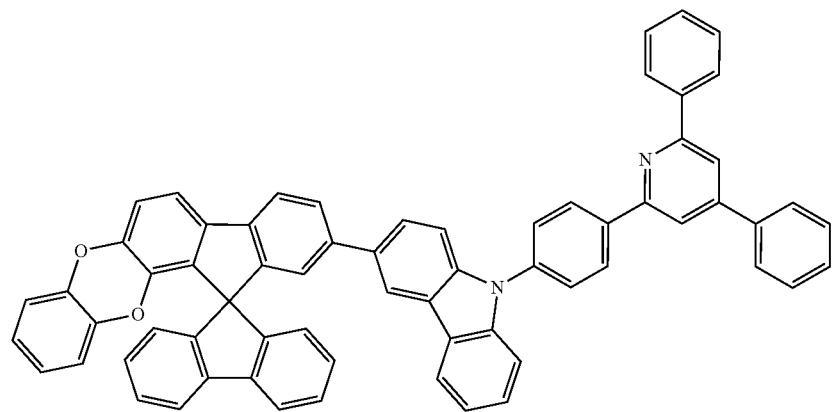
Cpd 140
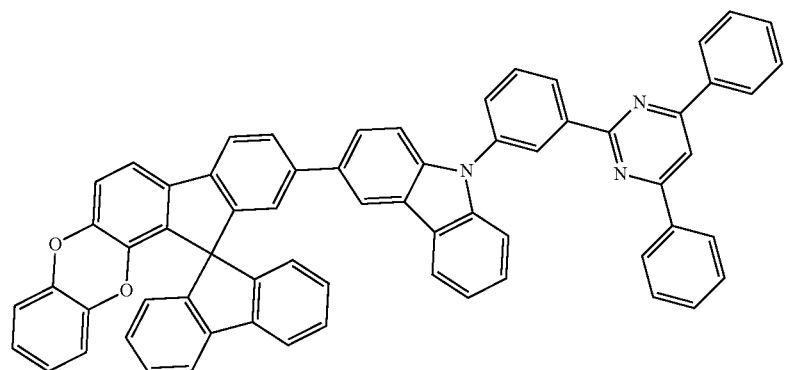

Cpd 141
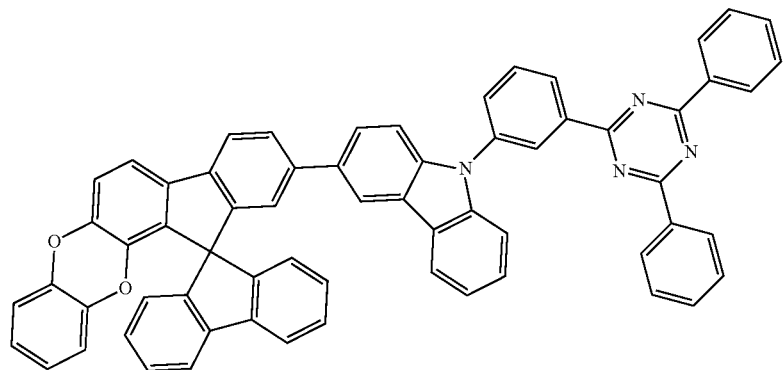
Cpd 142
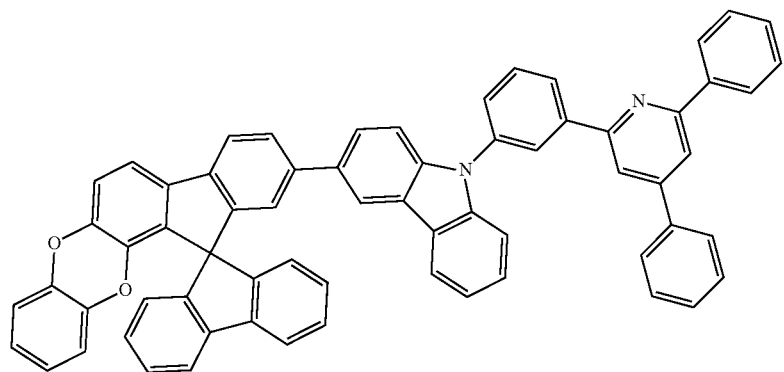
Cpd 143
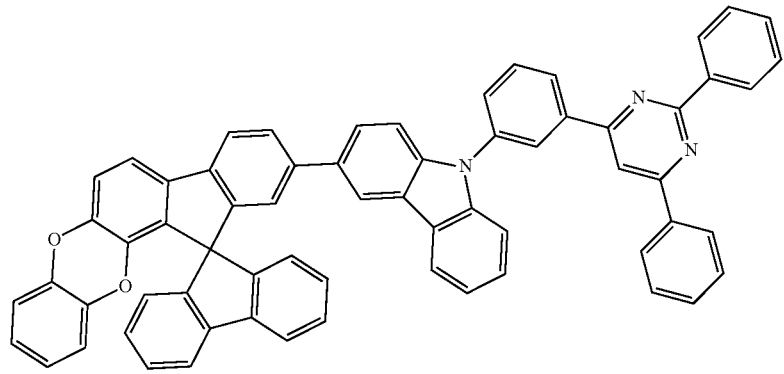
Cpd 144
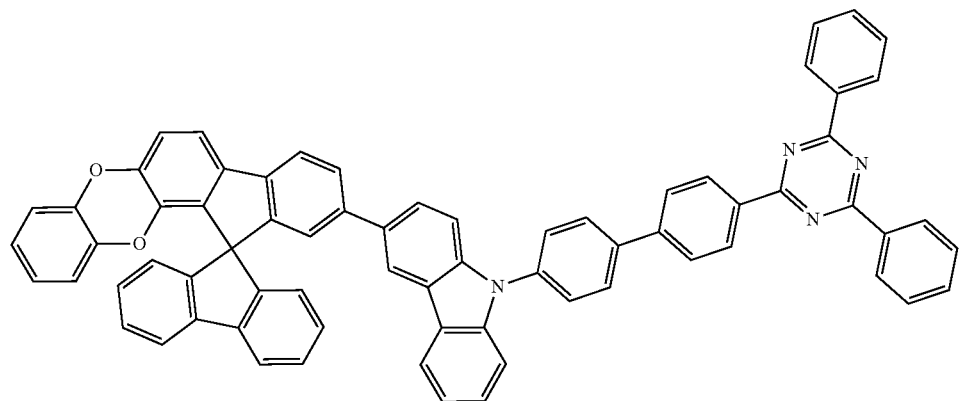

Cpd 145
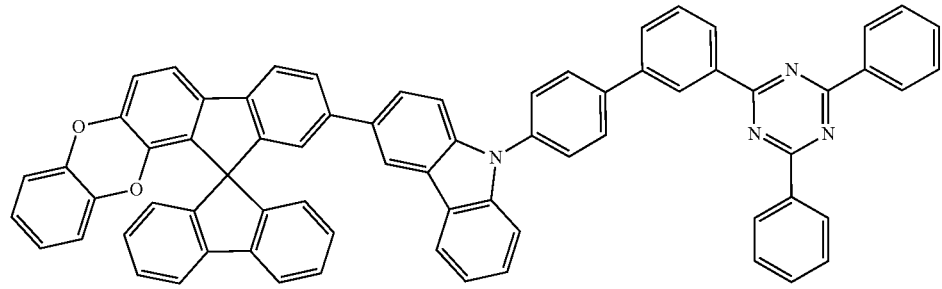
Cpd 146
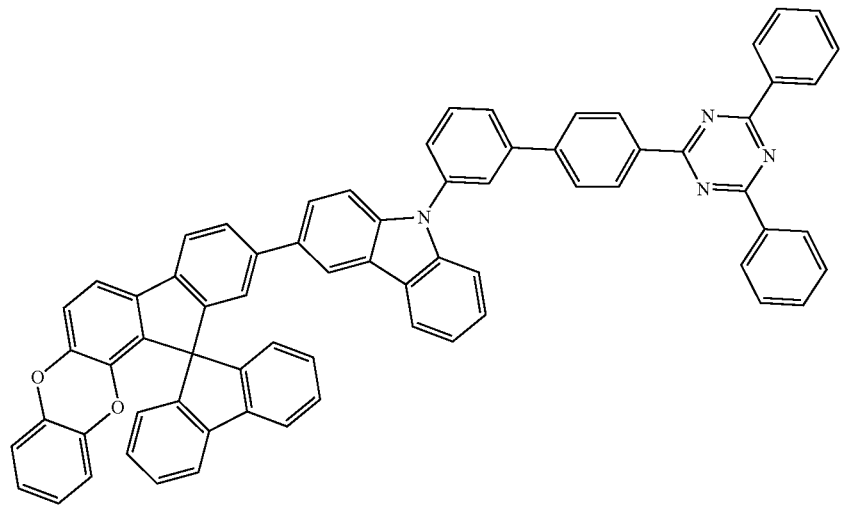
Cpd 147
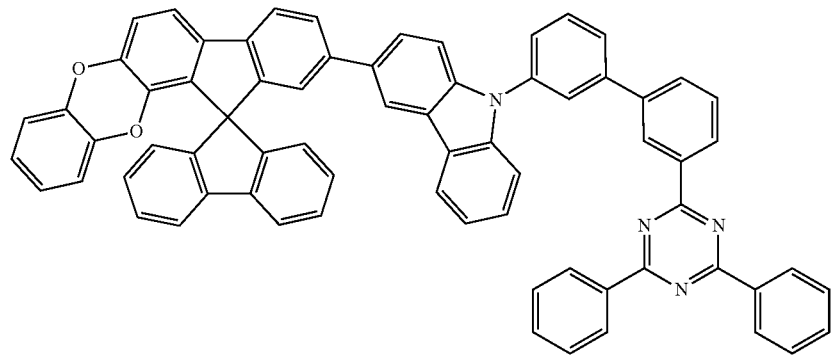
Cpd 148
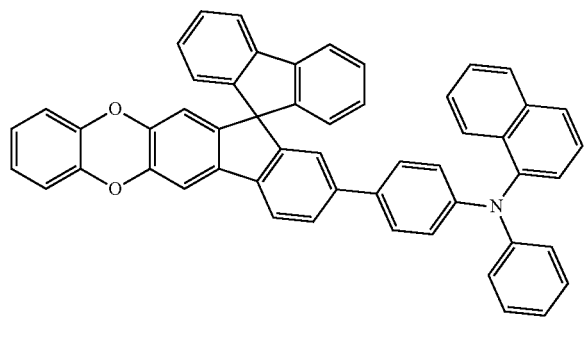
Cpd 149
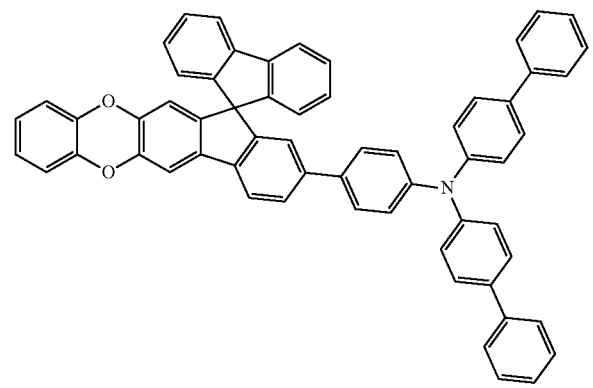

-continued
Cpd 150
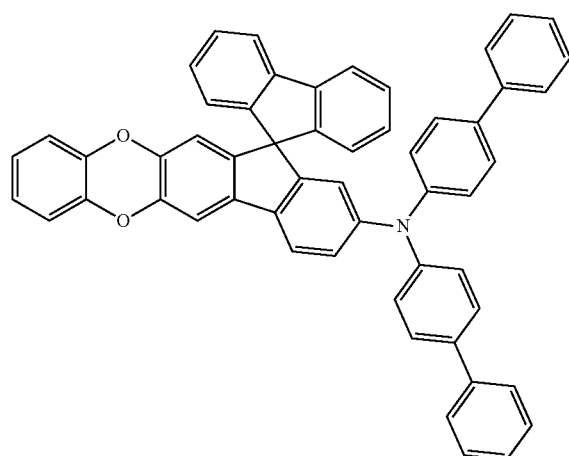
Cpd 151
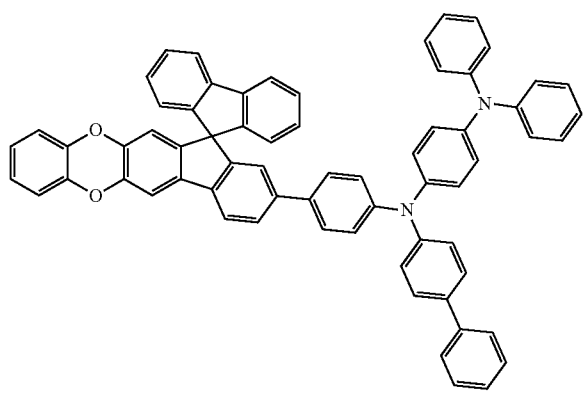
Cpd 152
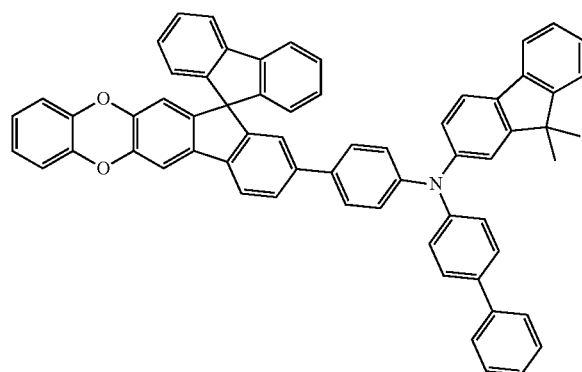
Cpd 153
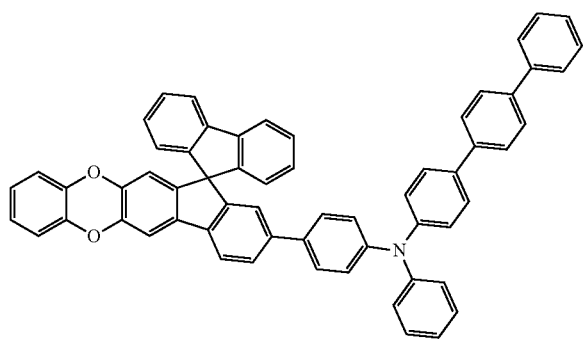
Cpd 154
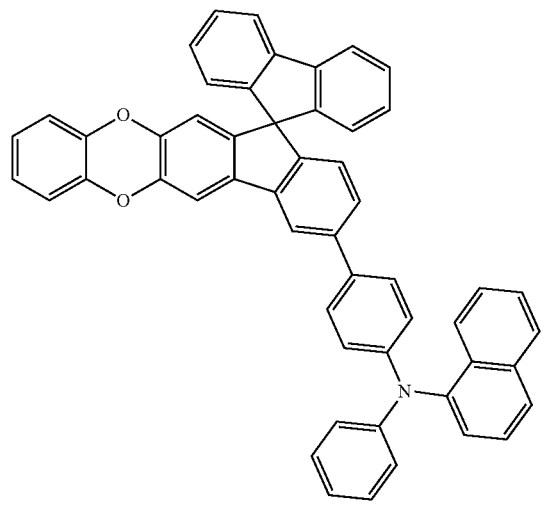
Cpd 155
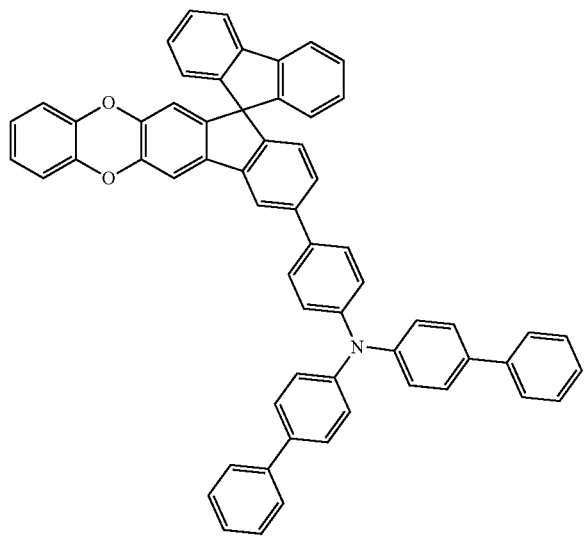

Cpd 157
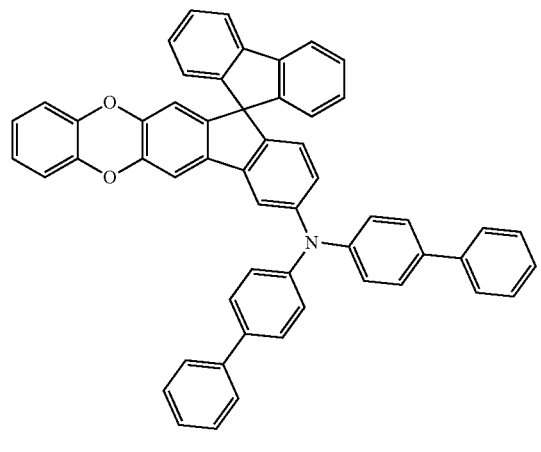
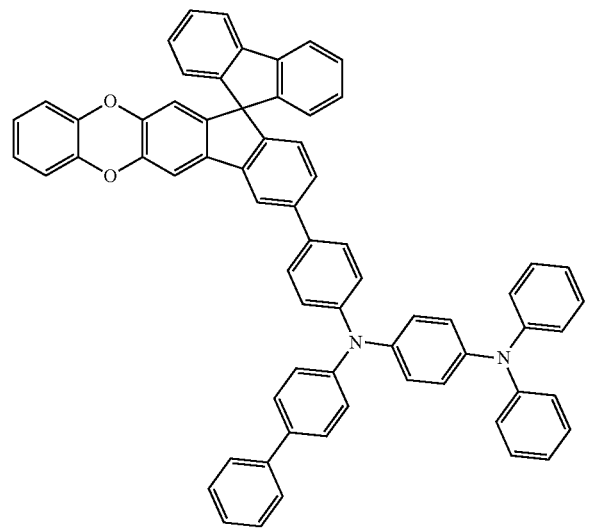
Cpd 158
Cpd 159
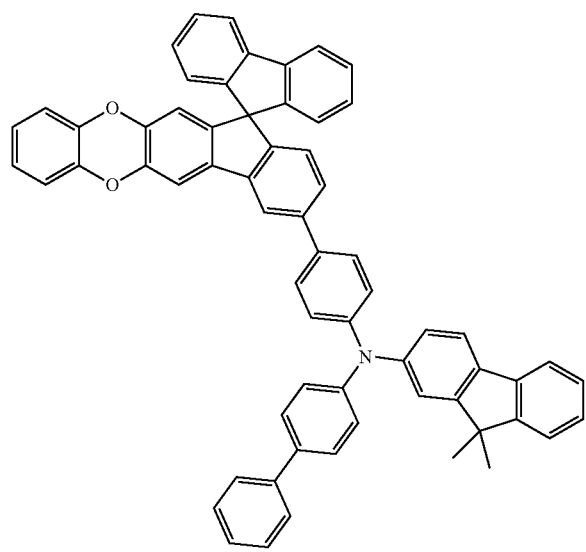
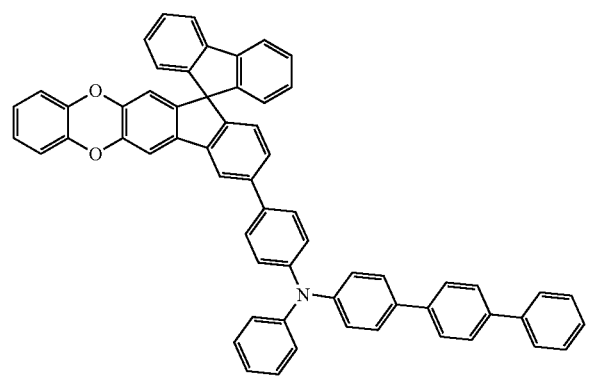

-continued
Cpd 160
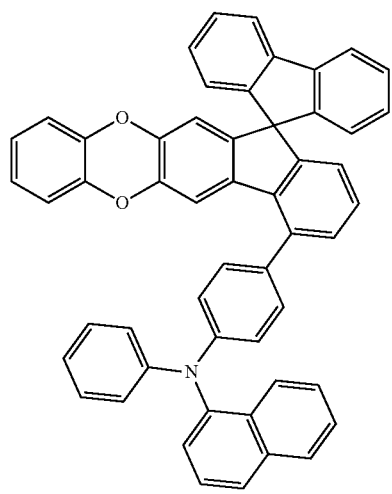
Cpd 161
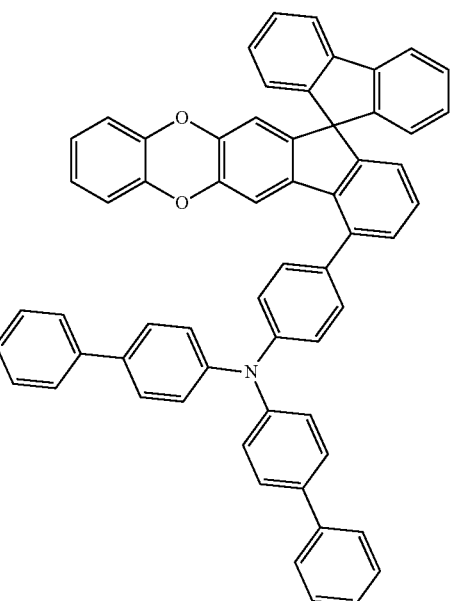
Cpd 162
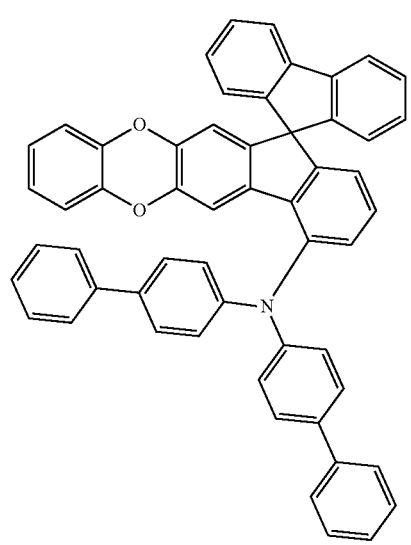
Cpd 163
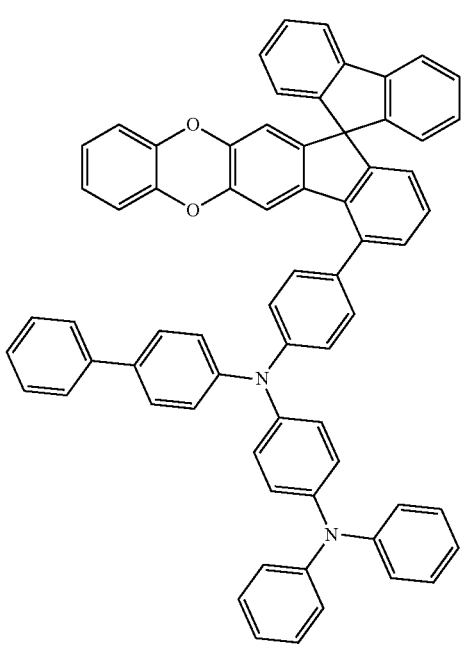

-continued
Cpd 164
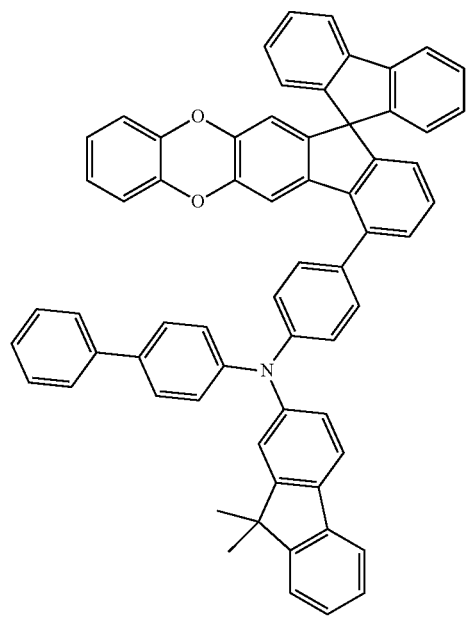
Cpd 165
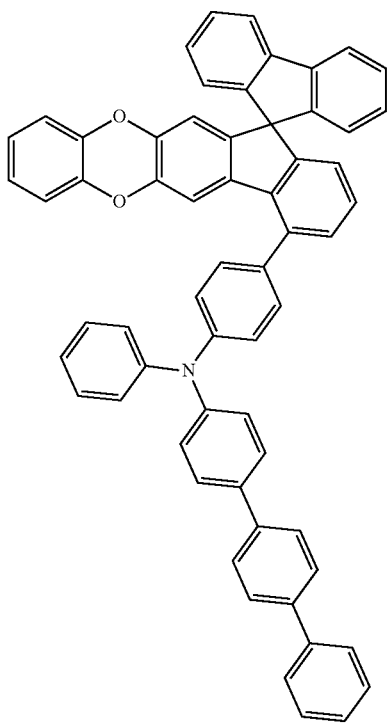
Cpd 166
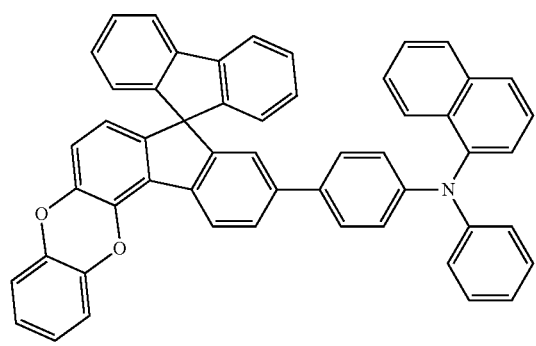
Cpd 167
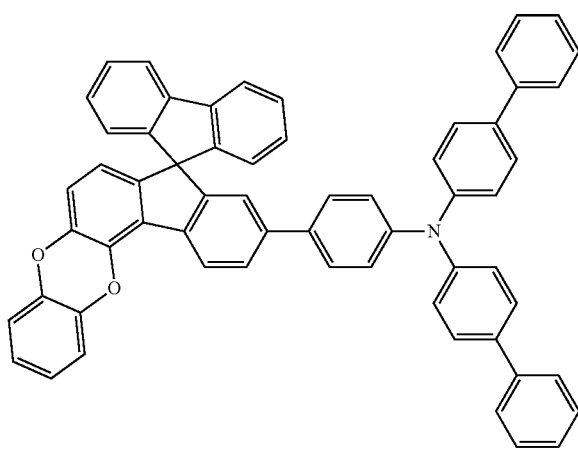
Cpd 168
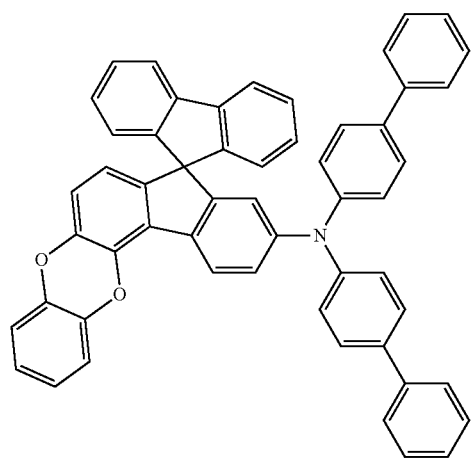
Cpd 169
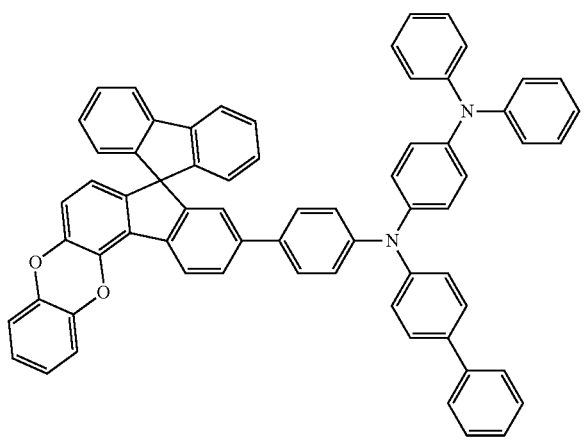

-continued
Cpd 170
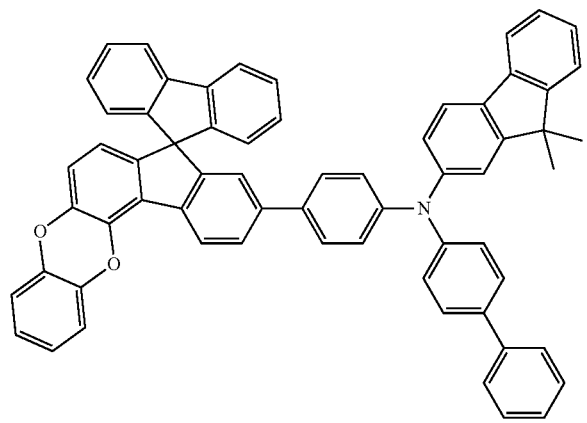
Cpd 171
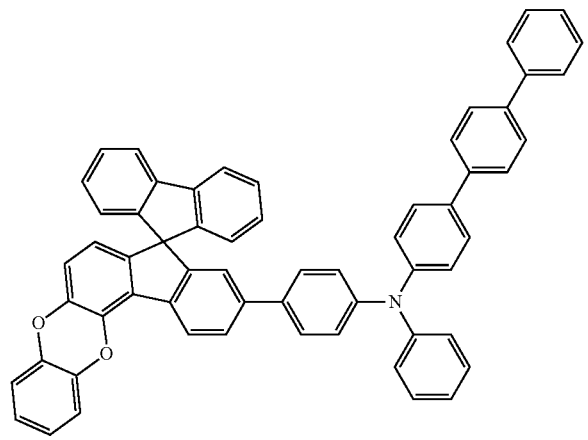
Cpd 172
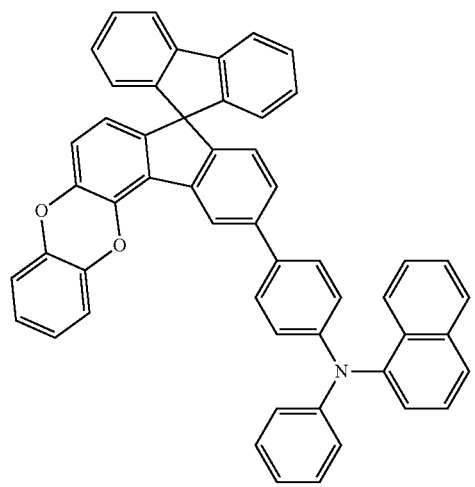
Cpd 173
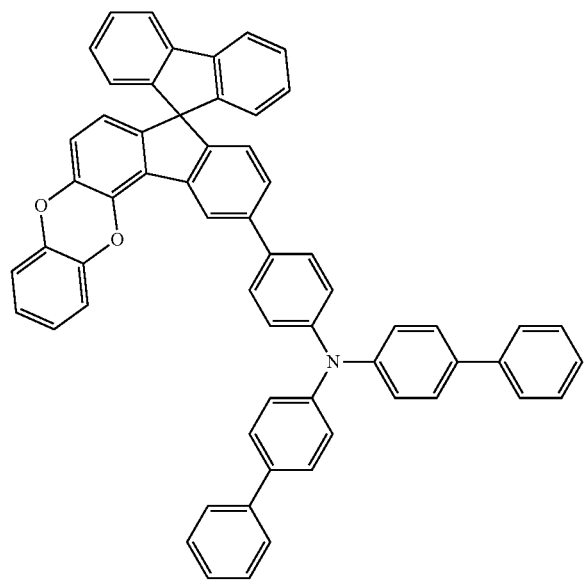
Cpd 174
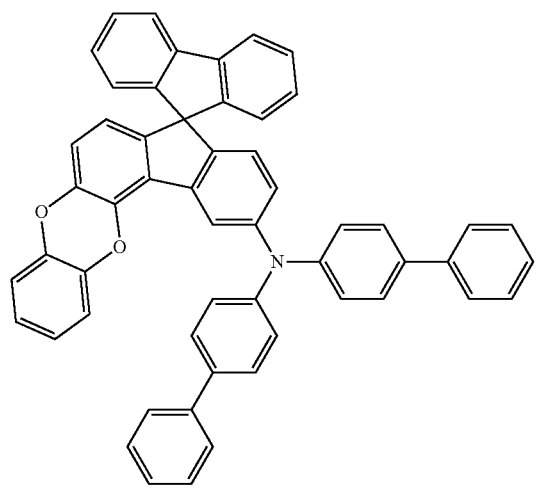
Cpd 175
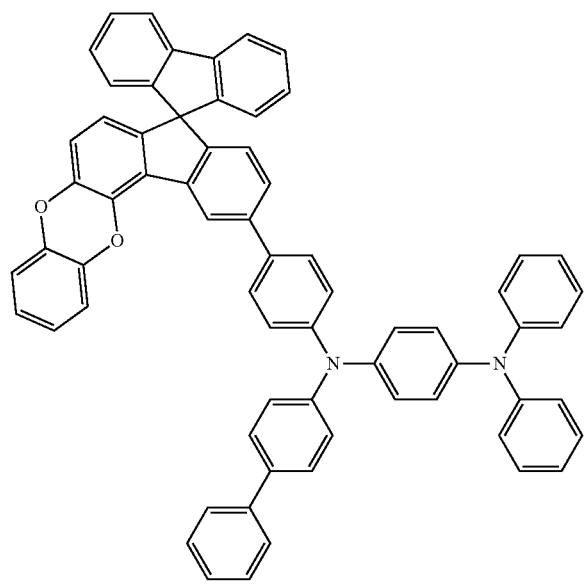

-continued
Cpd 176
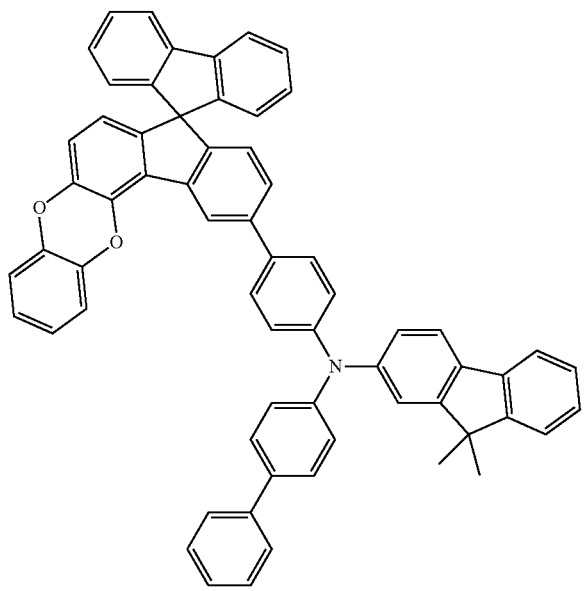
Cpd 177
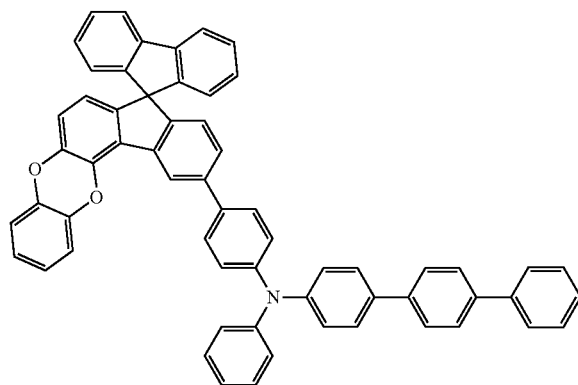
Cpd 178
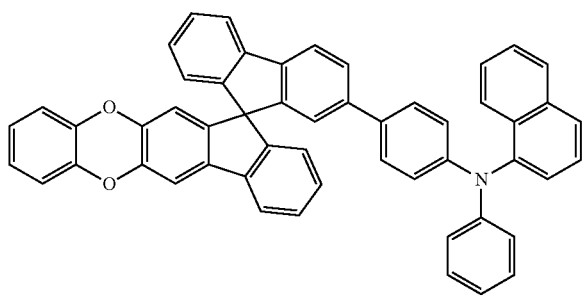
Cpd 179
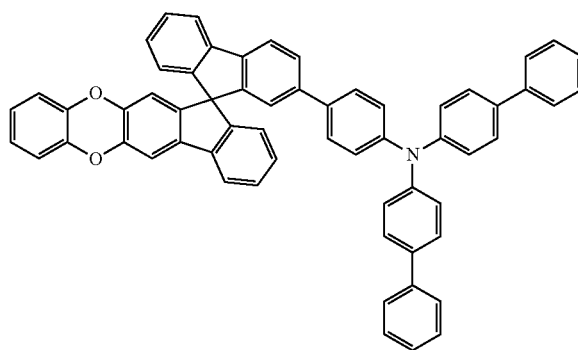
Cpd 180
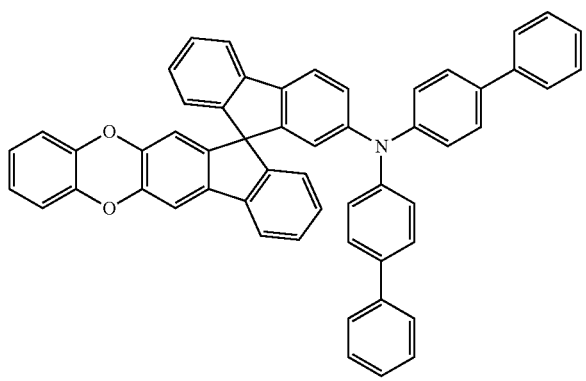

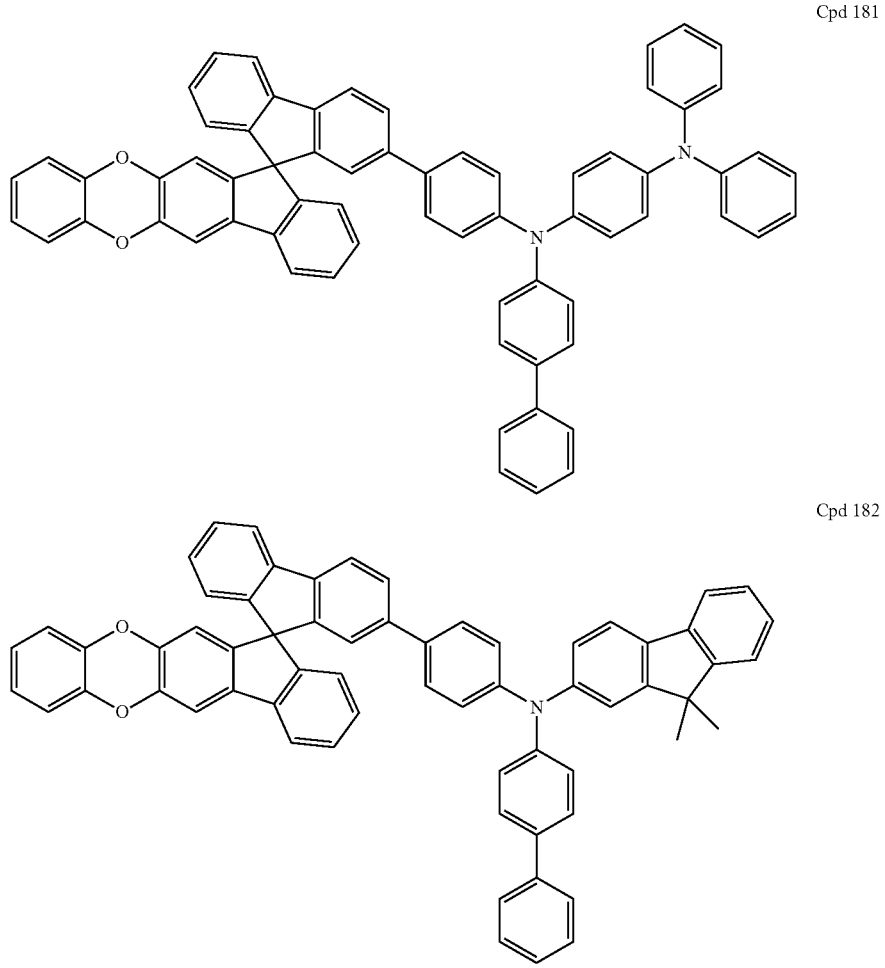

Cpd 181

Cpd 182

In the present disclosure, the compound represented by Chemical Formula 1 may be synthesized using general synthesis methods (refer to Chem. Rev., 60:313 (1960); J. Chem. SOC. 4482 (1955); Chem. Rev. 95: 2457 (1995) or the like). Detailed synthesis processes for the compounds of the present disclosure will be specifically described in synthesis examples to be described later.

2. Organic Electroluminescent Device

Meanwhile, another aspect of the present disclosure relates to an organic electroluminescent device (organic EL device) including the compound represented by Chemical Formula 1 according to the present disclosure.

Specifically, the present disclosure relates to an organic electroluminescent device including an anode, a cathode, and one or more organic material layers provided between the anode and the cathode, and at least one of the one or more organic material layers includes the compound represented by Chemical Formula 1. Herein, the compound may be used either alone or as a mixture of two or more.

The one or more organic material layers may be any one or more of a hole injection layer, a hole transport layer, a light emitting layer, an auxiliary light emitting layer, a lifetime improving layer, an electron transport layer, an auxiliary electron transport layer and an electron injection layer, and at least one organic material layer among these may include the compound represented by Chemical Formula 1. Preferably, the organic material layer including the compound represented by Chemical Formula 1 may be a light emitting layer or an auxiliary light emitting layer.

According to one embodiment of the present disclosure, the light emitting layer of the organic electroluminescent device may include a host material, and herein, the compound represented by Chemical Formula 1 may be included as the host material. Like this, when including the compound represented by Chemical Formula 1 as a light emitting layer material, preferably, as a green phosphorescent host of the organic electroluminescent device, binding strength of holes and electrons increases in the light emitting layer, and therefore, efficiency (light emission efficiency and power efficiency), lifetime, luminescence, driving voltage and the like of the organic electroluminescent device may be enhanced.

The structure of the organic electroluminescent device according to the present disclosure described above is not particularly limited, and for example, may have a structure in which a substrate, an anode, a hole injection layer, a hole transport layer, a light emitting layer, an electron transport layer and a cathode are consecutively laminated. Herein, an auxiliary electron transport layer may be further laminated between the light emitting layer and the electron transport layer, and an electron injection layer may be further laminated on the electron transport layer. In the present disclosure, one or more of the hole injection layer, the hole transport layer, the light emitting layer, the electron transport layer, the auxiliary electron transport layer and the electron injection layer may include the compound represented by Chemical Formula 1, and preferably, the light emitting layer or the auxiliary light emitting layer may include the compound represented by Chemical Formula 1.

In addition, the organic electroluminescent device of the present disclosure may have a structure in which an anode, one or more organic material layers and a cathode are consecutively laminated, and in addition thereto, may have a structure in which an insulating layer or an adhesive layer is inserted at an interface between the electrode and the organic material layer.

Except that at least one or more of the organic material layers (for example, light emitting layer or auxiliary light emitting layer) is formed to include the compound represented by Chemical Formula 1, the organic electroluminescent device of the present disclosure may be manufactured by forming other organic material layers and electrodes using materials and methods known in the art.

The organic material layer may be formed using a vacuum deposition method or a solution coating method. Examples of the solution coating method may include spin coating, dip coating, doctor blading, inkjet printing, thermal transfer method or the like, but are not limited thereto.

A substrate capable of being used in the present disclosure is not particularly limited, and silicon wafers, quartz, glass plates, metal plates, plastic films, sheets and the like may be used.

Examples of the anode material may include metals such as vanadium, chromium, copper, zinc or gold, or alloys thereof; metal oxides such as zinc oxide, indium oxide, indium tin oxide (ITO) or indium zinc oxide (IZO); combinations of metals and oxides such as ZnO:Al or $SnO_2$:Sb; conductive polymers such as polythiophene, poly(3-methylthiophene), poly[3,4-(ethylene-1,2-dioxy)thiophene] (PEDT), polypyrrole or polyaniline; carbon black, and the like, but are not limited thereto.

Examples of the cathode material may include metals such as magnesium, calcium, sodium, potassium, titanium, indium, yttrium, lithium, gadolinium, aluminum, silver, tin or lead, or alloys thereof; and multilayer-structured materials such as LiF/Al or $LiO_2$/Al, but are not limited thereto.

Hereinafter, the present disclosure will be described in detail with reference to examples as follows. However, the following examples are for illustrative purposes only, and the present disclosure is not limited to the following examples.

[Preparation Example 1] Synthesis of Compound Inv1

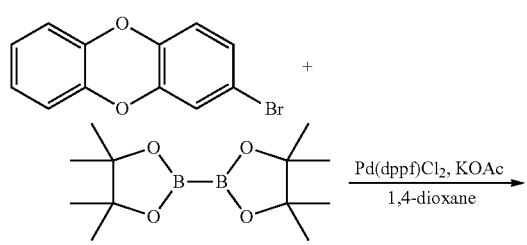

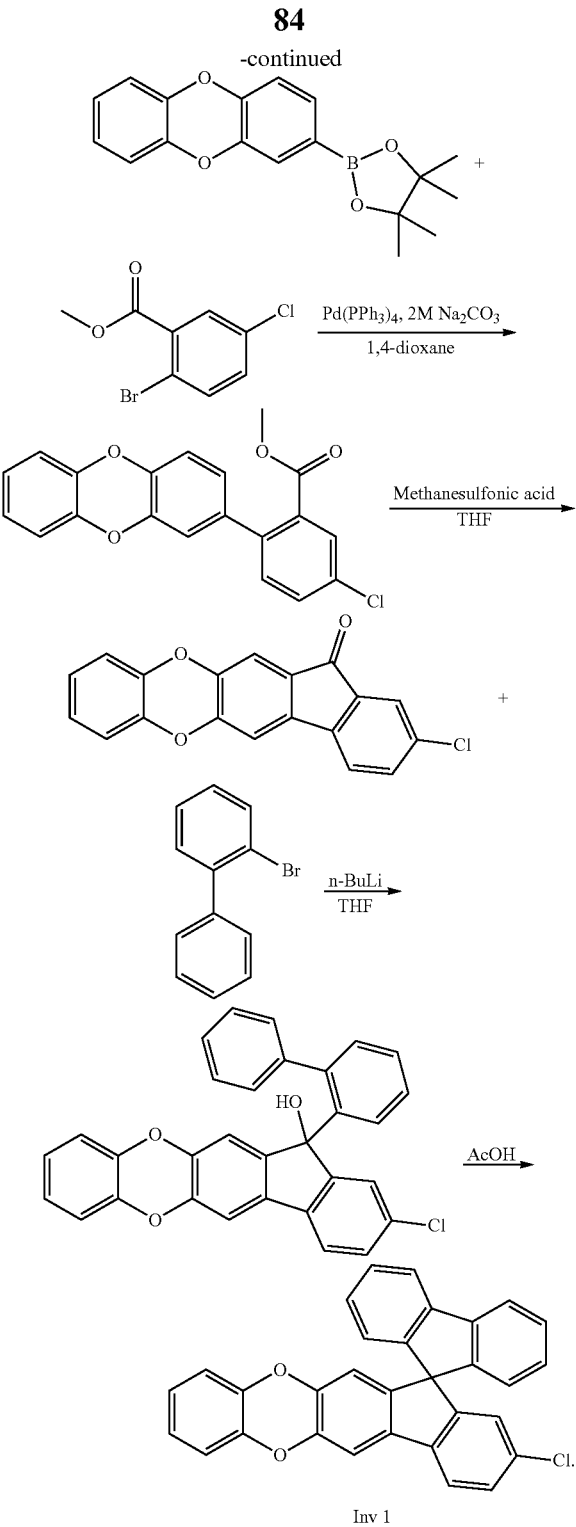

Inv 1

<Step 1> Synthesis of 2-(dibenzo[b,e][1,4]dioxin-2-yl)-4,4,5,5-tetramethyl-1,3,2-dioxaborolane 2-Bromodibenzo[b,e][1,4]dioxine (100 g, 0.38 mol), bis(pinacolato)diborone (115.8 g, 0.46 mol), Pd(dppf)Cl$_2$ (31 g, 0.038 mol) and KOAc (111.9 g, 1.14 mol) were placed in a flask, then dissolved by introducing 1,4-dioxane (2 L) thereto, and the result was heated and stirred for 8 hours.

After the reaction was terminated, distilled water was introduced thereto, and the organic layer was extracted with ethyl acetate. The obtained organic layer was dried using Na₂SO₄, vacuum distilled, and then purified using column chromatography to obtain a 2-(dibenzo[b,e][1,4]dioxin-2-yl)-4,4,5,5-tetramethyl-1,3,2-dioxaborolane compound (73 g, yield 62%).

<Step 2> Synthesis of methyl 5-chloro-2-(dibenzo[b,e][1,4]dioxin-2-yl)benzoate

The 2-(dibenzo[b,e][1,4]dioxin-2-yl)-4,4,5,5-tetramethyl-1,3,2-dioxaborolane (73 g, 0.235 mol) obtained in <Step 1>, methyl 2-bromo-5-chlorobenzoate (70.3 g, 0.282 mol) and Pd(PPh₃)₄ (13.5 g, 0.011 mol) were placed in a flask, and dissolved by adding a saturated aqueous 2 M Na₂CO₃ solution (352 ml) and 1,4-dioxane (2 L) thereto, and then the result was heated and stirred for 8 hours. After the reaction was terminated, distilled water was introduced thereto, and the organic layer was extracted with ethyl acetate. The obtained organic layer was dried using Na₂SO₄, vacuum distilled, and then purified using column chromatography to obtain a methyl 5-chloro-2-(dibenzo[b,e][1,4]dioxin-2-yl)benzoate compound (75.4 g, yield 91%).

<Step 3> Synthesis of 9-chloro-11H-benzo[b]fluoreno[2,3-e][1,4]dioxin-11-one

After introducing the methyl 5-chloro-2-(dibenzo[b,e][1,4]dioxin-2-yl)benzoate (75.4 g, 0.214 mol) obtained in <Step 2> to THF (1 L) and heating the result, methanesulfonic acid (350 ml) was added thereto, and the result was stirred for 4 hours. Water (500 ml) was added thereto, and produced solids were filtered, washed with water (600 ml) and ethanol (200 ml), and dried to obtain a 9-chloro-11H-benzo[b]fluoreno[2,3-e][1,4]dioxin-11-one compound (53.0 g, yield 78%).

<Step 4> Synthesis of 11-([1,1'-biphenyl]-2-yl)-9-chloro-11H-benzo[b]fluoreno[2,3-e][1,4]dioxin-11-ol After dissolving 2-bromo-1,1'-biphenyl (30 ml, 174.0 mmol) in anhydrous THF (500 ml), the result was cooled to −78□, then 2.5 M n-BuLi (73.2 ml, 183 mmol) was slowly added thereto, and the result was stirred for 1 hour. To this reaction solution, the 9-chloro-11H-benzo[b]fluoreno[2,3-e][1,4]dioxin-11-one (53.0 g, 165.4 mmol) obtained in <Step 3> was added, and then the result was stirred for 3 hours while slowly raising the temperature to room temperature. After terminating the reaction by adding an aqueous ammonium chloride solution thereto, distilled water was added thereto, and the organic layer was extracted with ethyl acetate. The obtained organic layer was dried using Na₂SO₄, vacuum distilled, and then purified using column chromatography to obtain a 11-([1,1'-biphenyl]-2-yl)-9-chloro-11H-benzo[b]fluoreno[2,3-e][1,4]dioxin-11-ol compound (62.8 g, yield 80%).

<Step 5> Synthesis of Compound Inv1

After introducing the 11-([1,1'-biphenyl]-2-yl)-9-chloro-11H-benzo[b]fluoreno[2,3-e][1,4]dioxin-11-ol (62.8 g, 132.3 mmol) obtained in <Step 4> to AcOH (400 ml) and heating the result, sulfuric acid (0.1 ml) was added thereto, and the result was heated and stirred for 1 hour. After lowering the temperature to room temperature, produced solids were filtered, washed with water (600 ml) and ethanol (200 ml), and then dried to obtain Compound Inv1 (58.6 g, yield 93%).

[Preparation Example 2] Synthesis of Compound Inv2

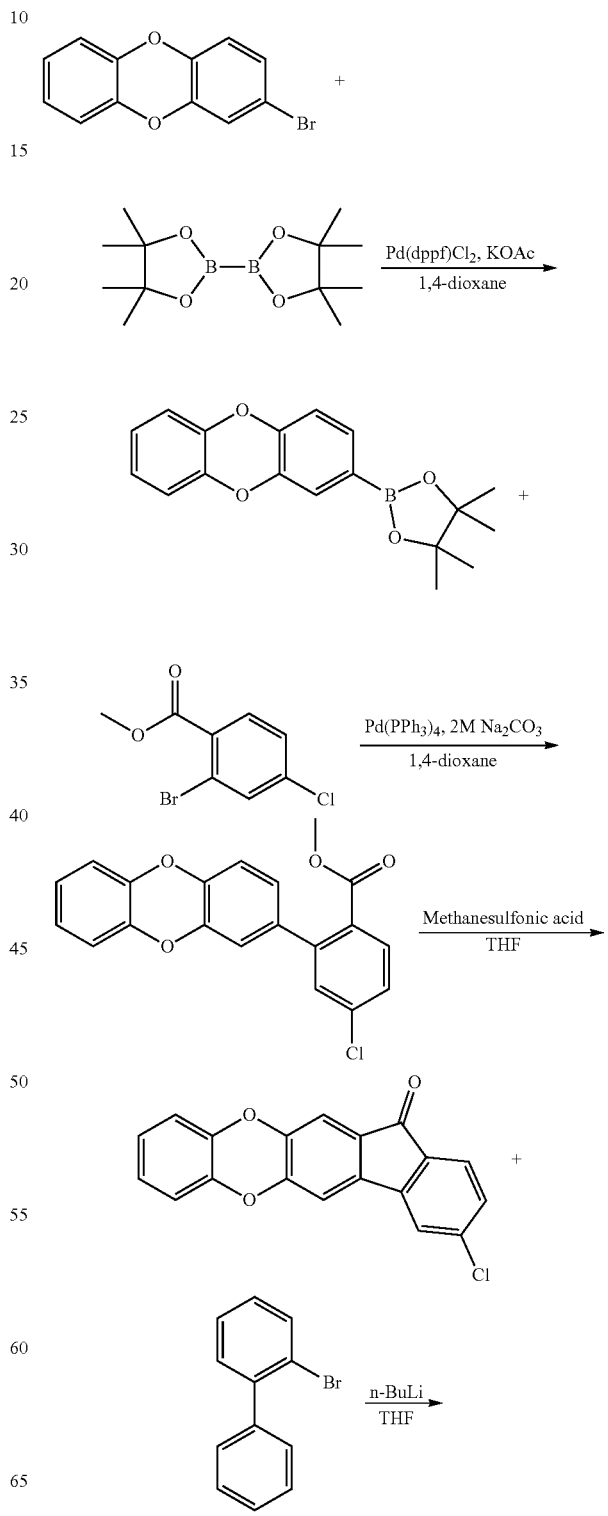

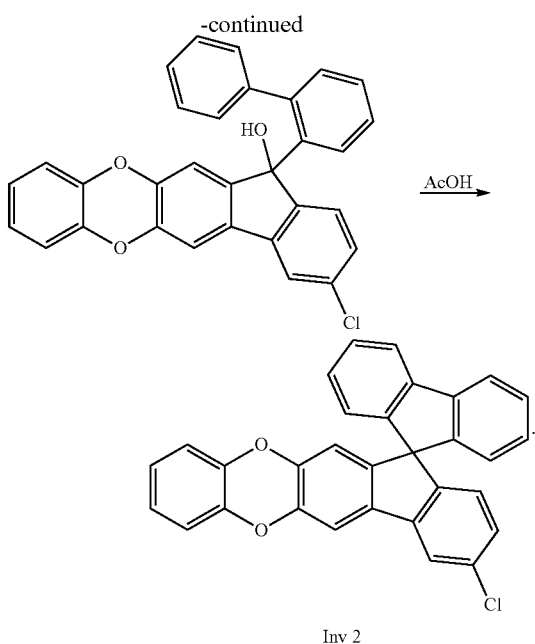

Inv 2

<Step 1> Synthesis of 2-(dibenzo[b,e][1,4]dioxin-2-yl)-4,4,5,5-tetramethyl-1,3,2-dioxaborolane 2-Bromodibenzo[b,e][1,4]dioxine (100 g, 0.38 mol), bis(pinacolato)diborone (115.8 g, 0.46 mol), Pd(dppf)Cl$_2$ (31 g, 0.038 mol) and KOAc (111.9 g, 1.14 mol) were placed in a flask, then dissolved by introducing 1,4-dioxane (2 L) thereto, and the result was heated and stirred for 8 hours. After the reaction was terminated, distilled water was introduced thereto, and the organic layer was extracted with ethyl acetate. The obtained organic layer was dried using Na$_2$SO$_4$, vacuum distilled, and then purified using column chromatography to obtain a 2-(dibenzo[b,e][1,4]dioxin-2-yl)-4,4,5,5-tetramethyl-1,3,2-dioxaborolane compound (73 g, yield 62%).

<Step 2> Synthesis of methyl 4-chloro-2-(dibenzo[b,e][1,4]dioxin-2-yl)benzoate The 2-(dibenzo[b,e][1,4]dioxin-2-yl)-4,4,5,5-tetramethyl-1,3,2-dioxaborolane (73 g, 0.235 mol) obtained in <Step 1>, methyl 2-bromo-4-chlorobenzoate (70.3 g, 0.282 mol) and Pd(PPh$_3$)$_4$ (13.5 g, 0.011 mol) were placed in a flask, and dissolved by adding a saturated aqueous 2 M Na$_2$CO$_3$ solution (352 ml) and 1,4-dioxane (2 L) thereto, and then the result was heated and stirred for 8 hours. After the reaction was terminated, distilled water was introduced thereto, and the organic layer was extracted with ethyl acetate. The obtained organic layer was dried using Na$_2$SO$_4$, vacuum distilled, and then purified using column chromatography to obtain a methyl 4-chloro-2-(dibenzo[b,e][1,4]dioxin-2-yl)benzoate compound (75.4 g, yield 91%).

<Step 3> Synthesis of 8-chloro-11H-benzo[b]fluoreno[2,3-e][1,4]dioxin-11-one After introducing the methyl 4-chloro-2-(dibenzo[b,e][1,4]dioxin-2-yl)benzoate (75.4 g, 0.214 mol) obtained in <Step 2> to THF (1 L) and heating the result, methanesulfonic acid (350 ml) was added thereto, and the result was stirred for 4 hours. Water (500 ml) was added thereto, and produced solids were filtered, washed with water (600 ml) and ethanol (200 ml), and dried to obtain a 8-chloro-11H-benzo[b]fluoreno[2,3-e][1,4]dioxin-11-one compound (53.0 g, yield 78%).

<Step 4> Synthesis of 11-([1,1'-biphenyl]-2-yl)-8-chloro-11H-benzo[b]fluoreno[2,3-e][1,4]dioxin-11-ol After dissolving 2-bromo-1,1'-biphenyl (30 ml, 174.0 mmol) in anhydrous THF (500 ml), the result was cooled to −78□, then 2.5 M n-BuLi (73.2 ml, 183 mmol) was slowly added thereto, and the result was stirred for 1 hour. To this reaction solution, the 8-chloro-11H-benzo[b]fluoreno[2,3-e][1,4]dioxin-11-one (53.0 g, 165.4 mmol) obtained in <Step 3> was added, and then the result was stirred for 3 hours while slowly raising the temperature to room temperature. After terminating the reaction by adding an aqueous ammonium chloride solution thereto, distilled water was added thereto, and the organic layer was extracted with ethyl acetate. The obtained organic layer was dried using Na$_2$SO$_4$, vacuum distilled, and then purified using column chromatography to obtain a 11-([1,1'-biphenyl]-2-yl)-8-chloro-11H-benzo[b]fluoreno[2,3-e][1,4]dioxin-11-ol compound (62.8 g, yield 80%).

<Step 5> Synthesis of Compound Inv2

After introducing the 11-([1,1'-biphenyl]-2-yl)-8-chloro-11H-benzo[b]fluoreno[2,3-e][1,4]dioxin-11-ol (62.8 g, 132.3 mmol) obtained in <Step 4> to AcOH (400 ml) and heating the result, sulfuric acid (0.1 ml) was added thereto, and the result was heated and stirred for 1 hour. After lowering the temperature to room temperature, produced solids were filtered, washed with water (600 ml) and ethanol (200 ml), and then dried to obtain Compound Inv2 (58.6 g, yield 93%).

[Preparation Example 3] Synthesis of Compound Inv3

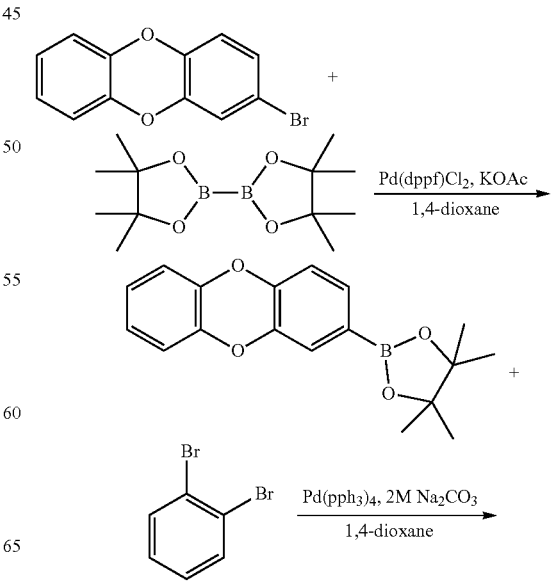

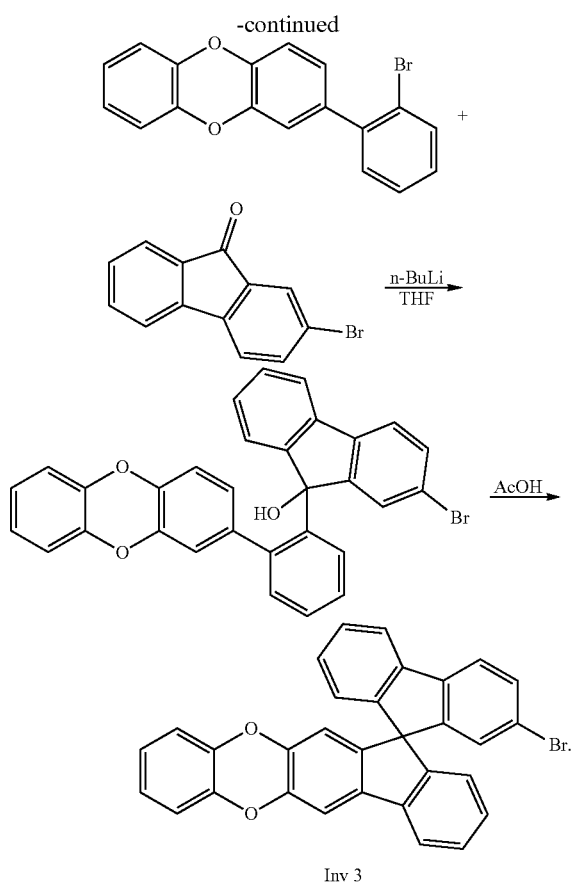

Inv 3

<Step 1> Synthesis of 2-(dibenzo[b,e][1,4]dioxin-2-yl)-4,4,5,5-tetramethyl-1,3,2-dioxaborolane 2-Bromodibenzo[b,e][1,4]dioxine (100 g, 0.38 mol), bis(pinacolato)diborone (115.8 g, 0.46 mol), Pd(dppf)Cl$_2$ (31 g, 0.038 mol) and KOAc (111.9 g, 1.14 mol) were placed in a flask, then dissolved by introducing 1,4-dioxane (2 L) thereto, and the result was heated and stirred for 8 hours. After the reaction was terminated, distilled water was introduced thereto, and the organic layer was extracted with ethyl acetate. The obtained organic layer was dried using Na$_2$SO$_4$, vacuum distilled, and then purified using column chromatography to obtain a 2-(dibenzo[b,e][1,4]dioxin-2-yl)-4,4,5,5-tetramethyl-1,3,2-dioxaborolane compound (73 g, yield 62%).

<Step 2> Synthesis of 2-(2-bromophenyl)dibenzo[b,e][1,4]dioxine

The 2-(dibenzo[b,e][1,4]dioxin-2-yl)-4,4,5,5-tetramethyl-1,3,2-dioxaborolane (73 g, 0.235 mol) obtained in <Step 1>, 1,2-dibromobenzene (111 g, 0.470 mol) and Pd(PPh$_3$)$_4$ (13.5 g, 0.011 mol) were placed in a flask, and dissolved by adding a saturated aqueous 2 M Na$_2$CO$_3$ solution (352 ml) and 1,4-dioxane (2 L) thereto, and then the result was heated and stirred for 8 hours. After the reaction was terminated, distilled water was introduced thereto, and the organic layer was extracted with ethyl acetate. The obtained organic layer was dried using Na$_2$SO$_4$, vacuum distilled, and then purified using column chromatography to obtain a 2-(2-bromophenyl)dibenzo[b,e][1,4]dioxine compound (72.5 g, yield 91%).

<Step 3> Synthesis of 2-bromo-9-(2-(dibenzo[b,e][1,4]dioxin-2-yl)phenyl)-9H-fluoren-9-ol After dissolving the 2-(2-bromophenyl)dibenzo[b,e][1,4]dioxine (59 g, 0.174 mol) obtained in <Step 2> in anhydrous THF (500 ml), the result was cooled to −78□, then 2.5 M n-BuLi (73.2 ml, 183 mmol) was slowly added thereto, and the result was stirred for 1 hour. To this reaction solution, 2-bromo-9H-fluoren-9-one (43.0 g, 0.166 mol) was added, and then the result was stirred for 3 hours while slowly raising the temperature to room temperature. After terminating the reaction by adding an aqueous ammonium chloride solution thereto, distilled water was added thereto, and the organic layer was extracted with ethyl acetate. The obtained organic layer was dried using Na$_2$SO$_4$, vacuum distilled, and then purified using column chromatography to obtain a 2-bromo-9-(2-(dibenzo[b,e][1,4]dioxin-2-yl)phenyl)-9H-fluoren-9-ol compound (68.7 g, yield 80%).

<Step 4> Synthesis of Compound Inv3

After introducing the 2-bromo-9-(2-(dibenzo[b,e][1,4]dioxin-2-yl)phenyl)-9H-fluoren-9-ol (68.7 g, 132.3 mmol) obtained in <Step 3> to AcOH (400 ml) and heating the result, sulfuric acid (0.1 ml) was added thereto, and the result was heated and stirred for 1 hour. After lowering the temperature to room temperature, produced solids were filtered, washed with water (600 ml) and ethanol (200 ml), and then dried to obtain Compound Inv3 (61.7 g, yield 93%).

[Synthesis Example 1] Synthesis of Cpd50

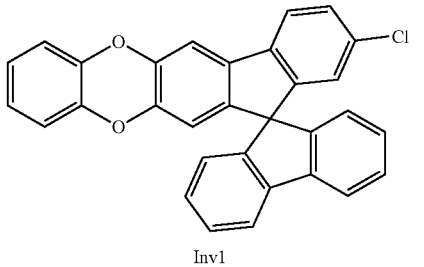

Inv1

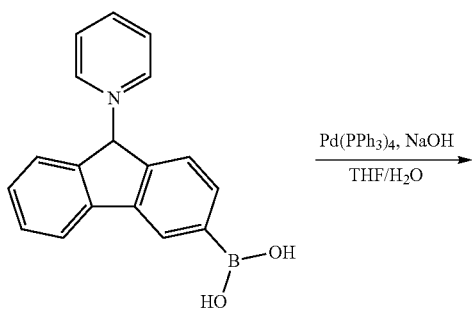

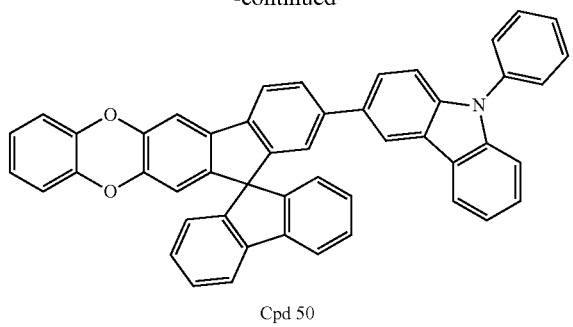

Cpd 50

Inv 1 (3.5 g, 7.70 mmol) obtained in Preparation Example 1, (9-phenyl-9H-carbazol-3-yl)boronic acid (2.8 g, 9.67 mmol), NaOH (1.06 g, 26.4 mmol) and THF/H$_2$O (100 m/150 ml) were introduced and stirred. After that, Pd(PPh$_3$)$_4$ (5 mol %, 0.51 g) was introduced thereto at 40□, and the result was stirred for 12 hours at 80□.

After checking that the reaction was terminated using TLC, the result was cooled to room temperature. After the reaction was terminated, distilled water was added thereto, and the organic layer was extracted with ethyl acetate. The obtained organic layer was dried using Na$_2$SO$_4$, vacuum distilled, and then purified using column chromatography to obtain Compound Cpd50 (4.1 g, yield 80%).

HRMS [M]$^+$: 663.220

[Synthesis Example 2] Synthesis of Cpd51

Target Compound Cpd51 was obtained in the same manner as in Synthesis Example 1 except that dibenzo[b,d]furan-4-ylboronic acid was used instead of (9-phenyl-9H-carbazol-3-yl)boronic acid.

HRMS [M]$^+$: 588.173

[Synthesis Example 3] Synthesis of Cpd52

Target Compound Cpd52 was obtained in the same manner as in Synthesis Example 1 except that dibenzo[b,d]thiophen-4-ylboronic acid was used instead of (9-phenyl-9H-carbazol-3-yl)boronic acid.

HRMS [M]$^+$: 604.150

[Synthesis Example 4] Synthesis of Cpd53

Target Compound Cpd53 was obtained in the same manner as in Synthesis Example 1 except that dibenzo[b,d]furan-2-ylboronic acid was used instead of (9-phenyl-9H-carbazol-3-yl)boronic acid.

HRMS [M]$^+$: 588.173

[Synthesis Example 5] Synthesis of Cpd54

Target Compound Cpd54 was obtained in the same manner as in Synthesis Example 1 except that dibenzo[b,d]thiophen-2-ylboronic acid was used instead of (9-phenyl-9H-carbazol-3-yl)boronic acid.

HRMS [M]$^+$: 604.150

[Synthesis Example 6] Synthesis of Cpd77

Target Compound Cpd77 was obtained in the same manner as in Synthesis Example 1 except that (3-(4,6-diphenyl-1,3,5-triazin-2-yl)phenyl)boronic acid was used instead of (9-phenyl-9H-carbazol-3-yl)boronic acid.

HRMS [M]$^+$: 729.242

[Synthesis Example 7] Synthesis of Cpd83

Target Compound Cpd83 was obtained in the same manner as in Synthesis Example 1 except that (9-(4,6-diphenyl-1,3,5-triazin-2-yl)-9H-carbazol-3-yl)boronic acid was used instead of (9-phenyl-9H-carbazol-3-yl)boronic acid.

HRMS [M]$^+$: 818.268

[Synthesis Example 8] Synthesis of Cpd92

Target Compound Cpd92 was obtained in the same manner as in Synthesis Example 1 except that (9-(3-(4,6-diphenyl-1,3,5-triazin-2-yl)phenyl)-9H-carbazol-3-yl)boronic acid was used instead of (9-phenyl-9H-carbazol-3-yl)boronic acid.

HRMS [M]$^+$: 894.299

[Synthesis Example 9] Synthesis of Cpd95

Target Compound Cpd95 was obtained in the same manner as in Synthesis Example 1 except that (9-(4'-(4,6-diphenyl-1,3,5-triazin-2-yl)-[1,1'-biphenyl]-4-yl)-9H-carbazol-3-yl)boronic acid was used instead of (9-phenyl-9H-carbazol-3-yl)boronic acid.

HRMS [M]$^+$: 970.331

[Synthesis Example 10] Synthesis of Cpd96

Target Compound Cpd96 was obtained in the same manner as in Synthesis Example 1 except that (9-(3'-(4,6-diphenyl-1,3,5-triazin-2-yl)-[1,1'-biphenyl]-4-yl)-9H-carbazol-3-yl)boronic acid was used instead of (9-phenyl-9H-carbazol-3-yl)boronic acid.

HRMS [M]$^+$: 970.331

[Synthesis Example 11] Synthesis of Cpd97

Target Compound Cpd97 was obtained in the same manner as in Synthesis Example 1 except that (9-(4'-(4,6-diphenyl-1,3,5-triazin-2-yl)-[1,1'-biphenyl]-3-yl)-9H-carbazol-3-yl)boronic acid was used instead of (9-phenyl-9H-carbazol-3-yl)boronic acid.

HRMS [M]$^+$: 970.331

[Synthesis Example 12] Synthesis of Cpd98

Target Compound Cpd98 was obtained in the same manner as in Synthesis Example 1 except that (9-(3'-(4,6-diphenyl-1,3,5-triazin-2-yl)-[1,1'-biphenyl]-3-yl)-9H-carbazol-3-yl)boronic acid was used instead of (9-phenyl-9H-carbazol-3-yl)boronic acid.

HRMS [M]$^+$: 970.331

[Synthesis Example 13] Synthesis of Cpd148

Target Compound Cpd148 was obtained in the same manner as in Synthesis Example 1 except that (4-(naphthalen-1-yl(phenyl)amino)phenyl)boronic acid was used instead of (9-phenyl-9H-carbazol-3-yl)boronic acid.

HRMS [M]$^+$: 715.251

[Synthesis Example 14] Synthesis of Cpd149

Target Compound Cpd149 was obtained in the same manner as in Synthesis Example 1 except that (4-(di([1,1'- biphenyl]-4-yl)amino)phenyl)boronic acid was used instead of (9-phenyl-9H-carbazol-3-yl)boronic acid.

HRMS [M]⁺: 817.298

[Synthesis Example 15] Synthesis of Cpd152

Target Compound Cpd152 was obtained in the same manner as in Synthesis Example 1 except that (4-([1,1'-biphenyl]-4-yl(9,9-dimethyl-9H-fluoren-2-yl)amino)phenyl)boronic acid was used instead of (9-phenyl-9H-carbazol-3-yl)boronic acid.

HRMS [M]⁺: 857.329

[Synthesis Example 16] Synthesis of Cpd154

Target Compound Cpd154 was obtained in the same manner as in Synthesis Example 1 except that (4-(naphthalen-1-yl(phenyl)amino)phenyl)boronic acid was used instead of (9-phenyl-9H-carbazol-3-yl)boronic acid.

HRMS [M]⁺: 715.251

[Synthesis Example 17] Synthesis of Cpd155

Target Compound Cpd155 was obtained in the same manner as in Synthesis Example 1 except that (4-(di([1,1'-biphenyl]-4-yl)amino)phenyl)boronic acid was used instead of (9-phenyl-9H-carbazol-3-yl)boronic acid.

HRMS [M]⁺: 817.298

[Synthesis Example 18] Synthesis of Cpd158

Target Compound Cpd158 was obtained in the same manner as in Synthesis Example 1 except that (4-([1,1'-biphenyl]-4-yl(9,9-dimethyl-9H-fluoren-2-yl)amino)phenyl)boronic acid was used instead of (9-phenyl-9H-carbazol-3-yl)boronic acid.

HRMS [M]⁺: 857.329

[Synthesis Example 19] Synthesis of Cpd179

Target Compound Cpd179 was obtained in the same manner as in Synthesis Example 1 except that (4-(di([1,1'-biphenyl]-4-yl)amino)phenyl)boronic acid was used instead of (9-phenyl-9H-carbazol-3-yl)boronic acid.

HRMS [M]⁺: 817.298

[Synthesis Example 20] Synthesis of Cpd150

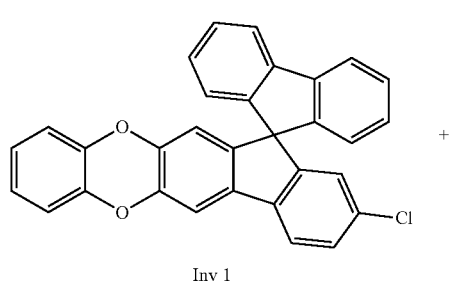

Inv 1

+

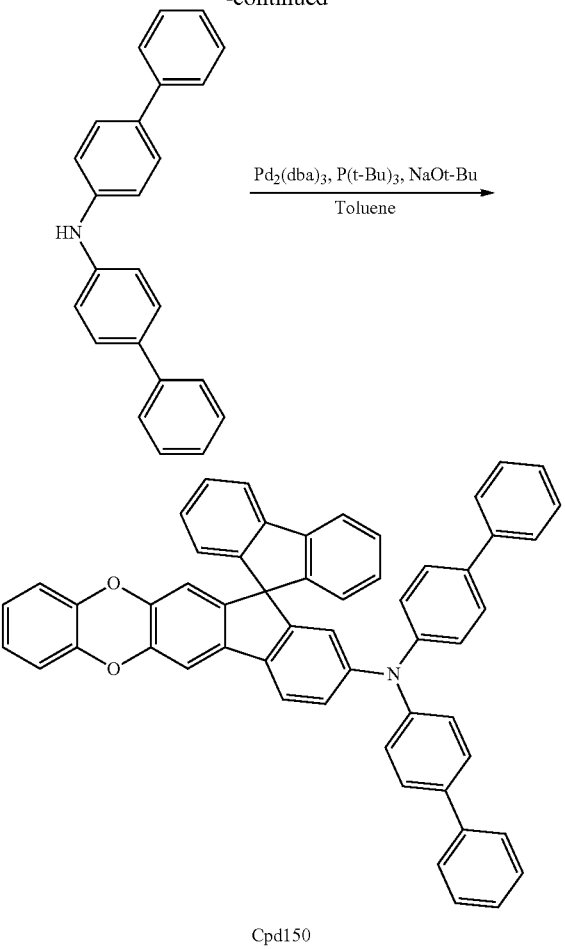

Cpd150

After dissolving Inv 1 (4.6 g, 10.0 mmol) and di([1,1'-biphenyl]-4-yl)amine (3.8 g, 12.0 mmol) in toluene (100 ml), Pd₂(dba)₃ (0.9 g, 1.0 mmol) was introduced thereto under nitrogen. After that, NaOtBu (2.9 g, 30 mmol) was introduced thereto, (t-Bu)₃P (1.0 ml, 1.0 mmol) was introduced to the reaction solution, and then the mixture was stirred under reflux for 5 hours.

After checking that the reaction was terminated using TLC, the result was cooled to room temperature. After the reaction was terminated, distilled water was added thereto, and the result was extracted with ethyl acetate. The obtained organic layer was dried using Na₂SO₄, vacuum distilled, and then purified using column chromatography to obtain Compound Cpd150 (6.4 g, yield 86%).

HRMS [M]⁺: 741.267

[Synthesis Example 21] Synthesis of Cpd156

Target Compound Cpd156 was obtained in the same manner as in Synthesis Example 20 except that Inv2 was used instead of Inv1.

HRMS [M]⁺: 741.267

[Synthesis Example 22] Synthesis of Cpd180

Target Compound Cpd180 was obtained in the same manner as in Synthesis Example 20 except that Inv3 was used instead of Inv1.

HRMS [M]⁺: 741.267

[Example 1] Manufacture of Green Organic Electroluminescent Device

After high purity sublimation purifying Compound Cpd148 synthesized in Synthesis Example 13 using a commonly known method, a green organic electroluminescent device was manufactured as follows.

A glass substrate on which indium tin oxide (ITO) was coated as a thin film to a thickness of 1500 Å was distilled water ultrasonic cleaned. After the distilled water cleaning was finished, the substrate was ultrasonic cleaned with solvents such as isopropyl alcohol, acetone and methanol, dried, then transferred to a UV OZONE washer (Power sonic 405, manufactured by Hwashin Tech. Co., Ltd.), and then, after cleaning the substrate for 5 minutes using UV, the substrate was transferred to a vacuum depositor.

On the transparent ITO electrode prepared as above, m-MTDATA (60 nm)/TCTA (80 nm)/Compound cpd148 (40 nm)/CBP+10% Ir(ppy)$_3$ (300 nm)/BCP (10 nm)/Alq$_3$ (30 nm)/LiF (1 nm)/Al (200 nm) were laminated in this order to manufacture a green organic electroluminescent device.

Structures of the m-MTDATA, the TCTA, the Ir(ppy)$_3$, the CBP and the BCP used herein are as follows.

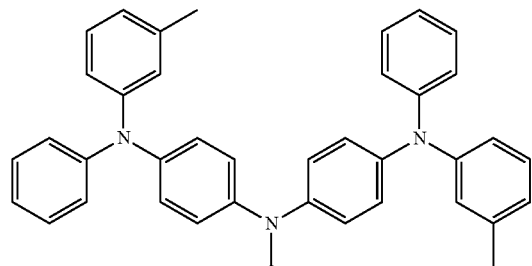

m-MTDATA

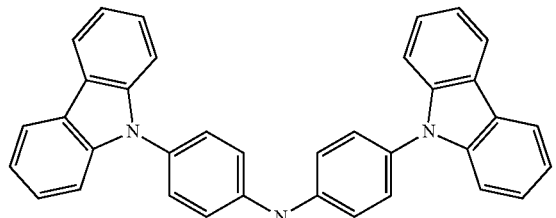

TCTA

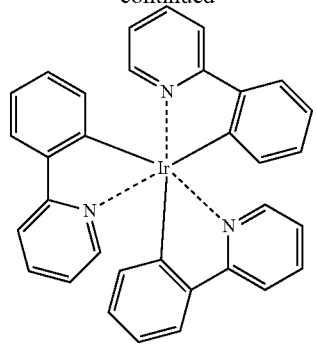

Ir(ppy)$_3$

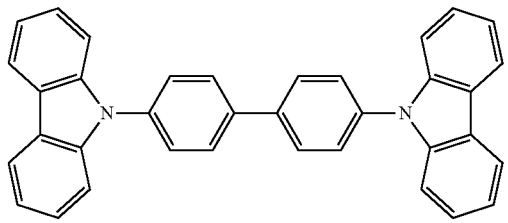

CBP

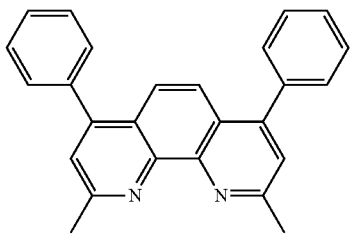

BCP

[Examples 2 to 10] Manufacture of Green Organic Electroluminescent Device

Green organic electroluminescent devices were manufactured in the same manner as in Example 1 except that compounds described in the following Table 1 were each used instead of Compound Cpd148 used in Example 1.

[Comparative Example 1] Manufacture of Green Organic Electroluminescent Device A green organic electroluminescent device was manufactured in the same manner as in Example 1 except that Compound Cpd148 used in Example 1 was not used.

Evaluation Example 1

For the green organic electroluminescent devices each manufactured in Examples 1 to 10 and Comparative Example 1, a driving voltage, current efficiency and a light emission peak at current density of 10 mA/cm$^2$ were measured, and the results are shown in the following Table 1.

TABLE 1

| Sample | Auxiliary Light Emitting Layer Material | Driving Voltage (V) | Light Emission Peak (nm) | Current Efficiency (cd/A) |
|---|---|---|---|---|
| Example 1 | Cpd148 | 6.75 | 518 | 41.8 |
| Example 2 | Cpd149 | 6.80 | 517 | 41.5 |

TABLE 1-continued

| Sample | Auxiliary Light Emitting Layer Material | Driving Voltage (V) | Light Emission Peak (nm) | Current Efficiency (cd/A) |
|---|---|---|---|---|
| Example 3 | Cpd150 | 6.77 | 518 | 42.0 |
| Example 4 | Cpd152 | 6.72 | 520 | 41.9 |
| Example 5 | Cpd154 | 6.80 | 518 | 41.5 |
| Example 6 | Cpd155 | 6.69 | 520 | 41.8 |
| Example 7 | Cpd156 | 6.82 | 517 | 41.8 |
| Example 8 | Cpd158 | 6.75 | 518 | 41.8 |
| Example 9 | Cpd179 | 6.80 | 520 | 42.0 |
| Example 10 | Cpd180 | 6.77 | 518 | 42.0 |
| Comparative Example 1 | — | 6.93 | 516 | 38.2 |

*334

As shown in Table 1, it was seen that the green organic electroluminescent devices of Examples 1 to 10 using the compound represented by Chemical Formula 1 according to the present disclosure (Compounds Cpd148 to Cpd180) as an auxiliary light emitting layer material had a slightly decreased driving voltage compared to the green organic electroluminescent device of Comparative Example 1 using only CBP as a light emitting layer material without an auxiliary light emitting layer, and had more superior current efficiency compared to the green organic electroluminescent device of Comparative Example 1.

[Example 11] Manufacture of Red Organic Electroluminescent Device

After high purity sublimation purifying Compound Cpd148 synthesized in Synthesis Example 13 using a commonly known method, a red organic electroluminescent device was manufactured as follows.

First, a glass substrate on which indium tin oxide (ITO) was coated as a thin film to a thickness of 1500 Å was distilled water ultrasonic cleaned. After the distilled water cleaning was finished, the substrate was ultrasonic cleaned with solvents such as isopropyl alcohol, acetone and methanol, dried, then transferred to a UV OZONE washer (Power sonic 405, manufactured by Hwashin Tech. Co., Ltd.), and then, after cleaning the substrate for 5 minutes using UV, the substrate was transferred to a vacuum depositor.

On the transparent ITO electrode prepared as above, m-MTDATA (60 nm)/TCTA (80 nm)/Compound cpd148 (40 nm)/CBP+10% (piq)$_2$Ir(acac) (300 nm)/BCP (10 nm)/Alq$_3$ (30 nm)/LiF (1 nm)/Al (200 nm) were laminated in this order to manufacture a red organic electroluminescent device.

Structures of the m-MTDATA, the TCTA, the CBP and the BCP used herein are the same as described in Example 1, and the (piq)$_2$Ir(acac) is as follows.

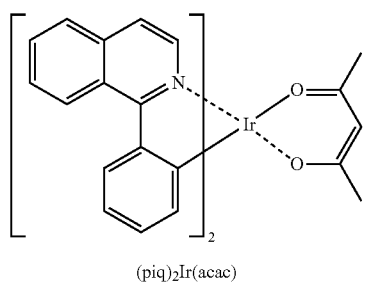

(piq)$_2$Ir(acac)

[Examples 12 to 20] Manufacture of Red Organic Electroluminescent Device

Red organic electroluminescent devices were manufactured in the same manner as in Example 11 except that compounds described in the following Table 2 were each used instead of Compound Cpd148 used in Example 11.

[Comparative Example 2] Manufacture of Red Organic Electroluminescent Device

A red organic electroluminescent device was manufactured in the same manner as in Example 11 except that Compound Cpd148 used in Example 11 was not used.

Evaluation Example 2

For each of the red organic electroluminescent devices manufactured in Examples 11 to 20 and Comparative Example 2, a driving voltage and current efficiency at current density of 10 mA/cm$^2$ were measured, and the results are shown in the following Table 2.

TABLE 2

| Sample | Auxiliary Light Emitting Layer Material | Driving Voltage (V) | Current Efficiency (cd/A) |
|---|---|---|---|
| Example 11 | Cpd148 | 5.13 | 11.1 |
| Example 12 | Cpd149 | 5.16 | 11.5 |
| Example 13 | Cpd150 | 5.17 | 11.6 |
| Example 14 | Cpd152 | 5.14 | 11.0 |
| Example 15 | Cpd154 | 5.15 | 10.8 |
| Example 16 | Cpd155 | 5.10 | 11.2 |
| Example 17 | Cpd156 | 5.15 | 11.0 |
| Example 18 | Cpd158 | 5.20 | 11.3 |
| Example 19 | Cpd179 | 5.15 | 11.0 |
| Example 20 | Cpd180 | 5.10 | 11.3 |
| Comparative Example 2 | — | 5.25 | 8.2 |

As shown in Table 2, it was seen that the red organic electroluminescent devices of Examples 11 to 20 using the compound represented by Chemical Formula 1 according to the present disclosure (Compounds Cpd148 to Cpd180) as an auxiliary light emitting layer material had a slightly decreased driving voltage, and also had more superior current efficiency compared to the red organic electroluminescent device of Comparative Example 2 using only CBP as a light emitting layer material without an auxiliary light emitting layer.

[Example 21] Manufacture of Blue Organic Electroluminescent Device

After high purity sublimation purifying Compound Cpd148 synthesized in Synthesis Example 13 using a commonly known method, a blue organic electroluminescent device was manufactured as follows.

First, a glass substrate on which indium tin oxide (ITO) was coated as a thin film to a thickness of 1500 Å was distilled water ultrasonic cleaned. After the distilled water cleaning was finished, the substrate was ultrasonic cleaned with solvents such as isopropyl alcohol, acetone and methanol, dried, then transferred to a UV OZONE washer (Power sonic 405, manufactured by Hwashin Tech. Co., Ltd.), and then, after cleaning the substrate for 5 minutes using UV, the substrate was transferred to a vacuum depositor.

On the transparent ITO electrode prepared as above, DS-205 (Doosan Corporation) (80 nm)/NPB (15 nm)/Compound Cpd148 (15 nm)/ADN+5% DS-405 (Doosan Corporation) (300 nm)/BCP (10 nm)/Alq$_3$ (30 nm)/LiF (1 nm)/Al (200 nm) were laminated in this order to manufacture a blue organic electroluminescent device.

The BCP used is the same as described in Example 1, and structures of the NPB and the AND are as follows.

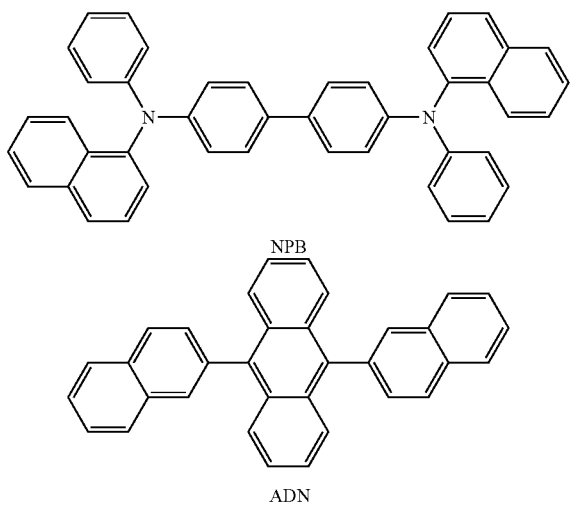

NPB

ADN

[Examples 22 to 30] Manufacture of Blue Organic Electroluminescent Device

Blue organic electroluminescent devices were manufactured in the same manner as in Example 21 except that compounds described in the following Table 3 were each used instead of Compound Cpd148 used in Example 21.

[Comparative Example 3] Manufacture of Blue Organic Electroluminescent Device

A blue organic electroluminescent device was manufactured in the same manner as in Example 21 except that Compound Cpd148 used in Example 21 was not used.

Evaluation Example 3

For each of the blue organic electroluminescent devices manufactured in Examples 21 to 30 and Comparative Example 3, a driving voltage and current efficiency at current density of 10 mA/cm$^2$ were measured, and the results are shown in the following Table 3.

TABLE 3

| Sample | Auxiliary Light Emitting Layer Material | Driving Voltage (V) | Current Efficiency (cd/A) |
| --- | --- | --- | --- |
| Example 21 | Cpd148 | 5.50 | 6.9 |
| Example 22 | Cpd149 | 5.60 | 6.6 |
| Example 23 | Cpd150 | 5.55 | 6.8 |
| Example 24 | Cpd152 | 5.60 | 6.9 |
| Example 25 | Cpd154 | 5.51 | 6.6 |
| Example 26 | Cpd155 | 5.55 | 6.8 |
| Example 27 | Cpd156 | 5.51 | 6.0 |
| Example 28 | Cpd158 | 5.55 | 6.4 |
| Example 29 | Cpd179 | 5.60 | 6.5 |
| Example 30 | Cpd180 | 5.65 | 6.8 |
| Comparative Example 3 | — | 5.60 | 4.8 |

As shown in Table 3, it was seen that the blue organic electroluminescent devices of Examples 21 to 30 using the compound represented by Chemical Formula 1 according to the present disclosure (Compounds Cpd148 to Cpd180) as an auxiliary light emitting layer had a similar driving voltage with the blue organic electroluminescent device of Comparative Example 3 using AND as a light emitting layer material without an auxiliary light emitting layer, but had more superior current efficiency compared to the organic electroluminescent device of Comparative Example 3.

[Example 31] Manufacture of Green Organic Electroluminescent Device

After high purity sublimation purifying Compound Cpd50 synthesized in Synthesis Example 1 using a commonly known method, a green organic electroluminescent device was manufactured using the following process.

First, a glass substrate on which indium tin oxide (ITO) was coated as a thin film to a thickness of 1500 Å was distilled water ultrasonic cleaned. After the distilled water cleaning was finished, the substrate was ultrasonic cleaned with solvents such as isopropyl alcohol, acetone and methanol, dried, then transferred to a UV OZONE washer (Power sonic 405, manufactured by Hwashin Tech. Co., Ltd.), and then, after cleaning the substrate for 5 minutes using UV, the substrate was transferred to a vacuum depositor.

On the transparent ITO electrode prepared as above, m-MTDATA (60 nm)/TCTA (80 nm)/Compound Cpd50+ 10% Ir(ppy)$_3$ (300 nm)/BCP (10 nm)/Alq$_3$ (30 nm)/LiF (1 nm)/Al (200 nm) were laminated in this order to manufacture an organic electroluminescent device.

[Examples 32 to 42] Manufacture of Green Organic Electroluminescent Device

Green organic electroluminescent devices were manufactured in the same manner as in Example 31 except that compounds described in the following Table 4 were each used instead of Compound Cpd50 used in Example 31.

[Comparative Example 4] Manufacture of Green Organic Electroluminescent Device

A green organic electroluminescent device was manufactured in the same manner as in Example 31 except that CBP was used instead of Compound Cpd50 used as a light emitting host material when forming the light emitting layer in Example 31.

Evaluation Example 4

For each of the green organic electroluminescent devices manufactured in Examples 31 to 42 and Comparative Example 4, a driving voltage, current efficiency and a light emission peak at current density of 10 mA/cm$^2$ were measured, and the results are shown in the following Table 4.

TABLE 4

| Sample | Host | Driving Voltage (V) | Light Emission Peak (nm) | Current Efficiency (cd/A) |
|---|---|---|---|---|
| Example 31 | Cpd50 | 6.79 | 517 | 40.8 |
| Example 32 | Cpd51 | 6.81 | 518 | 41.1 |
| Example 33 | Cpd52 | 6.79 | 517 | 40.8 |
| Example 34 | Cpd53 | 6.78 | 515 | 42.4 |
| Example 35 | Cpd54 | 6.81 | 518 | 41.1 |
| Example 36 | Cpd77 | 6.79 | 517 | 40.8 |
| Example 37 | Cpd83 | 6.81 | 518 | 41.1 |
| Example 38 | Cpd92 | 6.79 | 517 | 40.8 |
| Example 39 | Cpd95 | 6.79 | 517 | 40.8 |
| Example 40 | Cpd96 | 6.81 | 518 | 41.1 |
| Example 41 | Cpd97 | 6.79 | 517 | 40.8 |
| Example 42 | Cpd98 | 6.79 | 517 | 40.8 |
| Comparative Example 4 | CBP | 6.93 | 516 | 38.2 |

*390

As shown in Table 4, it was seen that the green organic electroluminescent devices of Examples 31 to 42 each using the synthesized compound (Compounds Cpd50 to Cpd98) as a light emitting layer material exhibited more superior performance in terms of current efficiency and driving voltage compared to the green organic electroluminescent device of Comparative Example 4 using existing CBP.

[Example 43] Manufacture of Blue Organic Electroluminescent Device

After high purity sublimation purifying Compound Cpd50 synthesized in Synthesis Example 1 using a commonly known method, a blue organic electroluminescent device was manufactured using the following process.

First, a glass substrate on which indium tin oxide (ITO) was coated as a thin film to a thickness of 1500 Å was distilled water ultrasonic cleaned. After the distilled water cleaning was finished, the substrate was ultrasonic cleaned with solvents such as isopropyl alcohol, acetone and methanol, dried, then transferred to a UV OZONE washer (Power sonic 405, manufactured by Hwashin Tech. Co., Ltd.), and then, after cleaning the substrate for 5 minutes using UV, the substrate was transferred to a vacuum depositor.

On the transparent ITO electrode prepared as above, CuPc (10 nm)/TPAC (30 nm)/Compound Cpd50+7% Flrpic (30 nm)/Alq$_3$ (30 nm)/LiF (0.2 nm)/Al (150 nm) were laminated in this order to manufacture an organic electroluminescent device.

Structures of the CuPc, the TPAC and the Flrpic used herein are each as follows.

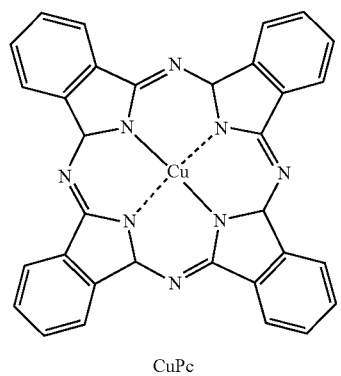

CuPc

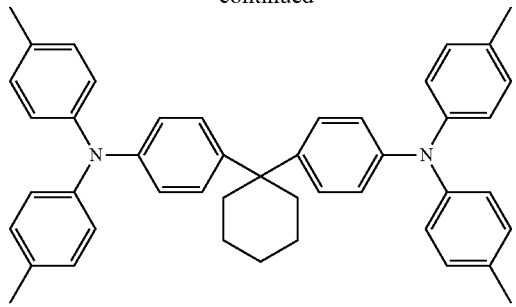

TPAC

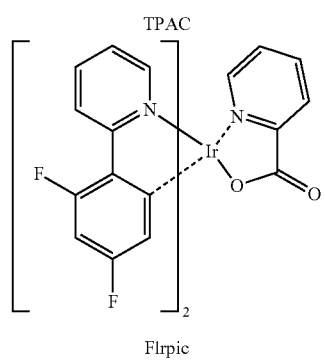

Flrpic

[Examples 44 to 47] Manufacture of Blue Organic Electroluminescent Device

Blue organic electroluminescent devices were manufactured in the same manner as in Example 43 except that compounds described in the following Table 5 were each used instead of Compound Cpd50 used in Example 43.
*402

[Comparative Example 5] Manufacture of Blue Organic Electroluminescent Device

A blue organic electroluminescent device was manufactured in the same manner as in Example 43 except that CBP was used instead of Compound Cpd50 used as a light emitting host material when forming the light emitting layer in Example 43.

Evaluation Example 5

For each of the blue organic electroluminescent devices manufactured in Examples 43 to 47 and Comparative Example 5, a driving voltage, current efficiency and a light emission peak at current density of 10 mA/cm$^2$ were measured, and the results are shown in the following Table 5.

TABLE 5

| Sample | Host | Driving Voltage (V) | Light Emission Peak (nm) | Current Efficiency (cd/A) |
|---|---|---|---|---|
| Example 43 | Cpd50 | 7.29 | 473 | 6.90 |
| Example 44 | Cpd51 | 7.30 | 474 | 6.34 |
| Example 45 | Cpd52 | 7.24 | 475 | 6.55 |
| Example 46 | Cpd53 | 7.15 | 471 | 6.94 |
| Example 47 | Cpd54 | 7.23 | 472 | 6.25 |
| Comparative Example 5 | CBP | 7.80 | 474 | 5.80 |

As shown in Table 5, it was seen that the blue organic electroluminescent devices of Examples 43 to 47 using the compound according to the present disclosure (Compounds Cpd50 to Cpd54) as a light emitting layer material exhibited more superior performance in terms of current efficiency and driving voltage compared to the blue organic electroluminescent device of Comparative Example 5 using existing CBP.

Hereinbefore, preferred embodiments of the present disclosure have been described, however, the present disclosure is not limited thereto, and various modifications may be made within the scope of the claims and the detailed descriptions of the disclosure, and these modifications also belong to the category of the disclosure.

INDUSTRIAL APPLICABILITY

The present disclosure relates to a novel organic compound capable of being used as a material for an organic electroluminescent device, and an organic electroluminescent device including the same.

The invention claimed is:
1. A compound of the following Chemical Formula 3, 4, or 5:

[Chemical Formula 3]

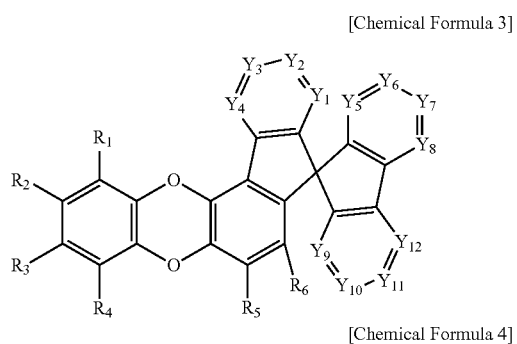

[Chemical Formula 4]

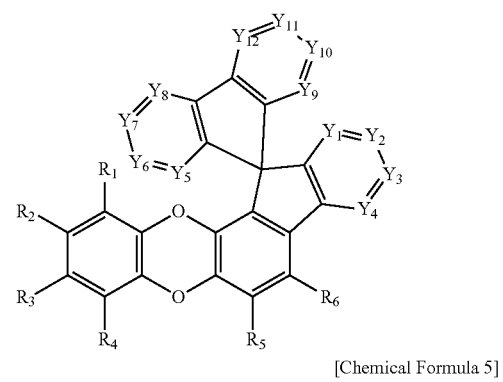

[Chemical Formula 5]

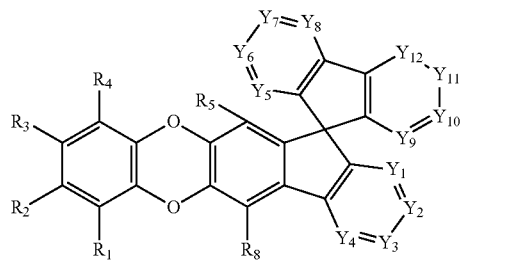

wherein, in Formulae 3 to 5,
$R_1$ to $R_6$ and $R_8$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylamine group, or bond to adjacent groups to form a fused ring;

the $R_1$ to $R_6$ and $R_8$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, and when substituted with a plurality of substituents, these are the same as or different from each other;

$Y_1$ to $Y_{12}$ are each independently C(H) or C($R_9$), and at least one of them is C($R_9$);

$R_9$ is a substituent of the following Chemical Formula 6:

[Chemical Formula 6]

$$*-L_1-L_2-R_{10}$$

in Chemical Formula 6,
* means a part where a bond is formed;
$L_1$ and $L_2$ are each independently selected from the group consisting of a direct bond, a $C_6$~$C_{18}$ arylene group and a heteroarylene group having 5 to 18 nuclear atoms;
$R_{10}$ is selected from the group consisting of halogen, a cyano group, a nitro group, a $C_6$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylamine group, or bonds to adjacent groups to form a fused ring; and the $L_1$ and $L_2$ arylene group and heteroarylene group, and the $R_{10}$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, and when substituted with a plurality of substituents, these are the same as or different from each other.

2. The compound of claim 1, wherein $L_1$ and $L_2$ are each independently represented by any one of the following Chemical Formulae 7 to 11:

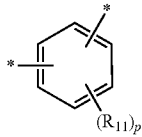

[Chemical Formula 7]

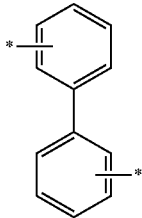

[Chemical Formula 8]

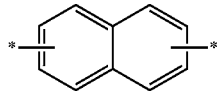

[Chemical Formula 9]

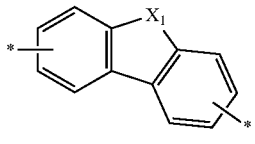

[Chemical Formula 10]

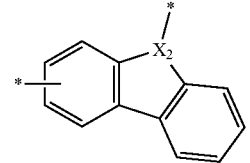

[Chemical Formula 11]

in Chemical Formulae 7 to 11,
* means a part where a bond is formed;
$X_1$ is O, S, $N(R_{12})$ or $C(R_{13})(R_{14})$;
$X_2$ is N or $C(R_{15})$;
p is an integer of 0 to 4;
$R_{11}$ is selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylamine group, or bonds to adjacent groups to form a fused ring, and when $R_{11}$ is present in plural numbers, these are the same as or different from each other;

$R_{12}$ to $R_{15}$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_3$~$C_{40}$ cycloalkyl group, a heterocycloalkyl group having 3 to 40 nuclear atoms, a $C_6$~$C_{60}$ arylamine group, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, or bond to adjacent groups to form a fused ring; and the $R_{11}$ to $R_{15}$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, and when substituted with a plurality of substituents, these are the same as or different from each other.

3. The compound of claim 1, wherein $R_{10}$ is selected from the group consisting of a $C_6$~$C_{60}$ aryl group, a heteroaryl group having 5 to 60 nuclear atoms and a $C_6$~$C_{60}$ arylamine group.

4. The compound of claim 1, wherein $R_{10}$ is a substituent represented by any one of the following Chemical Formulae 12 to 14:

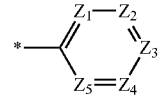

[Chemical Formula 12]

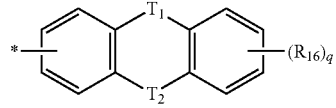

[Chemical Formula 13]

-continued

[Chemical Formula 14]

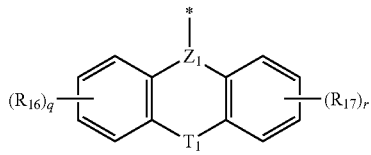

in Chemical Formulae 12 to 14,
* means a part where a bond is formed;
$Z_1$ to $Z_5$ are each independently N or $C(R_{18})$;
$T_1$ and $T_2$ are each independently selected from the group consisting of a direct bond, a $C(R_{19})(R_{20})$, $N(R_{21})$, O and S, however, $T_1$ and $T_2$ are not both a direct bond;
q and r are each independently an integer of 0 to 4;
$R_{16}$ and $R_{17}$ are each independently selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_3$~$C_{40}$ cycloalkyl group, a heterocycloalkyl group having 3 to 40 nuclear atoms, a $C_6$~$C_{60}$ arylamine group, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, or bond to adjacent groups to form a fused ring, and when each of $R_{16}$ and $R_{17}$ is present in plural numbers, these are the same as or different from each other;
$R_{18}$ to $R_{21}$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_3$~$C_{40}$ cycloalkyl group, a heterocycloalkyl group having 3 to 40 nuclear atoms, a $C_6$~$C_{60}$ arylamine group, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, or bond to adjacent groups to form a fused ring, and when each of $R_{18}$ to $R_{21}$ is present in plural numbers, these are the same as or different from each other; and
the $R_{16}$ to $R_{21}$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, and when substituted with a plurality of substituents, these are the same as or different from each other.

5. The compound of claim 1, wherein $R_{10}$ is a substituent represented by any one of the following Chemical Formulae A-1 to A-24:

A-1
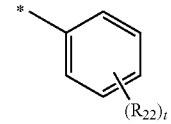

A-2
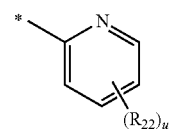

A-3
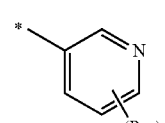

A-4
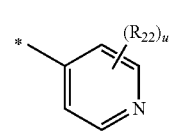

A-5
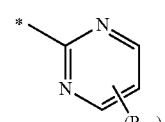

A-6
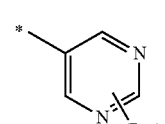

A-7
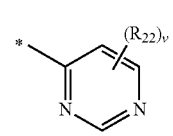

A-8
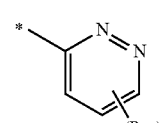

A-9
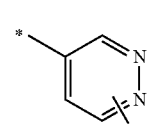

A-10
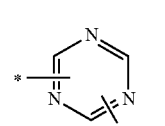

-continued

A-11
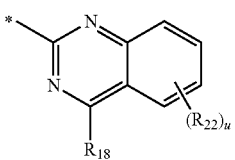

A-12
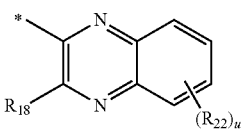

A-13
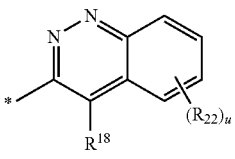

A-14
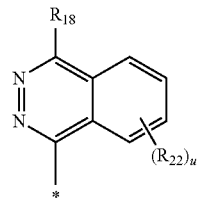

A-15
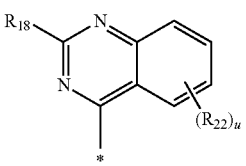

A-16
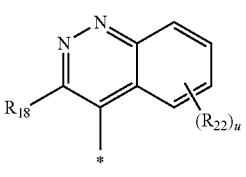

A-17
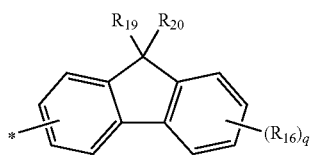

A-18
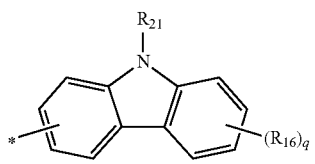

A-19
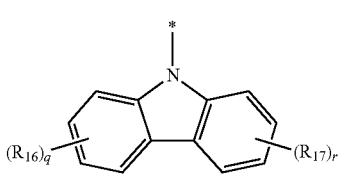

-continued

A-20
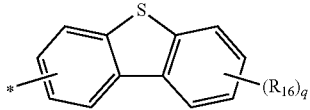

A-21
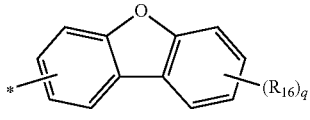

A-22
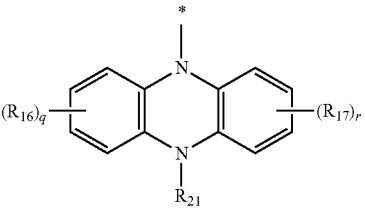

A-23
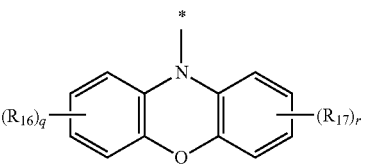

A-24
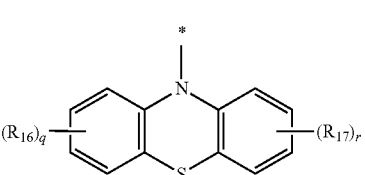

in Chemical Formulae A-1 to A-24,

* means a part where a bond is formed;

t is an integer of 0 to 5, u is an integer of 0 to 4;

v is an integer of 0 to 3;

w is an integer of 0 to 2;

q and r are each independently an integer of 0 to 4;

$R_{16}$, $R_{17}$ and $R_{22}$ are each independently selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_3$~$C_{40}$ cycloalkyl group, a heterocycloalkyl group having 3 to 40 nuclear atoms, a $C_6$~$C_{60}$ arylamine group, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphynyl group and a $C_6$~$C_{60}$ arylsilyl group, or bond to adjacent groups to form a fused ring, and when each of $R_{16}$, $R_{17}$ and $R_{22}$ is present in plural numbers, these are the same as or different from each other;

$R_{18}$ to $R_{21}$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_3$~$C_{40}$ cycloalkyl group, a heterocycloalkyl group having 3 to 40 nuclear atoms, a $C_6$~$C_{60}$ arylamine group, a $C_1$~$C_{40}$ alkylsilyl group, a $C_1$~$C_{40}$ alkylboron group, a $C_6\sim C_{60}$ arylboron group, a $C_6\sim C_{60}$ arylphosphanyl group, a $C_6\sim C_{60}$ mono or diarylphosphynyl group and a $C_6\sim C_{60}$ arylsilyl group, or bond to adjacent groups to form a fused ring; and the $R_{16}$ to $R_{22}$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1\sim C_{40}$ alkyl group, a $C_2\sim C_{40}$ alkenyl group, a $C_2\sim C_{40}$ alkynyl group, a $C_6\sim C_{60}$ aryl group, a heteroaryl group having 5 to 60 nuclear atoms, a $C_6\sim C_{60}$ aryloxy group, a $C_1\sim C_{40}$ alkyloxy group, a $C_6\sim C_{60}$ arylamine group, a $C_3\sim C_{40}$ cycloalkyl group, a heterocycloalkyl group having 3 to 40 nuclear atoms, a $C_1\sim C_{40}$ alkylsilyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphynyl group and a $C_6\sim C_{60}$ arylsilyl group, and when substituted with a plurality of substituents, these are the same as or different from each other.

6. The compound of claim 1, wherein $R_{10}$ is a substituent represented by the following Chemical Formula 15:

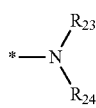

[Chemical Formula 15]

in Chemical Formula 15,

* means a part where a bond is formed;

$R_{23}$ and $R_{24}$ are each independently selected from the group consisting of hydrogen, deuterium, halogen, a cyano group, a nitro group, a $C_1\sim C_{40}$ alkyl group, a $C_2\sim C_{40}$ alkenyl group, a $C_2\sim C_{40}$ alkynyl group, a $C_6\sim C_{60}$ aryl group, a heteroaryl group having 5 to 60 nuclear atoms, a $C_6\sim C_{60}$ aryloxy group, a $C_1\sim C_{40}$ alkyloxy group, a $C_3\sim C_{40}$ cycloalkyl group, a heterocycloalkyl group having 3 to 40 nuclear atoms, a $C_6\sim C_{60}$ arylamine group, a $C_1\sim C_{40}$ alkylsilyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphynyl group and a $C_6\sim C_{60}$ arylsilyl group, or bond to adjacent groups to form a fused ring; and the $R_{23}$ and $R_{24}$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1\sim C_{40}$ alkyl group, a $C_2\sim C_{40}$ alkenyl group, a $C_2\sim C_{40}$ alkynyl group, a $C_6\sim C_{60}$ aryl group, a heteroaryl group having 5 to 60 nuclear atoms, a $C_6\sim C_{60}$ aryloxy group, a $C_1\sim C_{40}$ alkyloxy group, a $C_6\sim C_{60}$ arylamine group, a $C_3\sim C_{40}$ cycloalkyl group, a heterocycloalkyl group having 3 to 40 nuclear atoms, a $C_1\sim C_{40}$ alkylsilyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphynyl group and a $C_6\sim C_{60}$ arylsilyl group, and when substituted with a plurality of substituents, these are the same as or different from each other.

7. The compound of claim 6, wherein $R_{23}$ and $R_{24}$ are each independently selected from the group consisting of hydrogen, a $C_1\sim C_{40}$ alkyl group, a $C_6\sim C_{60}$ aryl group, a heteroaryl group having 5 to 60 nuclear atoms and a $C_6\sim C_{60}$ arylamine group.

8. The compound of claim 6, wherein $R_{23}$ and $R_{24}$ are each independently selected from the group consisting of hydrogen, a phenyl group, a biphenyl group, a terphenyl group, a naphthylenyl group, a fluorenyl group, and a substituent of the following Chemical Formula 16:

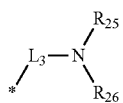

[Chemical Formula 16]

in Chemical Formula 16,

* means a part where a bond is formed;

$L_3$ is each independently selected from the group consisting of a direct bond, a $C_6\sim C_{18}$ arylene group and a heteroarylene group having 5 to 18 nuclear atoms;

$R_{25}$ and $R_{26}$ are each independently selected from the group consisting of hydrogen, deuterium, halogen, a cyano group, a nitro group, a $C_1\sim C_{40}$ alkyl group, a $C_2\sim C_{40}$ alkenyl group, a $C_2\sim C_{40}$ alkynyl group, a $C_3\sim C_{40}$ cycloalkyl group, a heterocycloalkyl group having 3 to 40 nuclear atoms, a $C_6\sim C_{60}$ aryl group, a heteroaryl group having 5 to 60 nuclear atoms, a $C_1\sim C_{40}$ alkyloxy group, a $C_6\sim C_{60}$ aryloxy group, a $C_3\sim C_{40}$ alkylsilyl group, a $C_6\sim C_{60}$ arylsilyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphynyl group and a $C_6\sim C_{60}$ arylamine group, or bond to adjacent groups to form a fused ring; and the $L_3$ arylene group and heteroarylene group, and the $R_{25}$ and $R_{26}$ alkyl group, alkenyl group, alkynyl group, aryl group, heteroaryl group, aryloxy group, alkyloxy group, cycloalkyl group, heterocycloalkyl group, arylamine group, alkylsilyl group, alkylboron group, arylboron group, arylphosphanyl group, mono or diarylphosphynyl group and arylsilyl group are each independently unsubstituted or substituted with one or more types of substituents selected from the group consisting of deuterium, halogen, a cyano group, a nitro group, a $C_1\sim C_{40}$ alkyl group, a $C_2\sim C_{40}$ alkenyl group, a $C_2\sim C_{40}$ alkynyl group, a $C_6\sim C_{60}$ aryl group, a heteroaryl group having 5 to 60 nuclear atoms, a $C_6\sim C_{60}$ aryloxy group, a $C_1\sim C_{40}$ alkyloxy group, a $C_6\sim C_{60}$ arylamine group, a $C_3\sim C_{40}$ cycloalkyl group, a heterocycloalkyl group having 3 to 40 nuclear atoms, a $C_1\sim C_{40}$ alkylsilyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphynyl group and a $C_6\sim C_{60}$ arylsilyl group, and when substituted with a plurality of substituents, these are the same as or different from each other.

9. An organic electroluminescent device comprising:
(i) an anode;
(ii) a cathode, and
(iii) one or more organic material layers provided between the anode and the cathode, wherein at least one of the one or more organic material layers includes the compound of Chemical Formula 3, 4 or 5 of claim 1.

10. The organic electroluminescent device of claim 9, wherein the organic material layer including the compound is selected from the group consisting of a hole injection layer, a hole transport layer, an electron transport layer, an auxiliary electron transport layer, an electron injection layer, a lifetime improving layer, a light emitting layer and an auxiliary light emitting layer.

11. A compound is selected from the group consisting of the following compounds:

Cpd 1
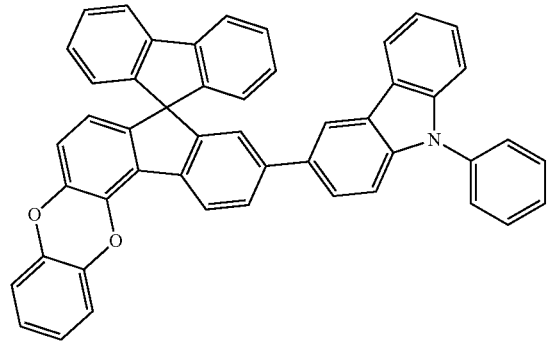

Cpd 2
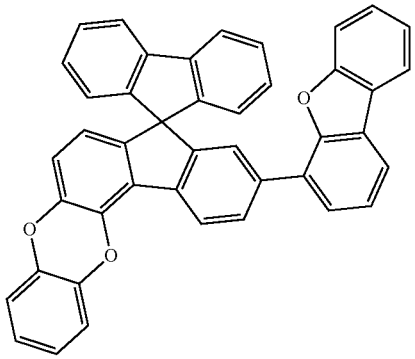

Cpd 3
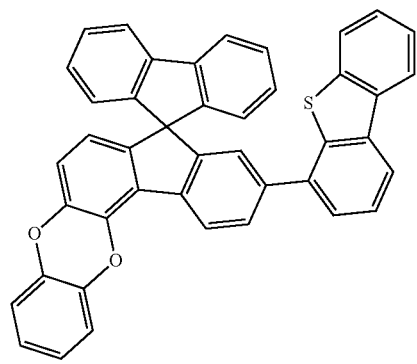

Cpd 4
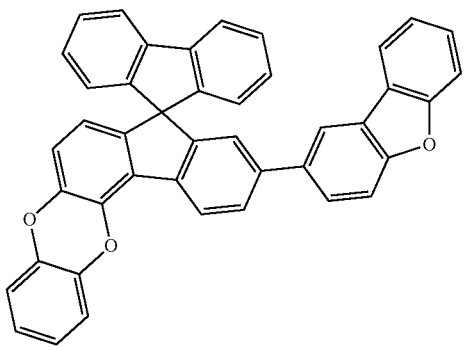

Cpd 5
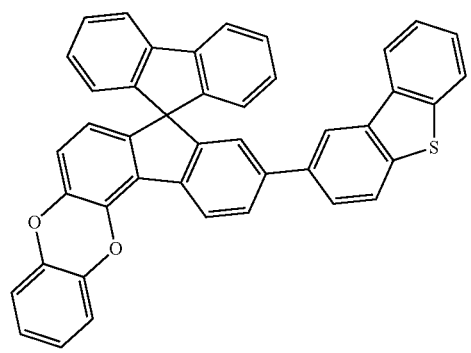

Cpd 6
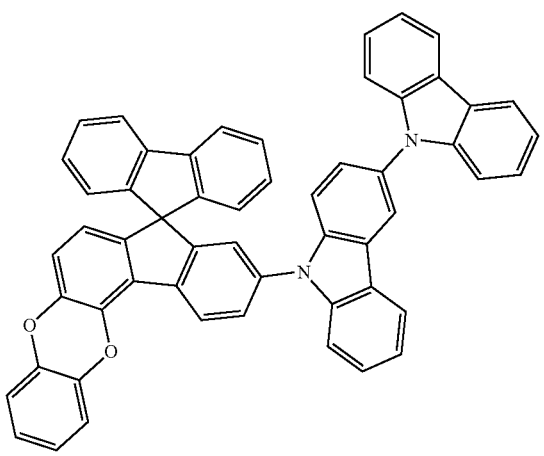

-continued
Cpd 7
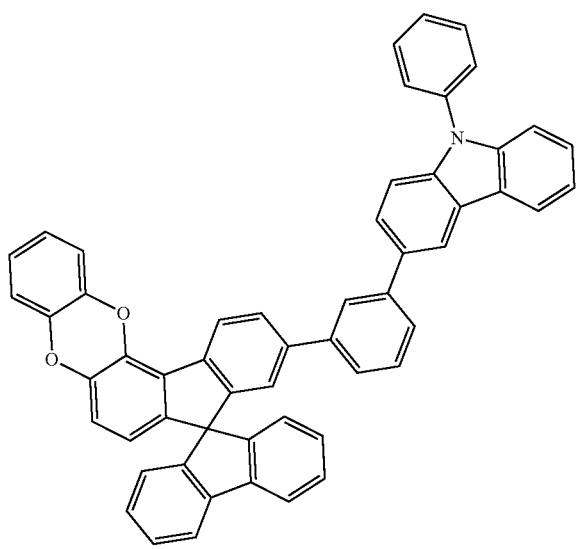
Cpd 8
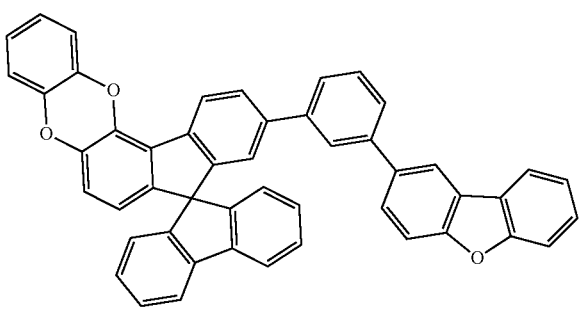
Cpd 9
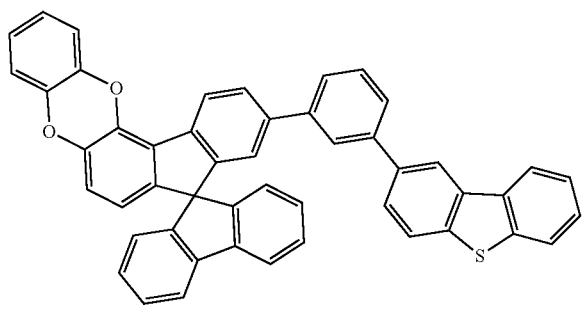
Cpd 10
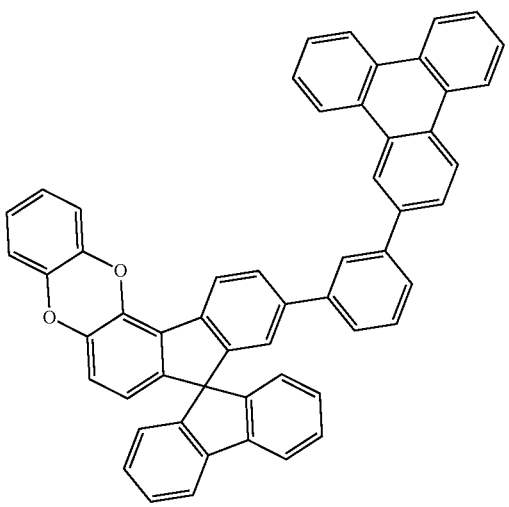
Cpd 11
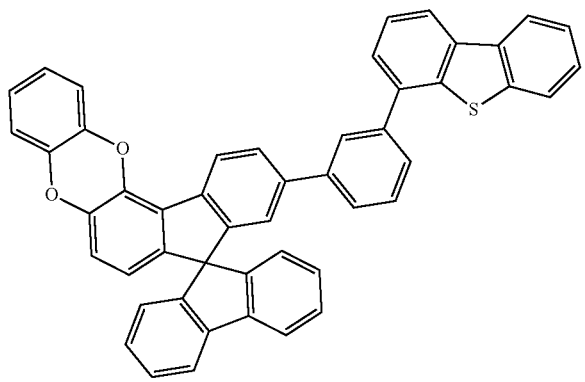
Cpd 12
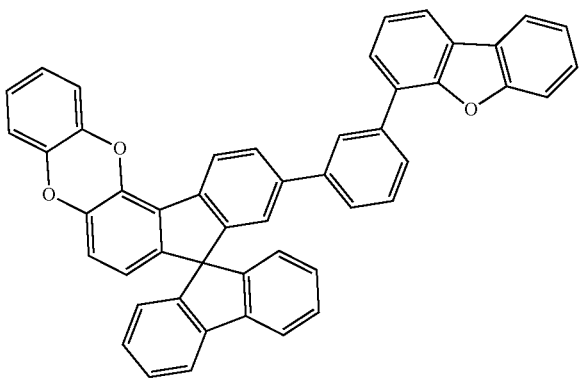

-continued
Cpd 13
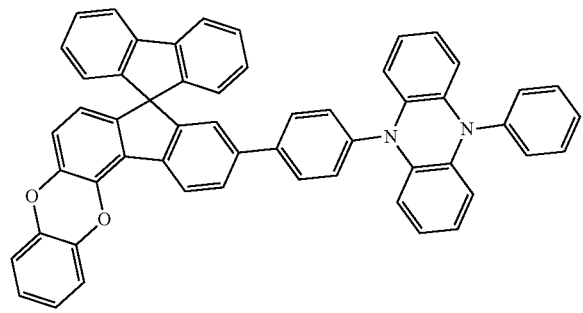
Cpd 14
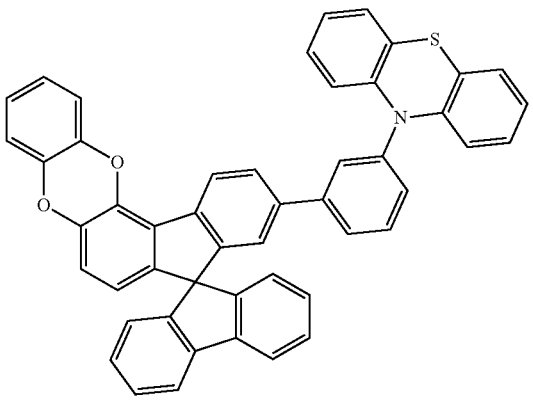
Cpd 15
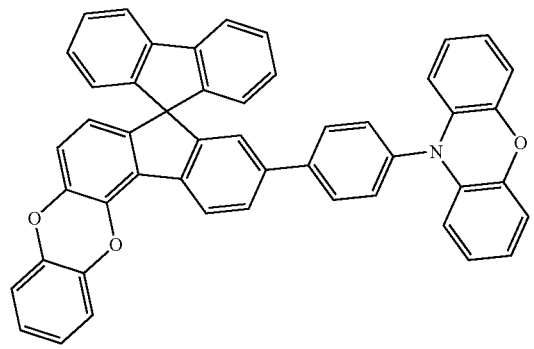
Cpd 16
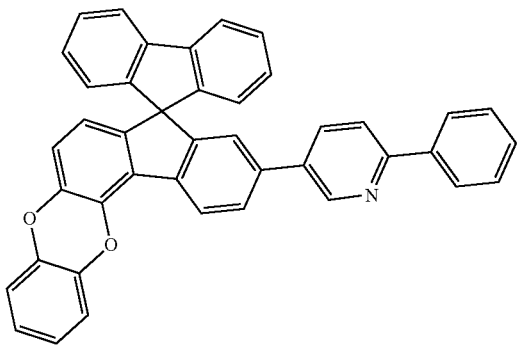
Cpd 17
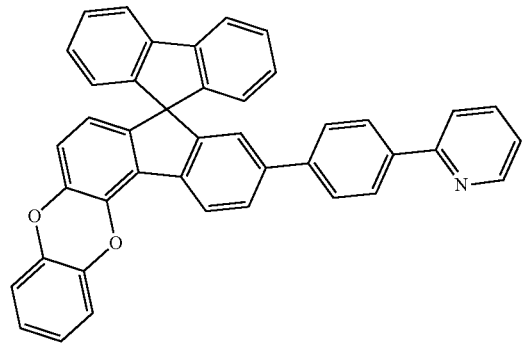
Cpd 18
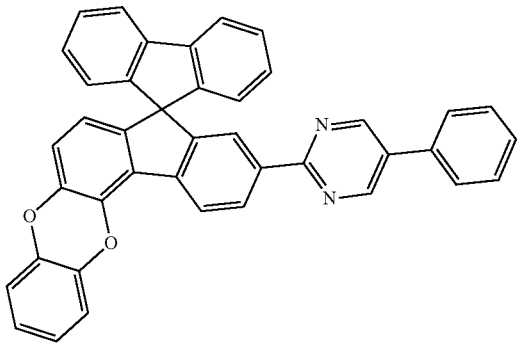
Cpd 19
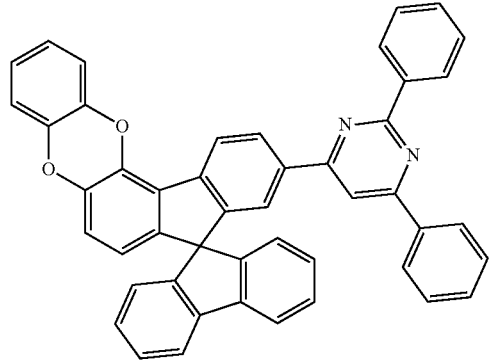
Cpd 20
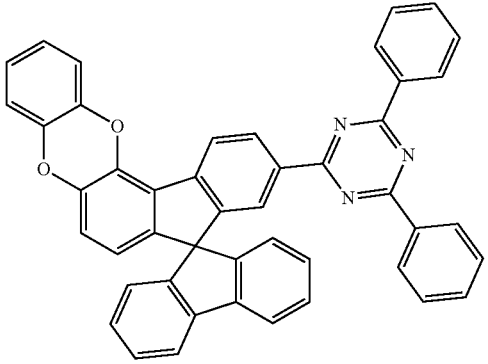

-continued
Cpd 21
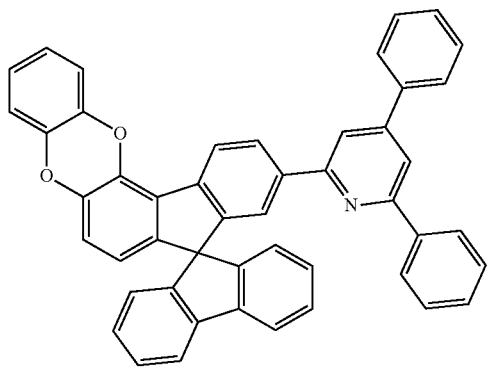
Cpd 22
Cpd 23
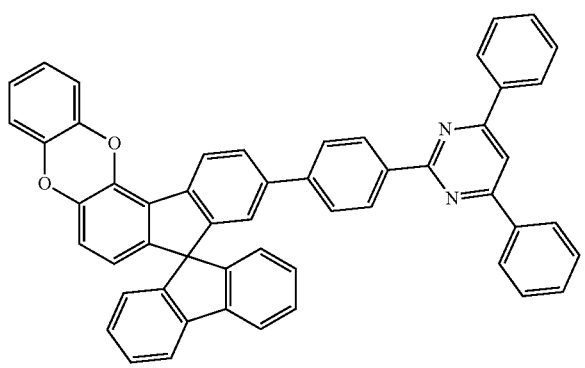
Cpd 24
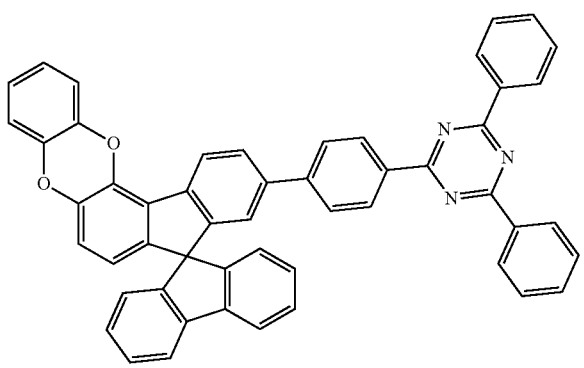
Cpd 25
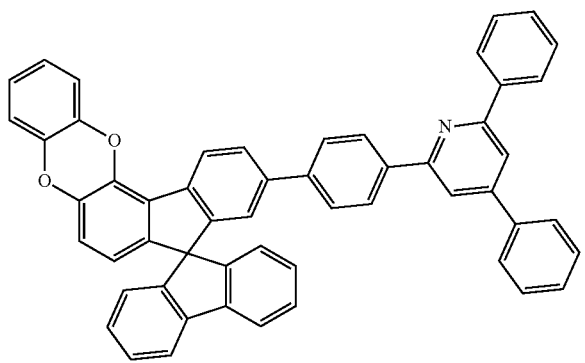
Cpd 26
Cpd 27
Cpd 28
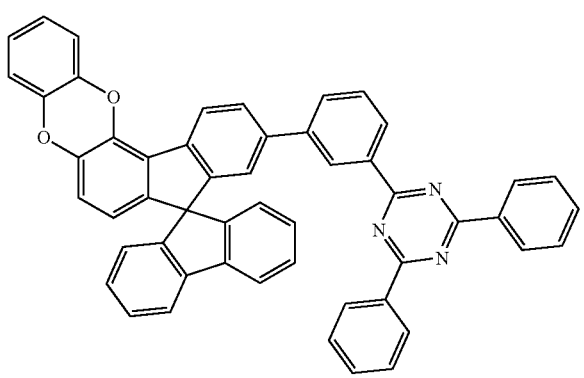

-continued
Cpd 29
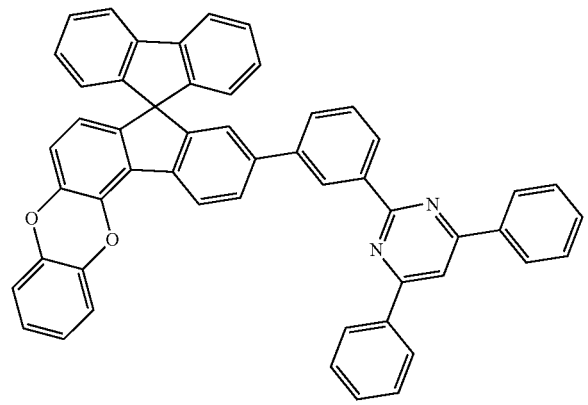
Cpd 30
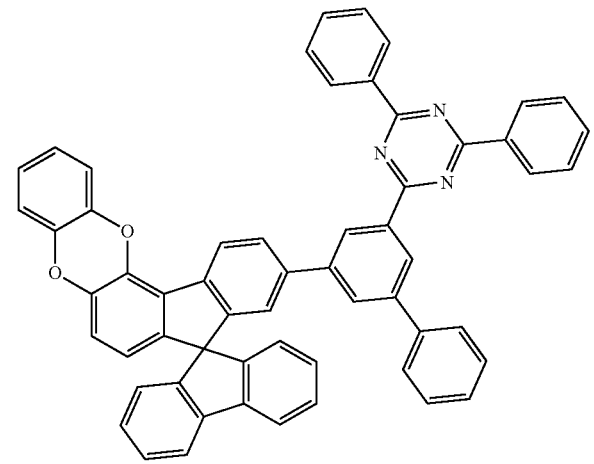
Cpd 31
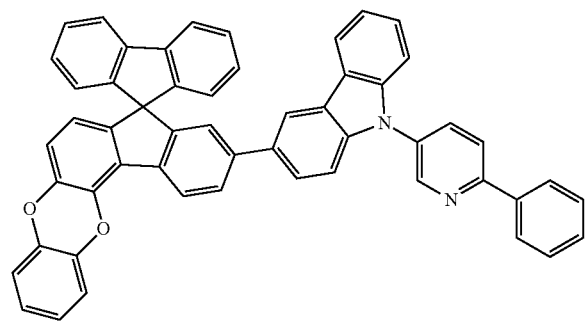
Cpd 32
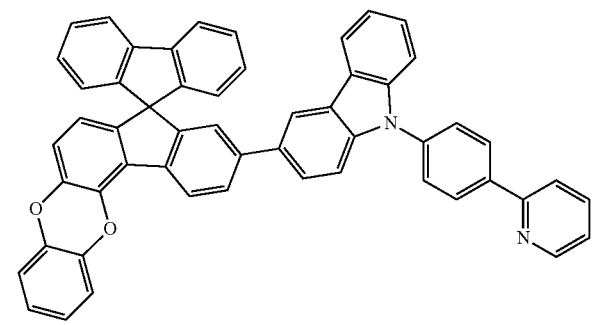
Cpd 33
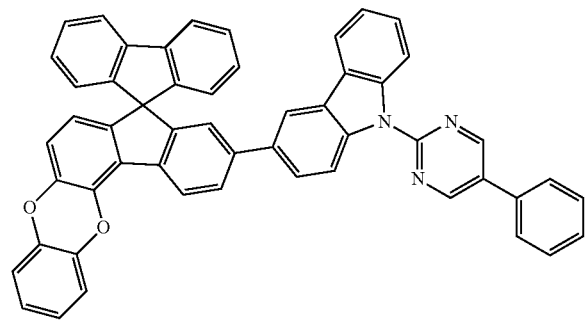
Cpd 34
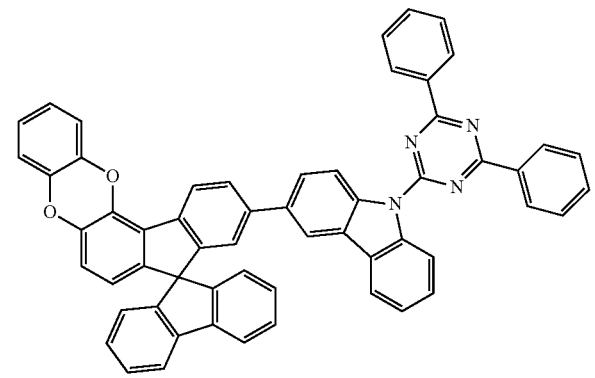
Cpd 35
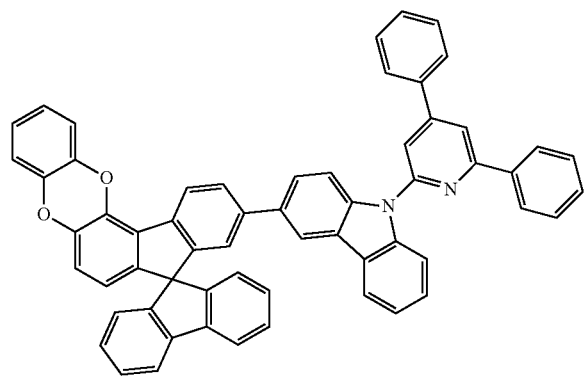
Cpd 36
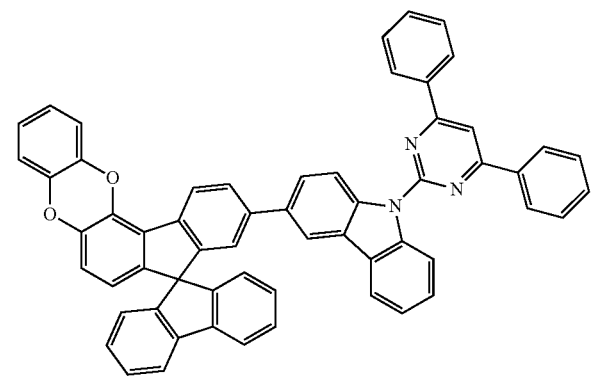

-continued
Cpd 37
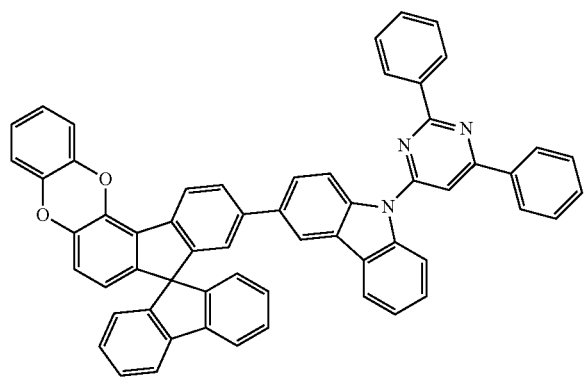
Cpd 38
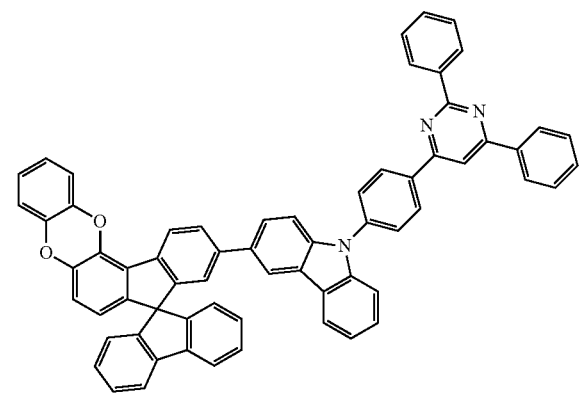
Cpd 39
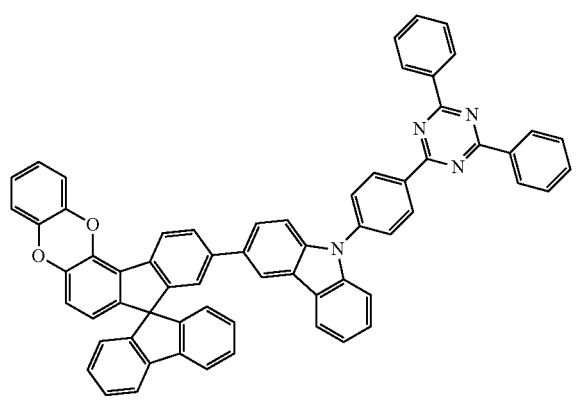
Cpd 40
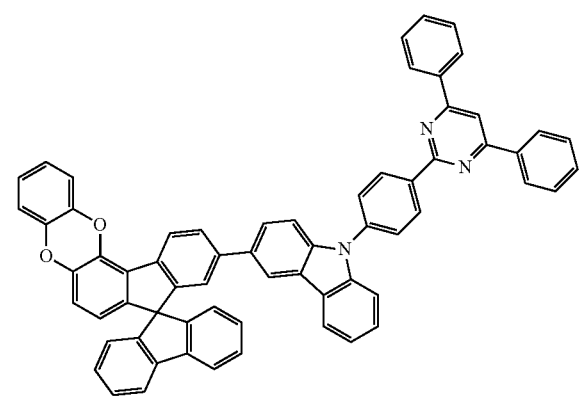
Cpd 41
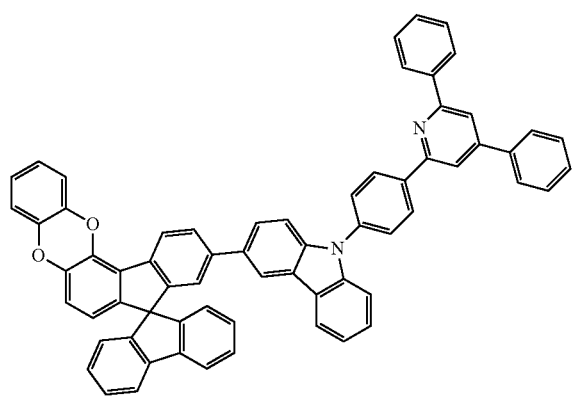
Cpd 42
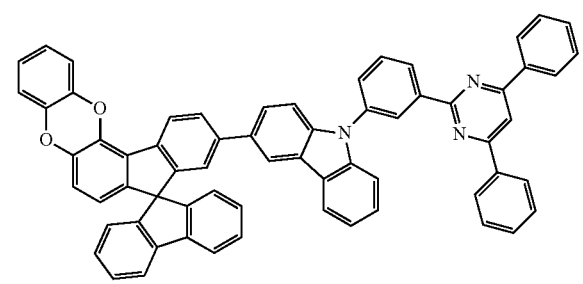
Cpd 43
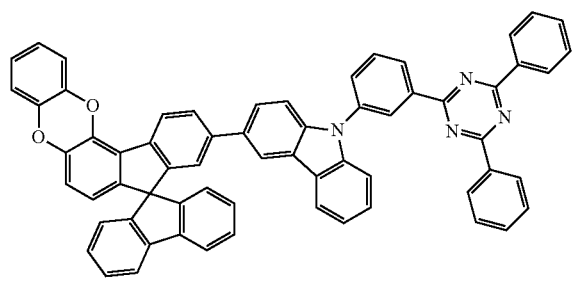
Cpd 44
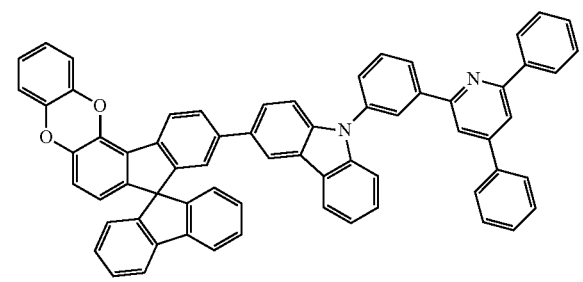

-continued
Cpd 45
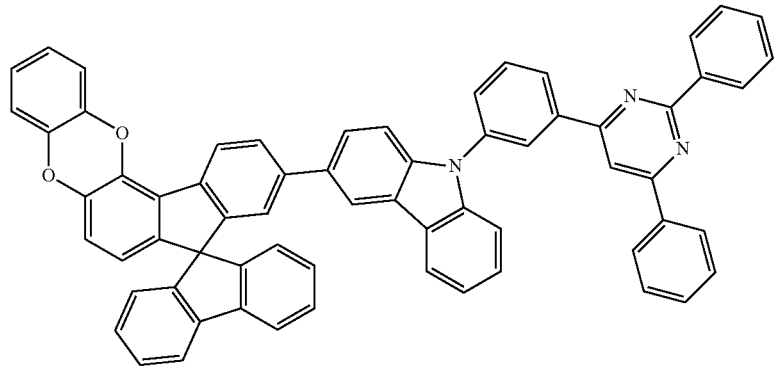
Cpd 46
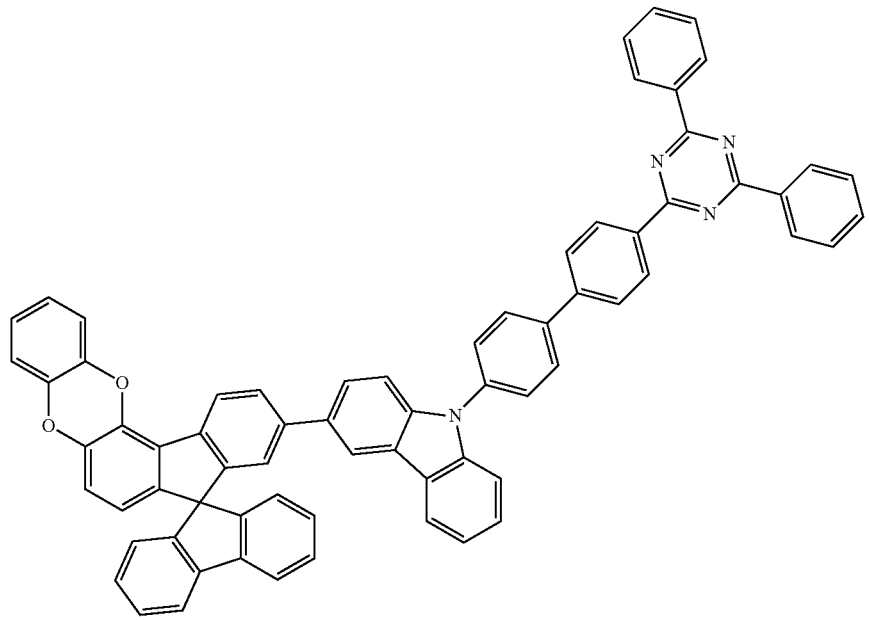
Cpd 47
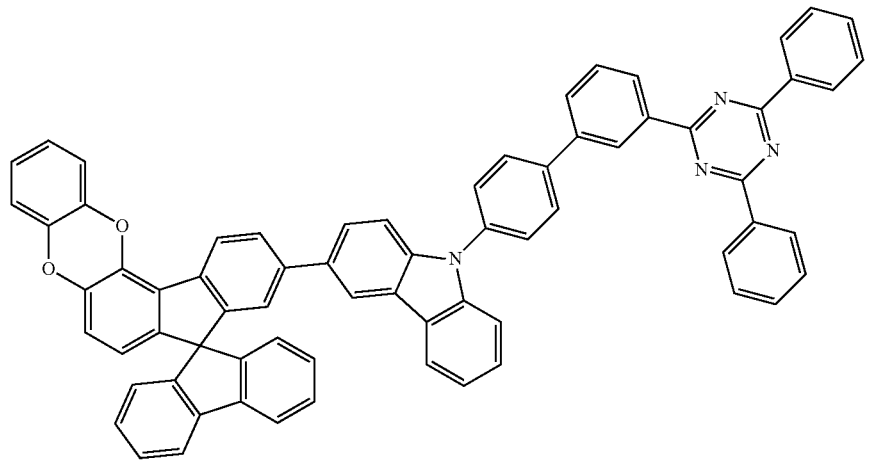

-continued
Cpd 48
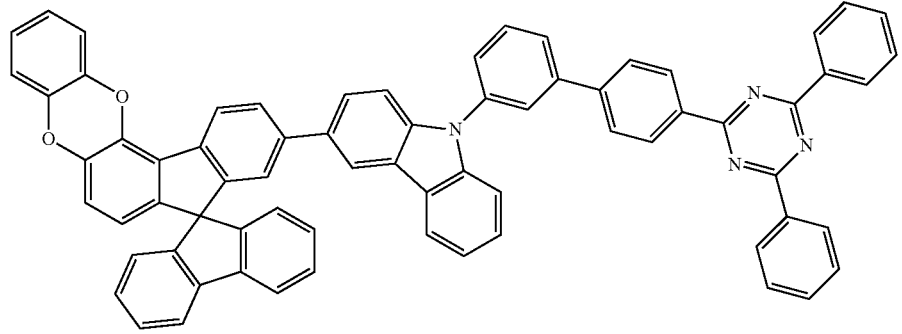
Cpd 49
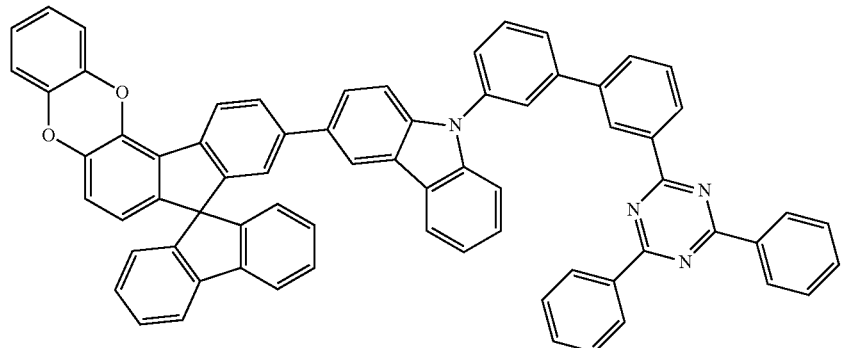
Cpd 50
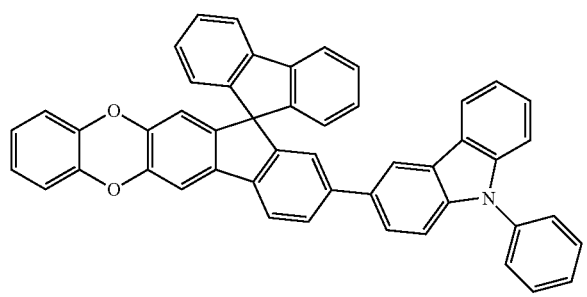
Cpd 51
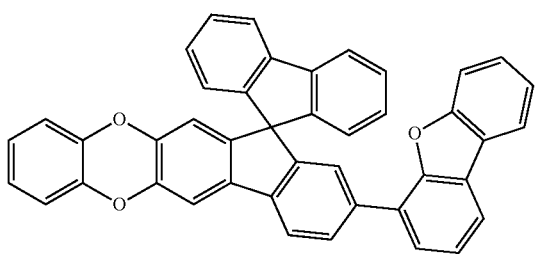
Cpd 52
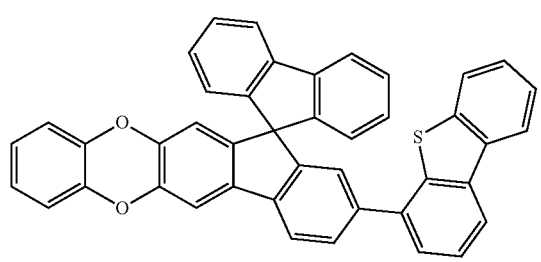
Cpd 53
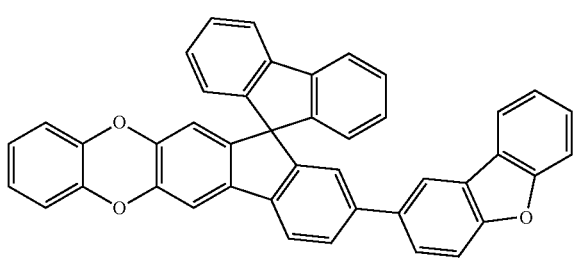
Cpd 54
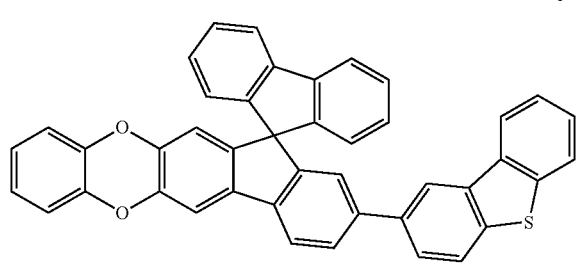
Cpd 55
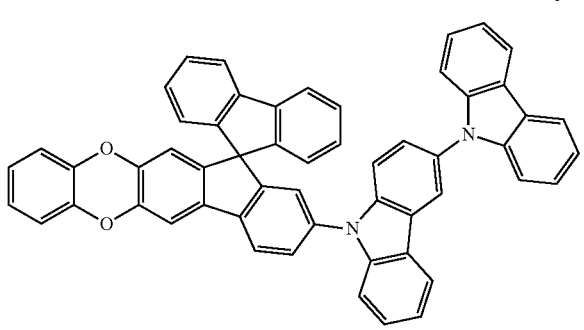

-continued
Cpd 56
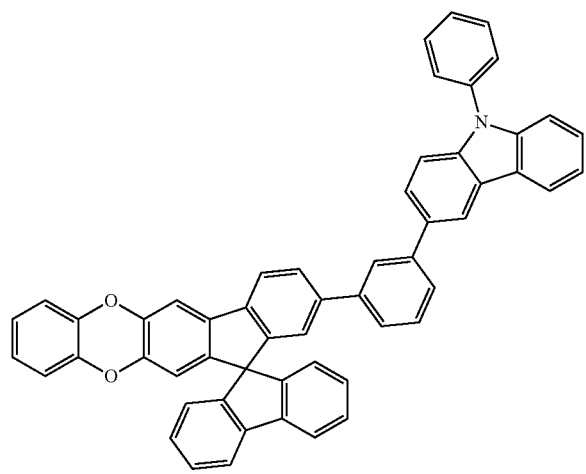
Cpd 57
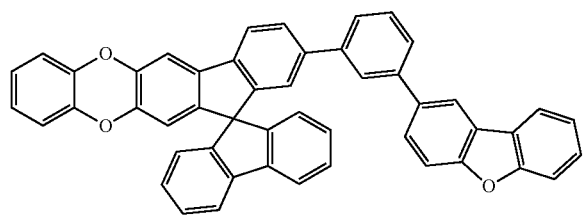
Cpd 58
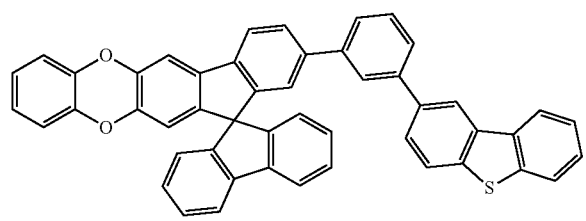
Cpd 59
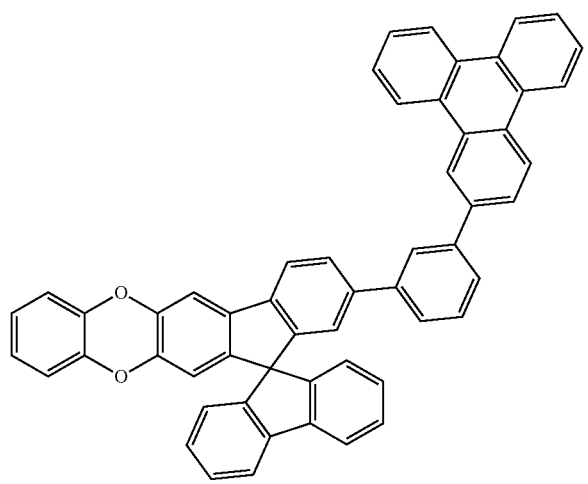
Cpd 60
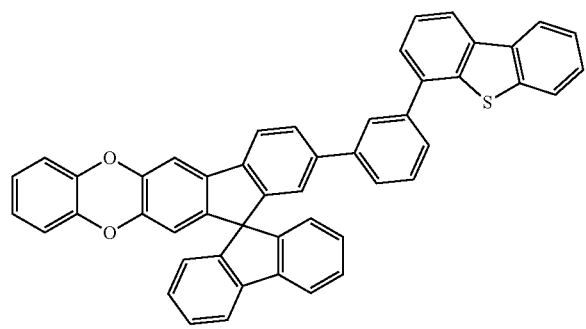
Cpd 61
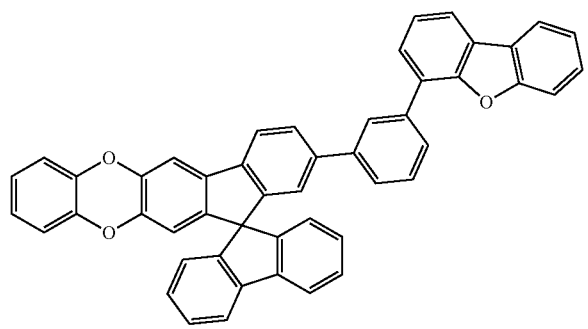

-continued
Cpd 62
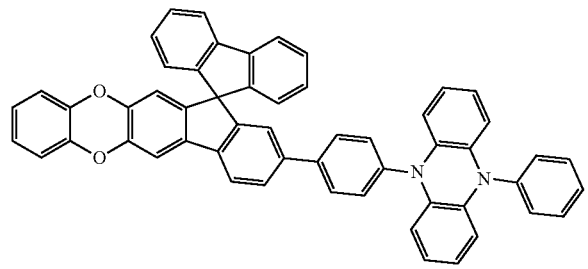
Cpd 63
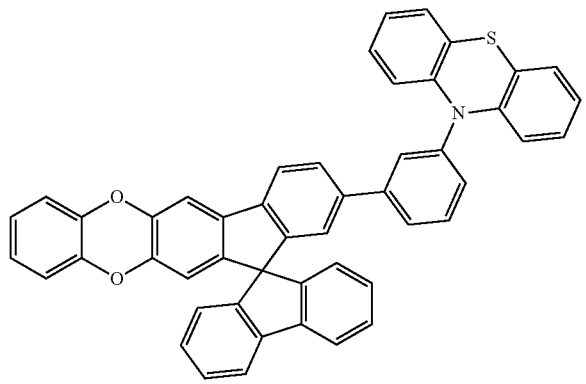
Cpd 64
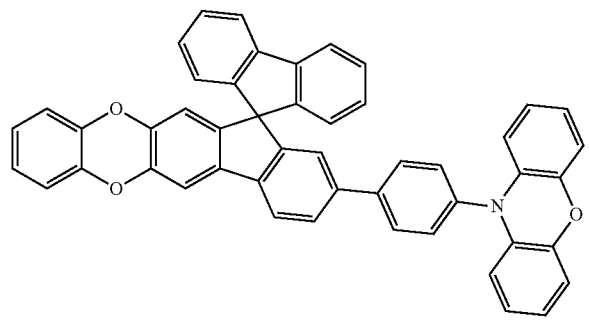
Cpd 65
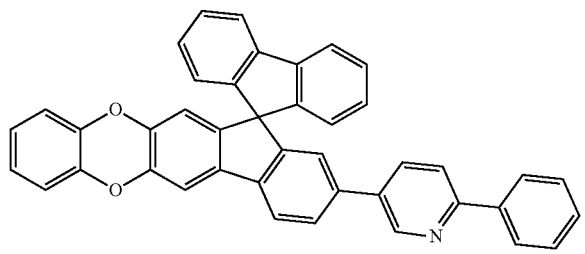
Cpd 66
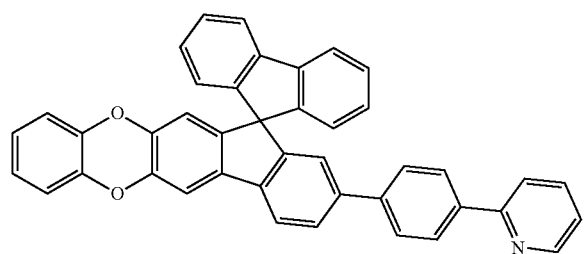
Cpd 67
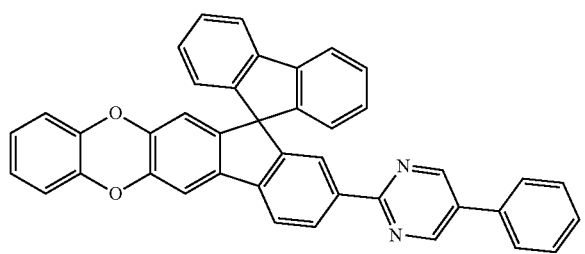
Cpd 68
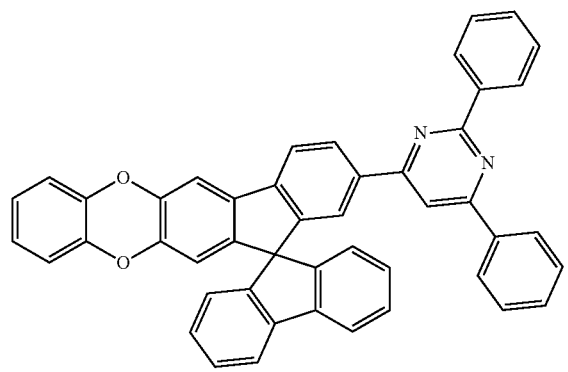
Cpd 69
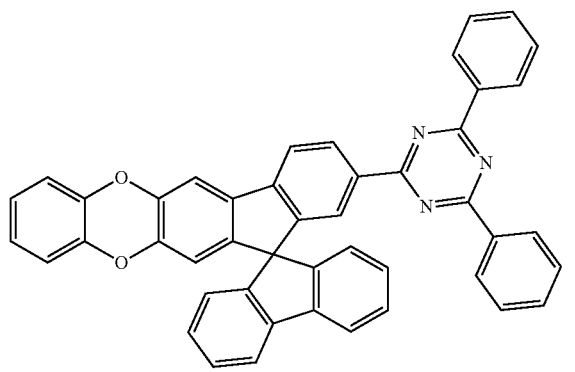

-continued
Cpd 70
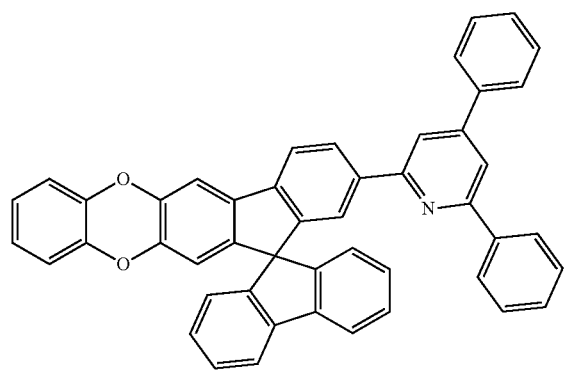
Cpd 71
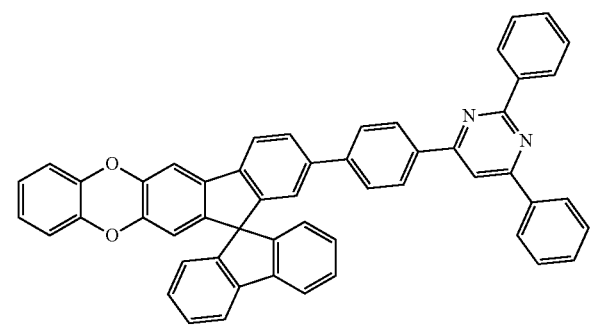
Cpd 72
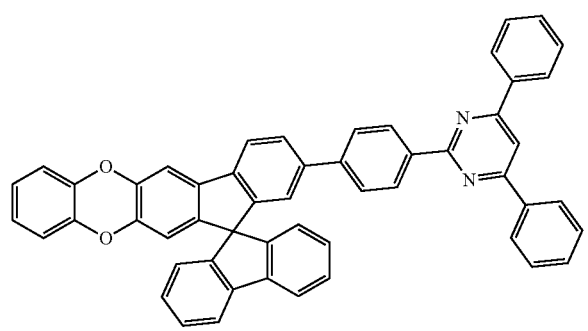
Cpd 73
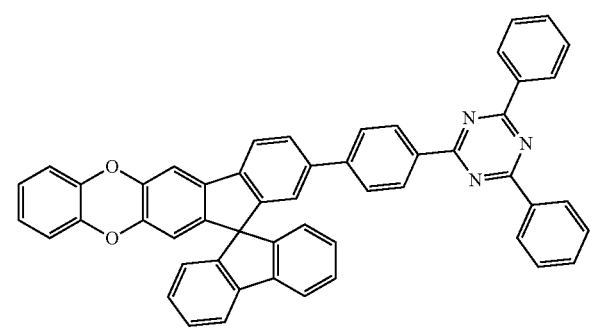
Cpd 74
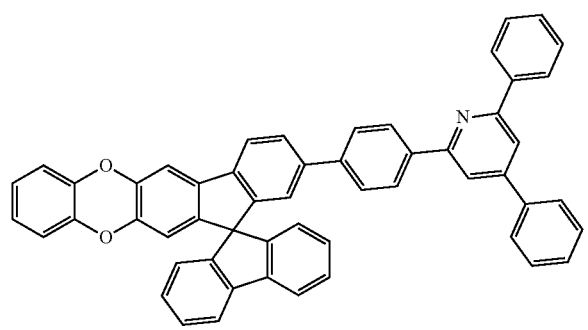
Cpd 75
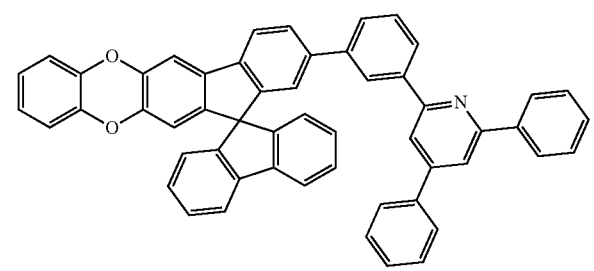
Cpd 76
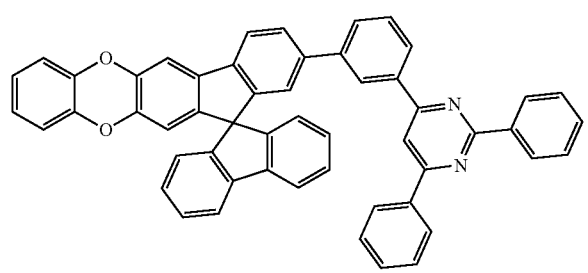
Cpd 77
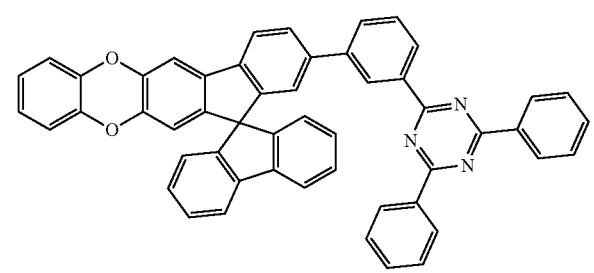

Cpd 78
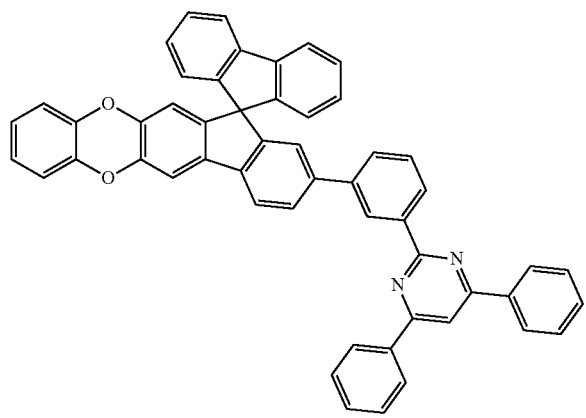
Cpd 79
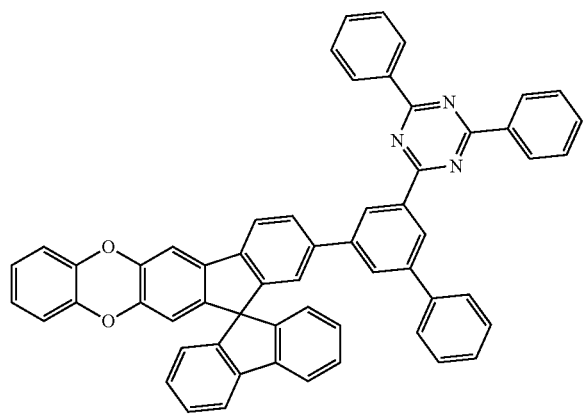
Cpd 80
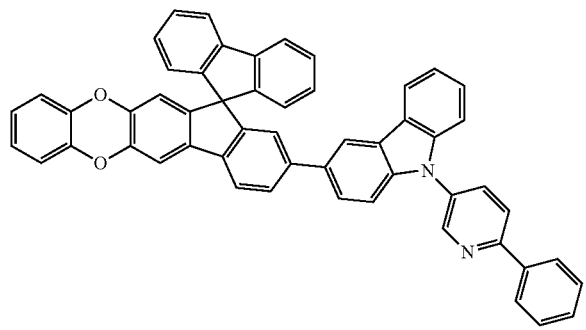
Cpd 81
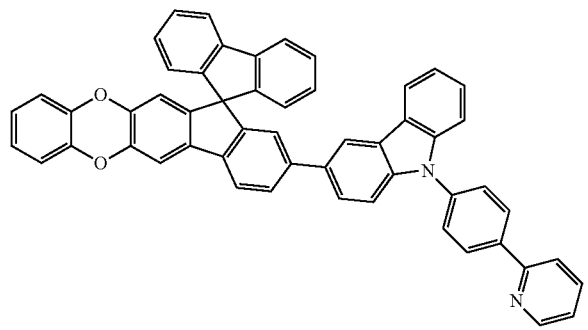
Cpd 82
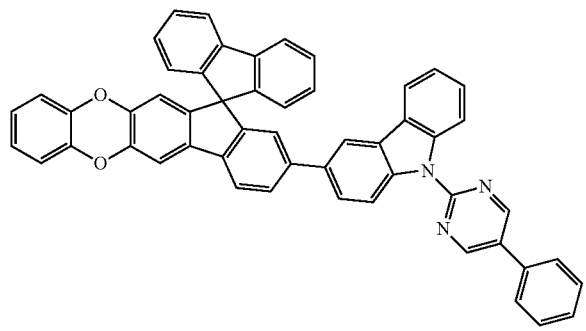
Cpd 83
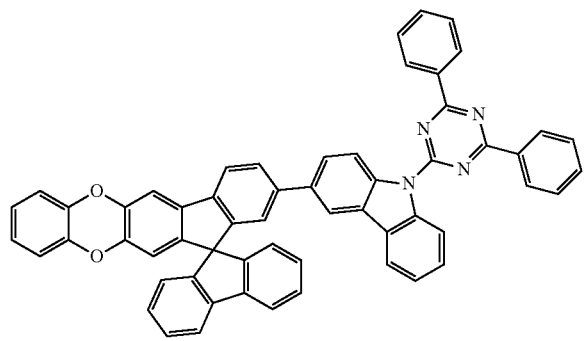
Cpd 84
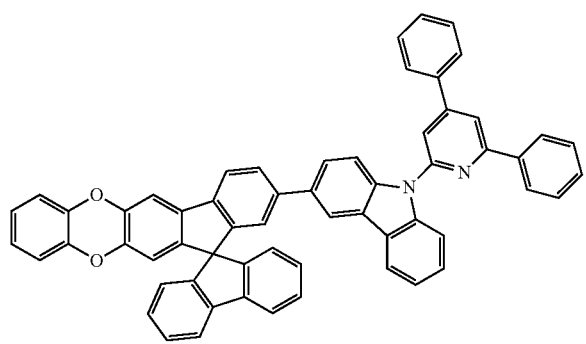
Cpd 85
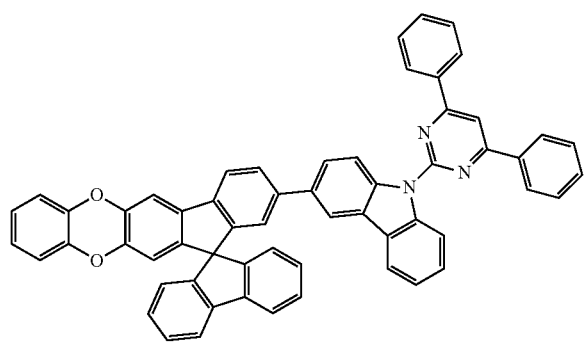

Cpd 86
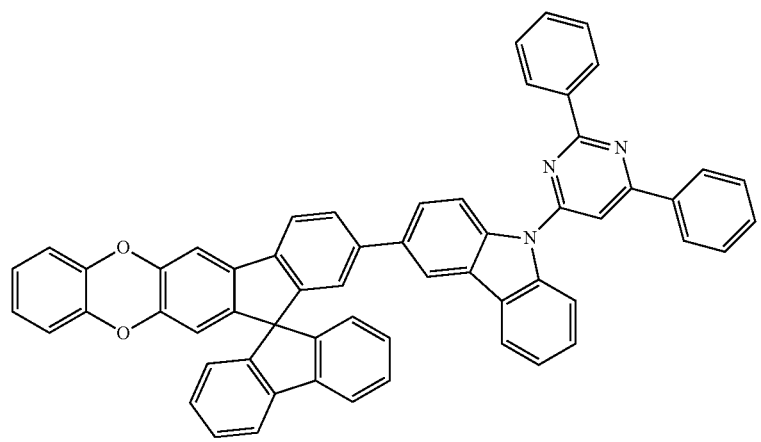
Cpd 87
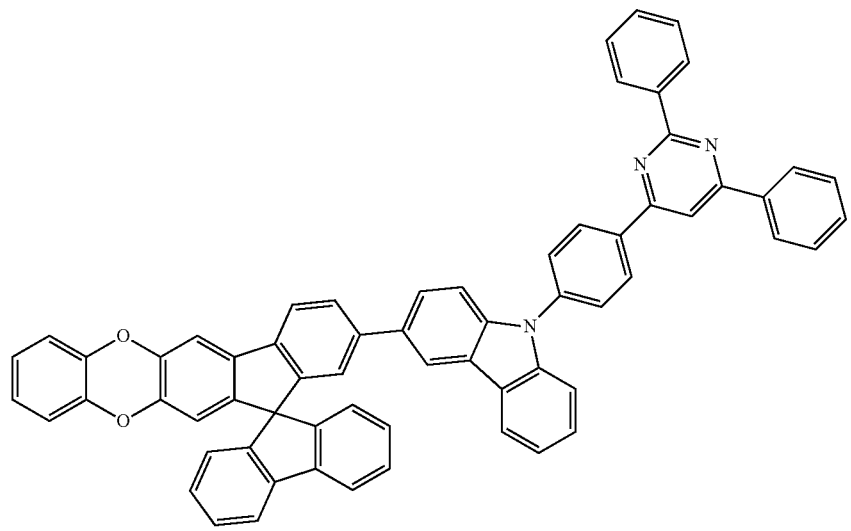
Cpd 88
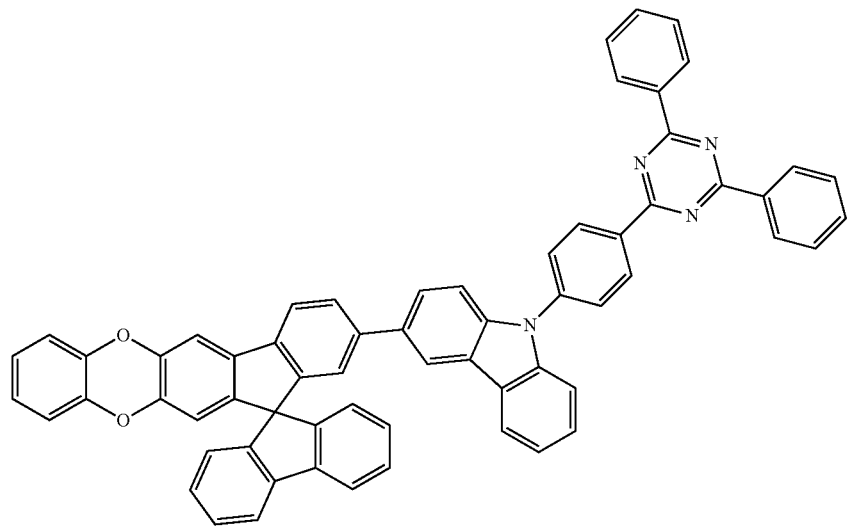

Cpd 89
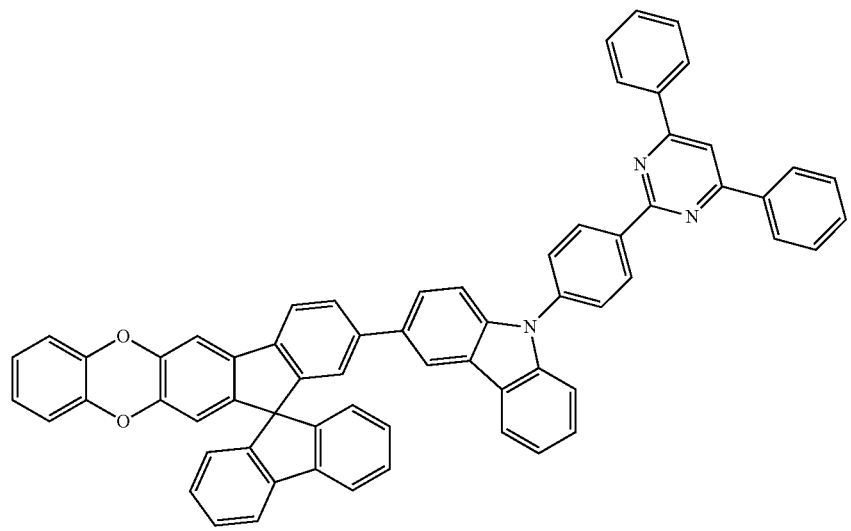
Cpd 90
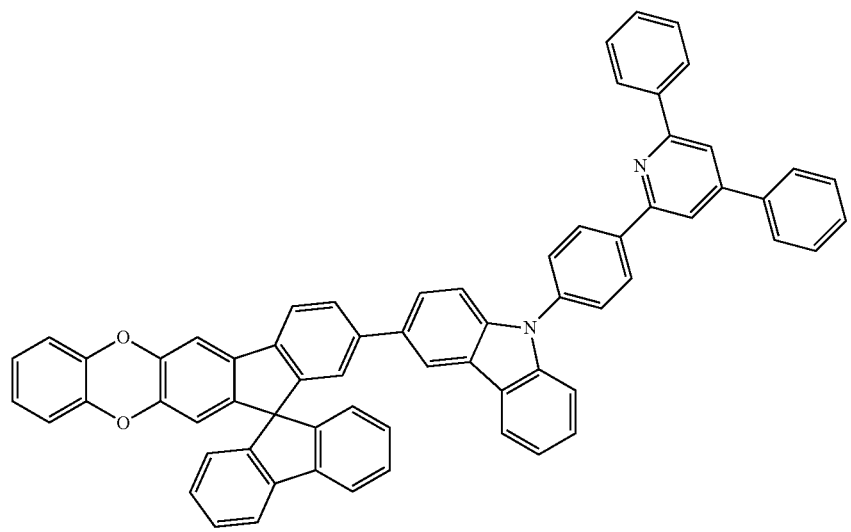
Cpd 91
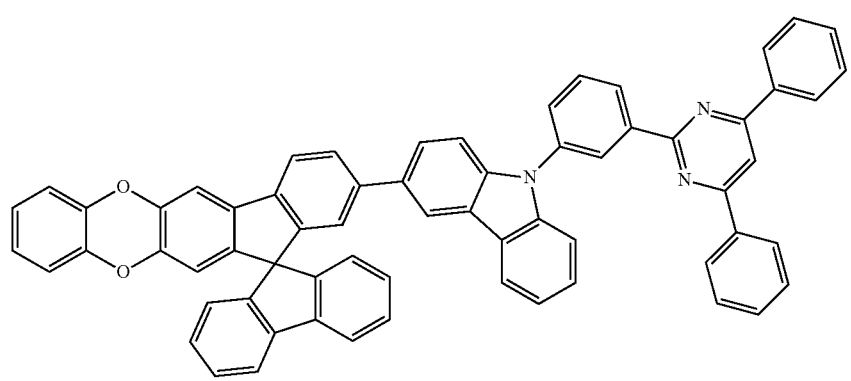

-continued
Cpd 92
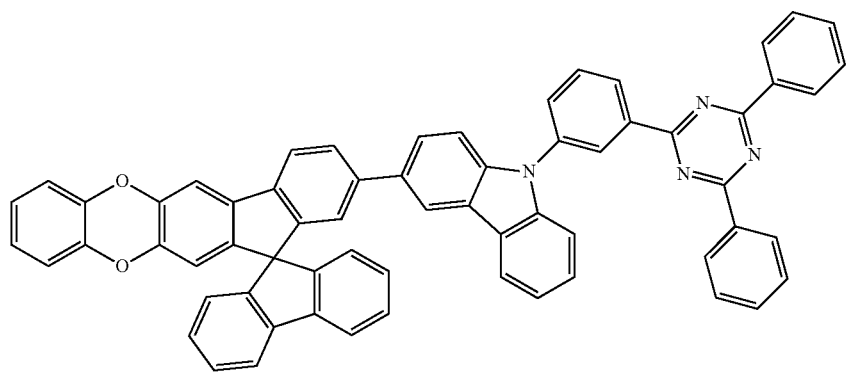
Cpd 93
Cpd 94

Cpd 95
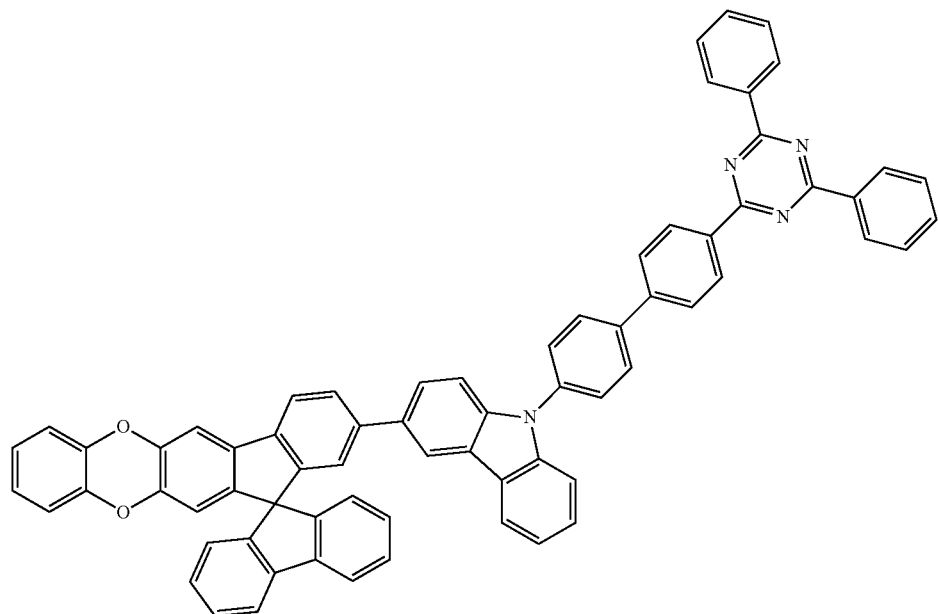
Cpd 96
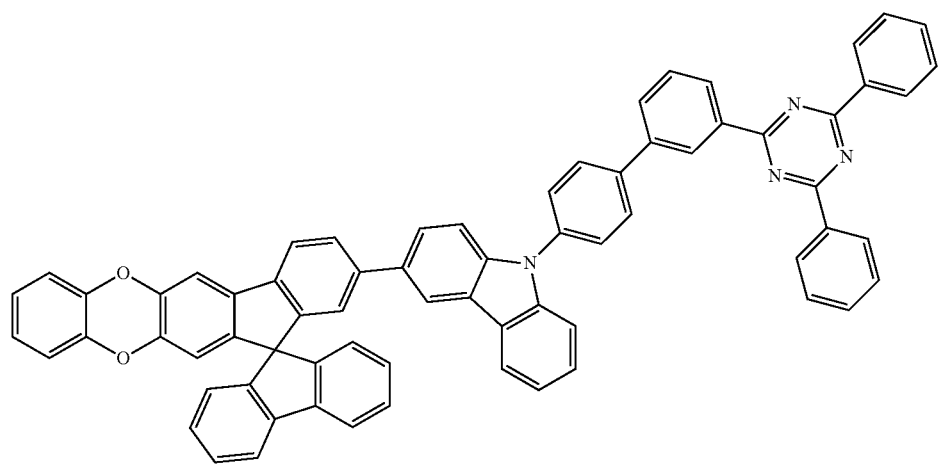
Cpd 97
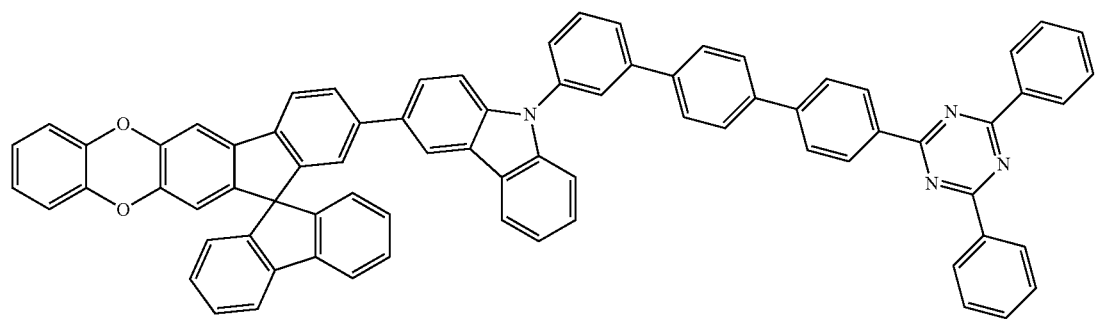

-continued
Cpd 98
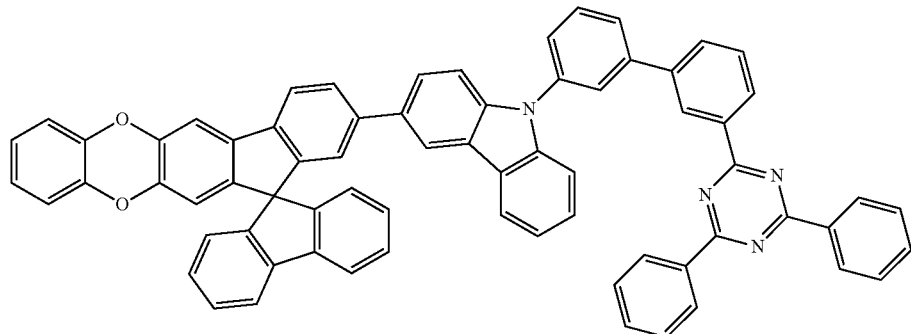
Cpd 99
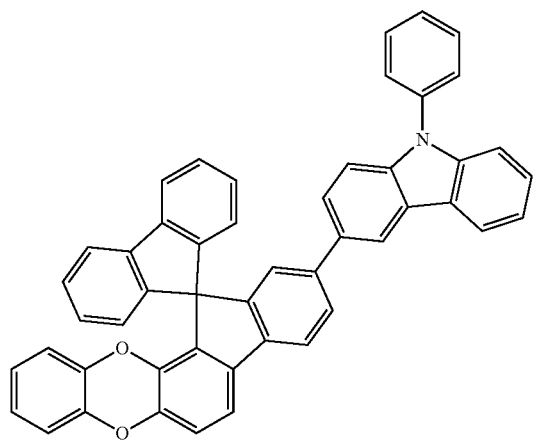
Cpd 100
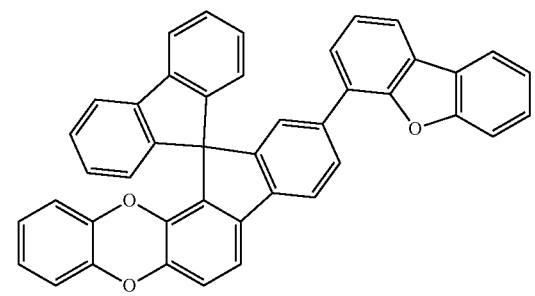
Cpd 101
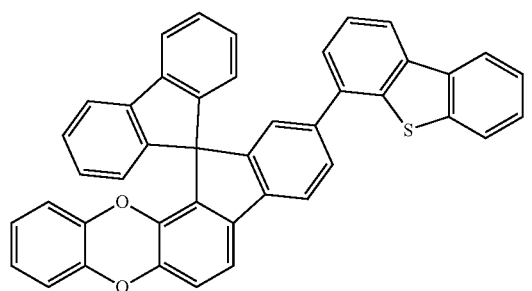
Cpd 102
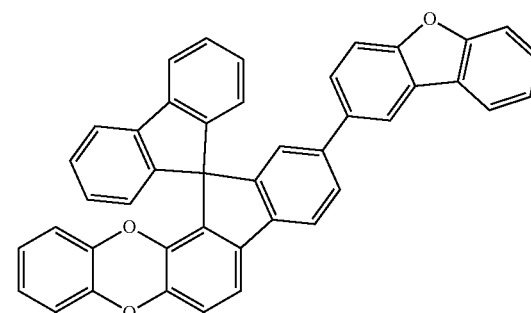
Cpd 103
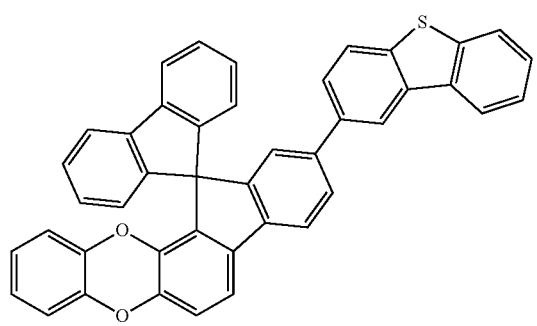
Cpd 104
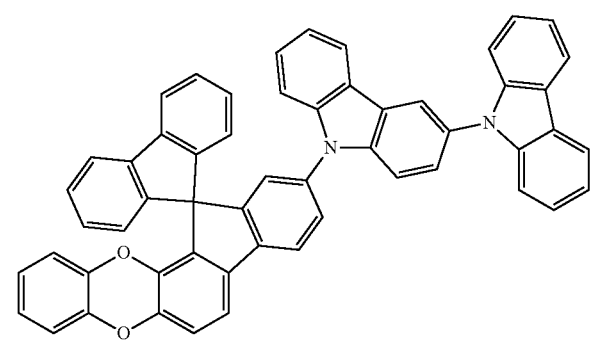

-continued
Cpd105
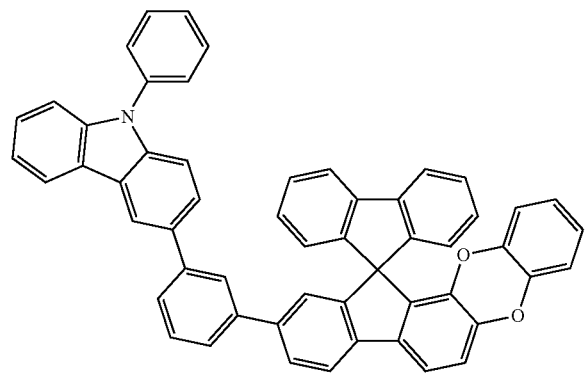
Cpd 106
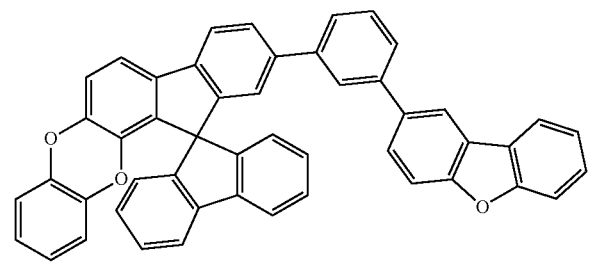
Cpd 107
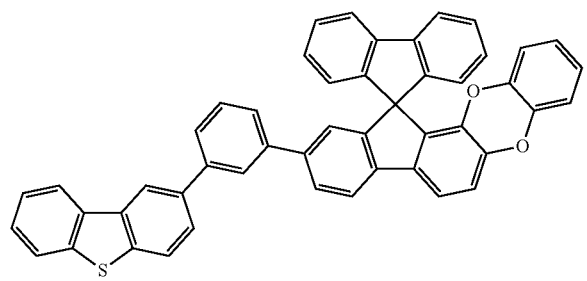
Cpd 108
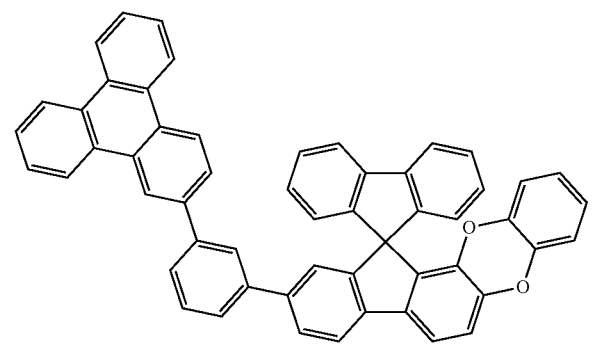
Cpd 109
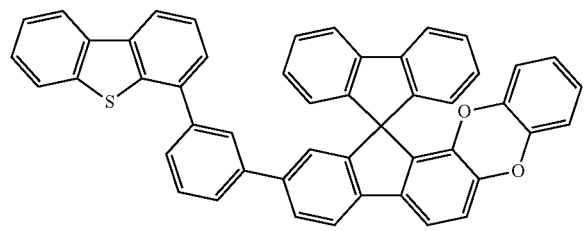
Cpd 110
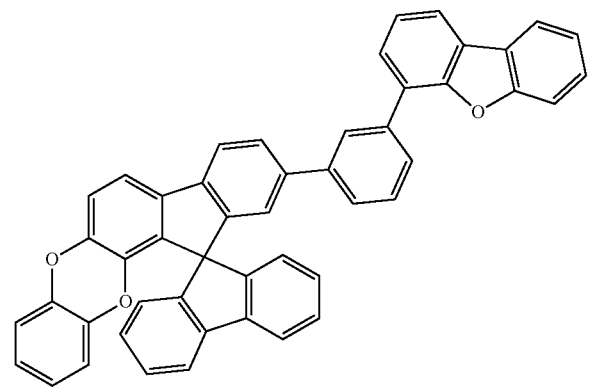

-continued
Cpd 111
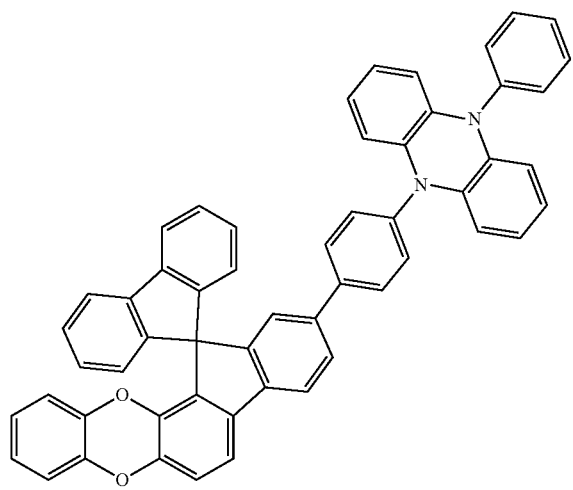
Cpd 112
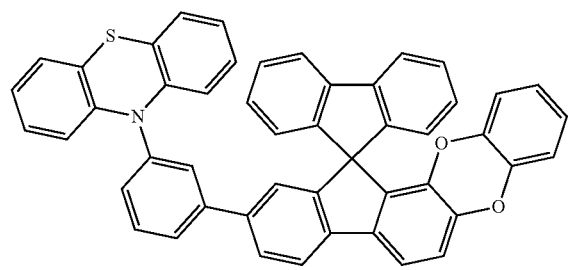
Cpd 113
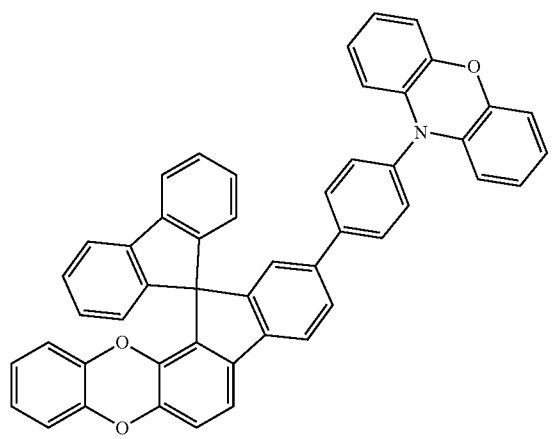
Cpd 114
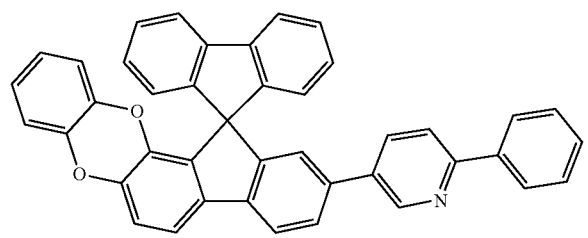
Cpd 115
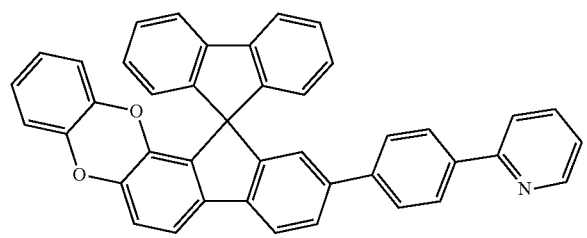
Cpd 116
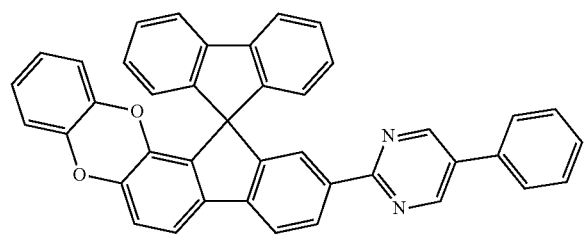
Cpd 117
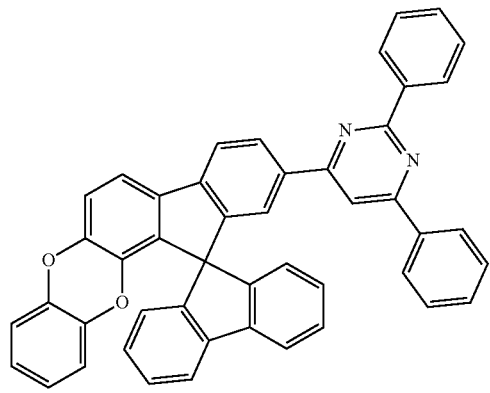
Cpd 118
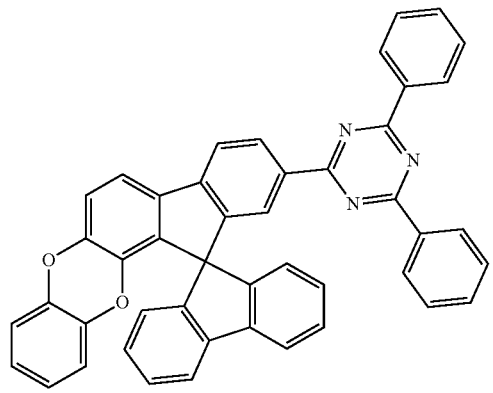

-continued
Cpd 119
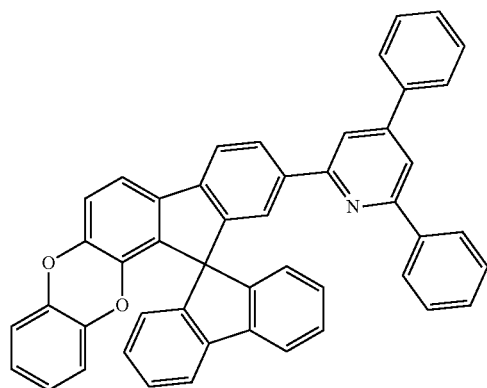
Cpd 120
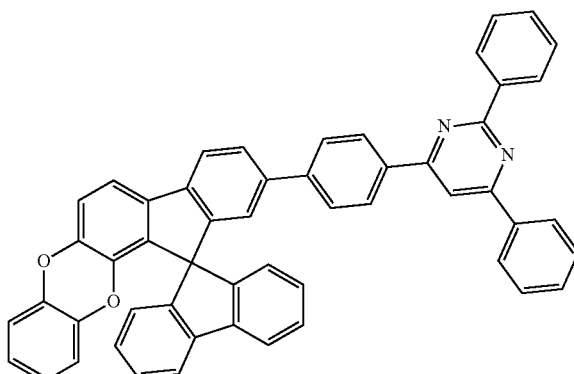
Cpd 121
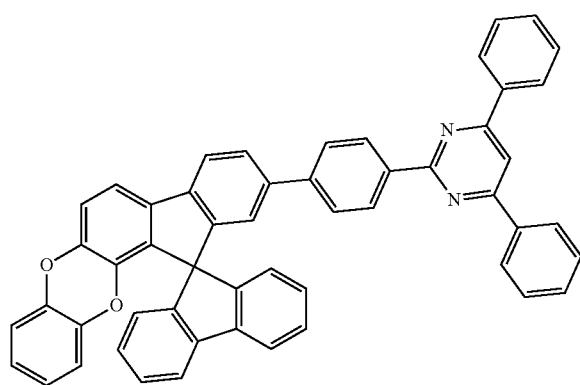
Cpd 122
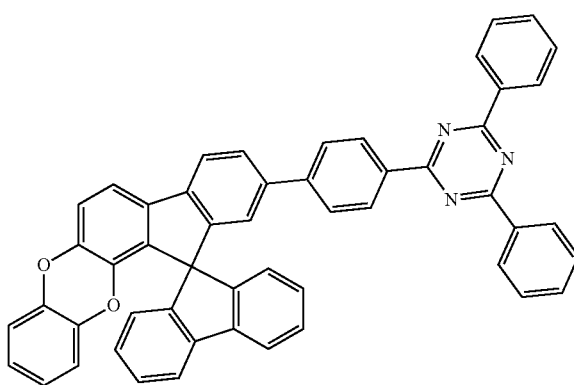
Cpd 123
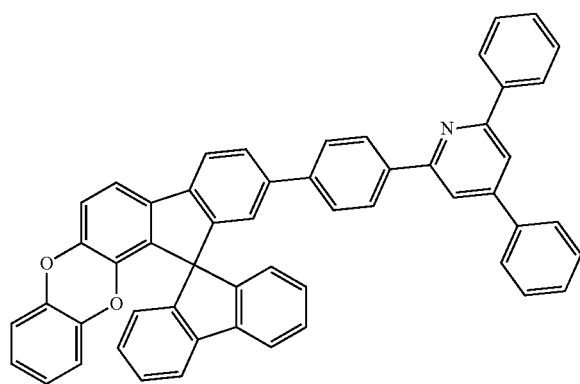
Cpd 124
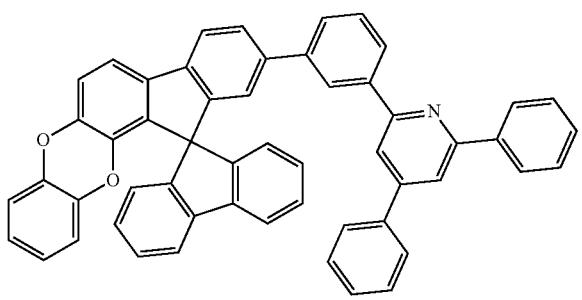
Cpd 125
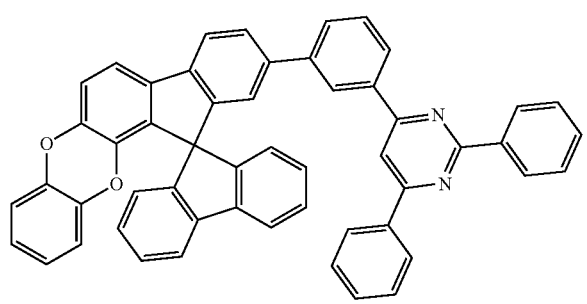
Cpd 126
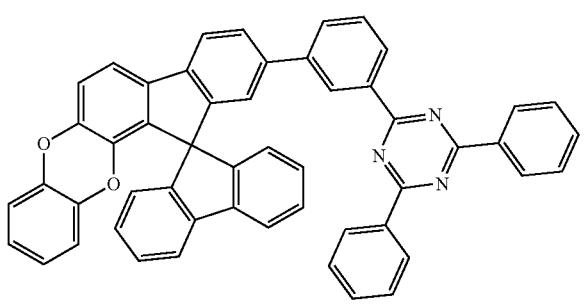

-continued
Cpd 127
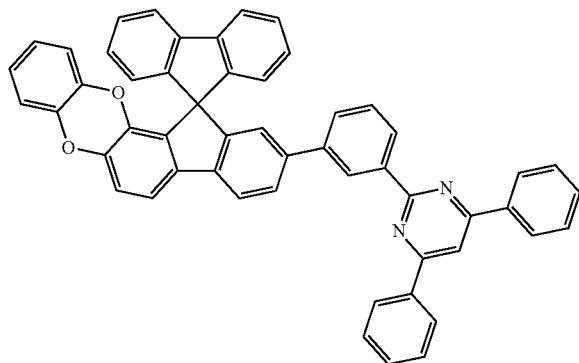
Cpd 128
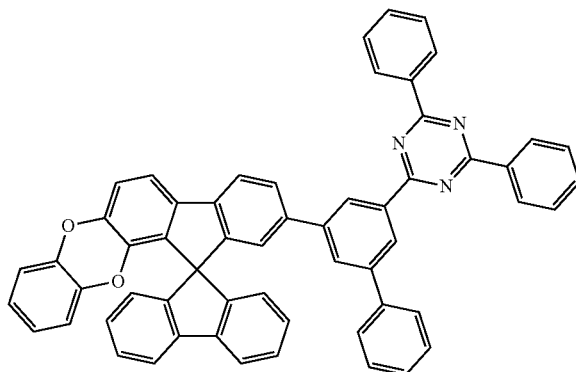
Cpd 129
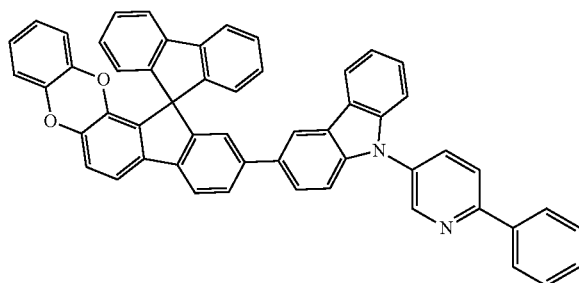
Cpd 130
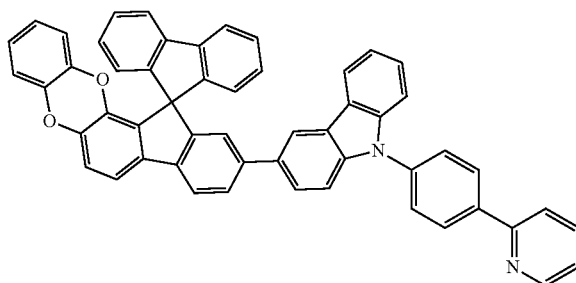
Cpd 131
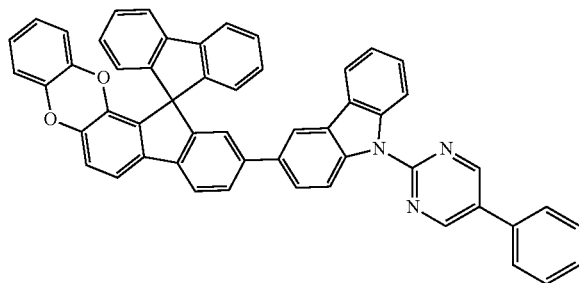
Cpd 132
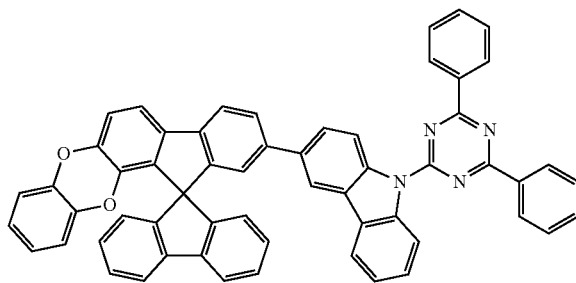
Cpd 133
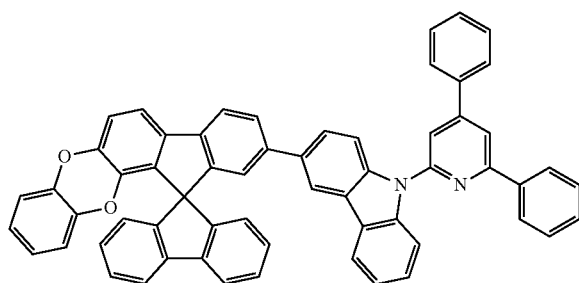
Cpd 134
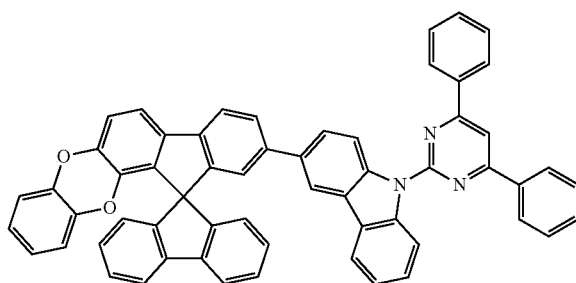

-continued
Cpd 135
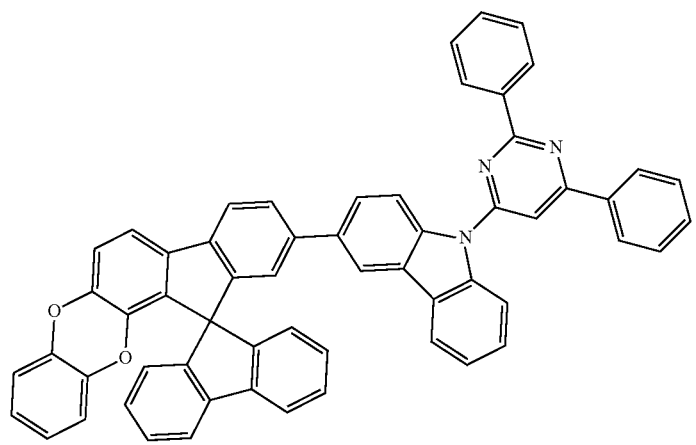
Cpd 136
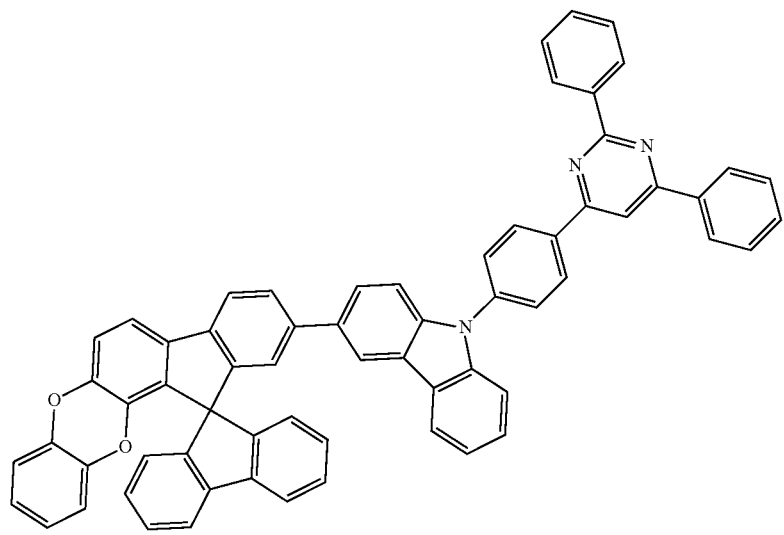
Cpd 137
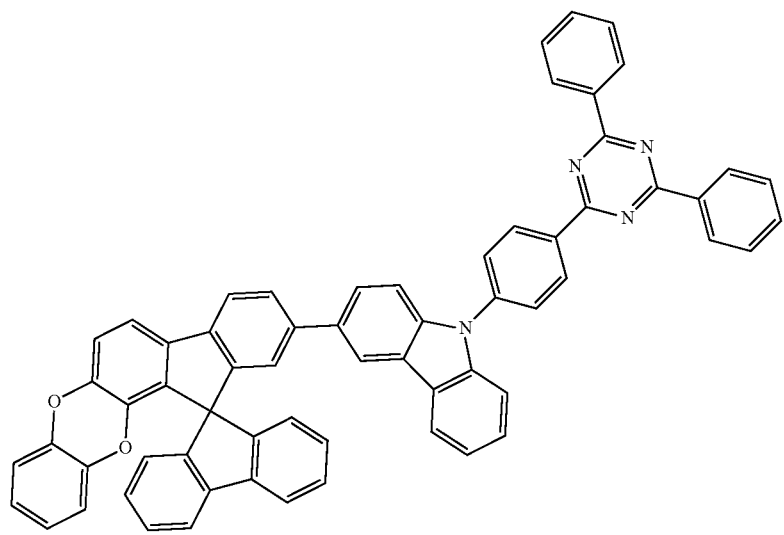

-continued
Cpd 138
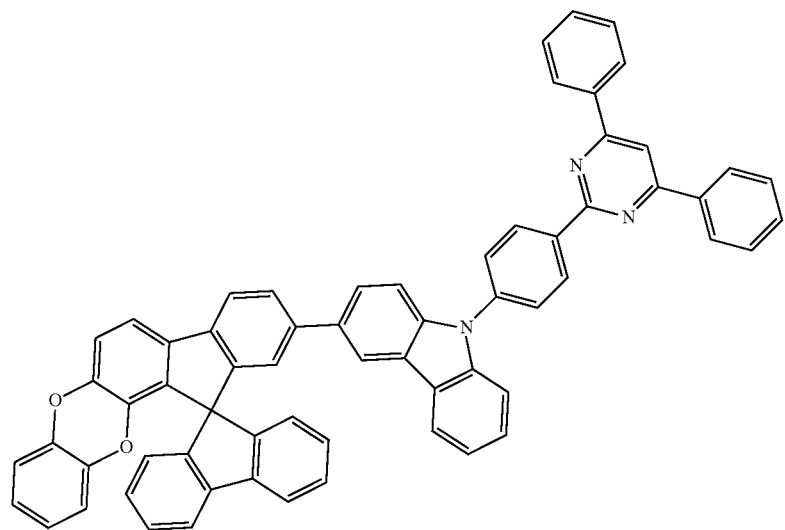
Cpd 139
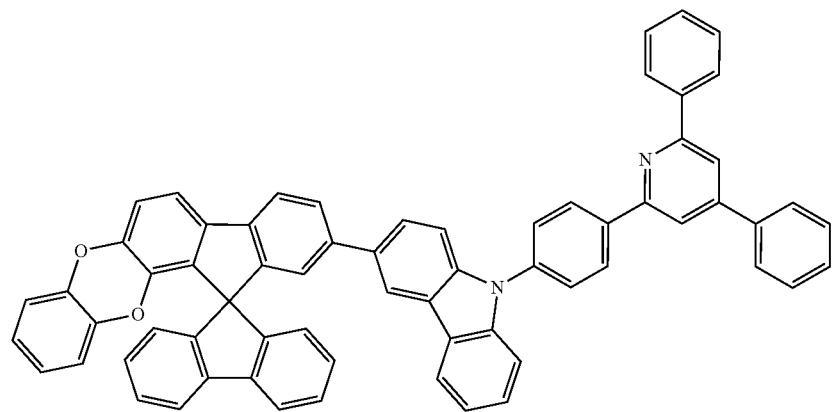
Cpd 140
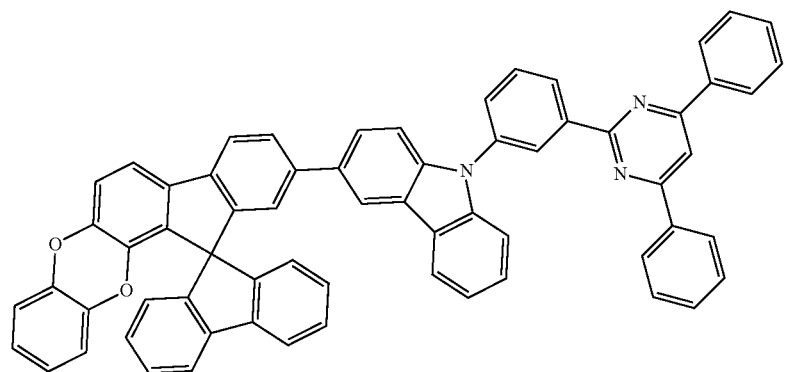

-continued
Cpd 141
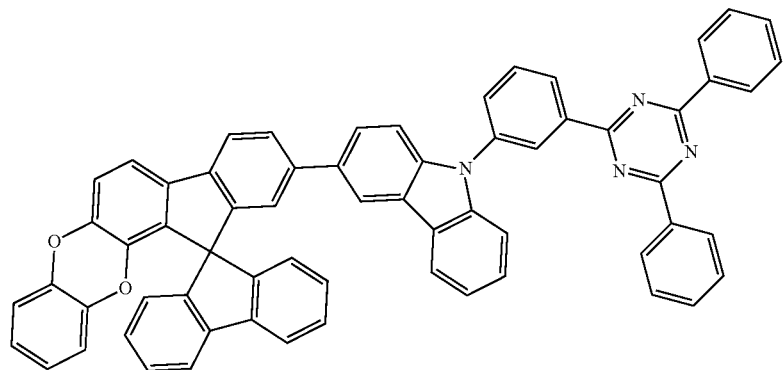
Cpd 142
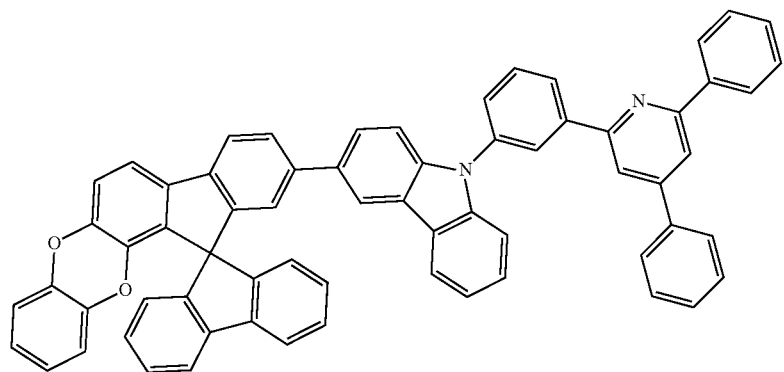
Cpd 143
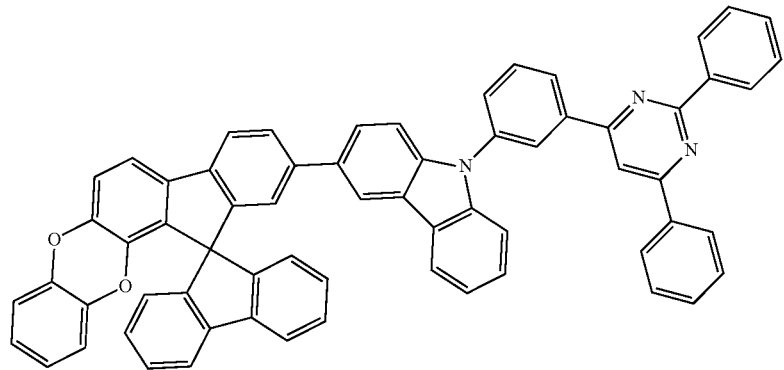
Cpd 144
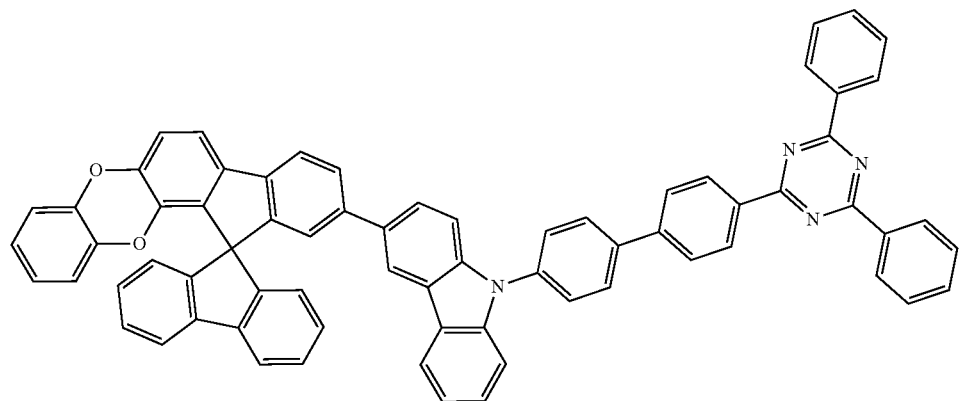

Cpd 145
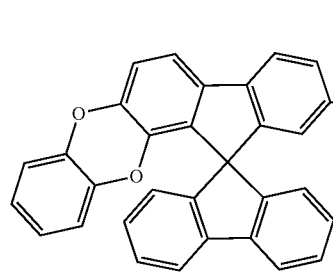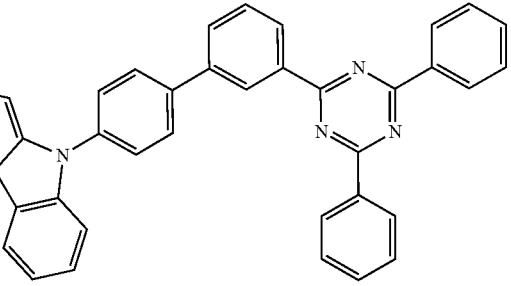
Cpd 146
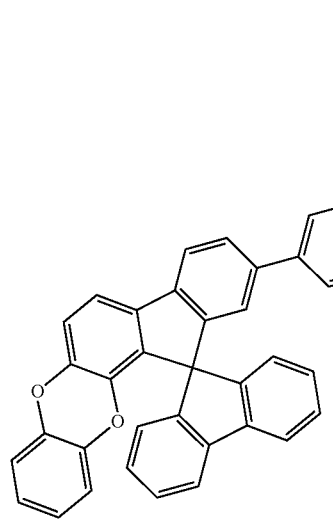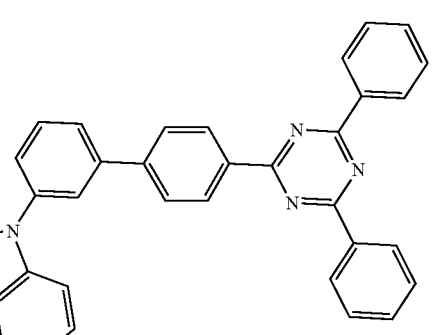
Cpd 147
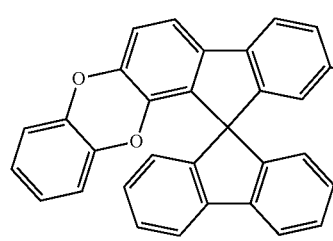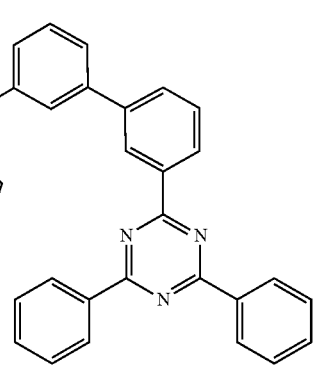
Cpd 148
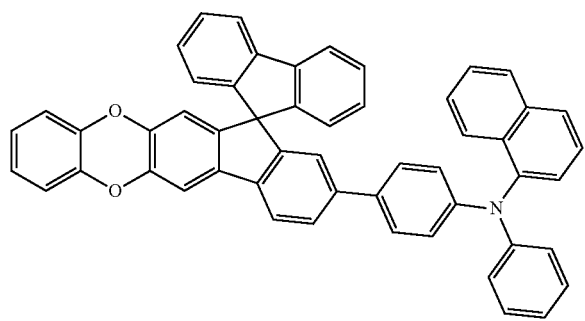
Cpd 149
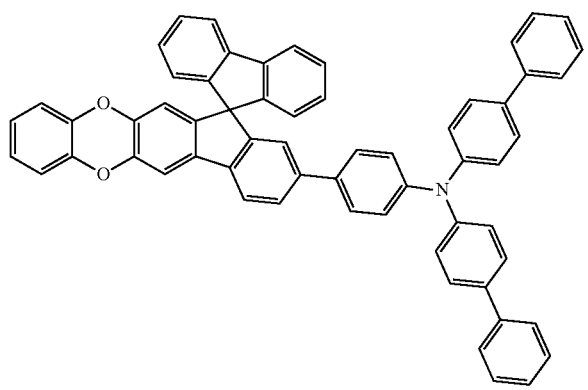

-continued
Cpd 150
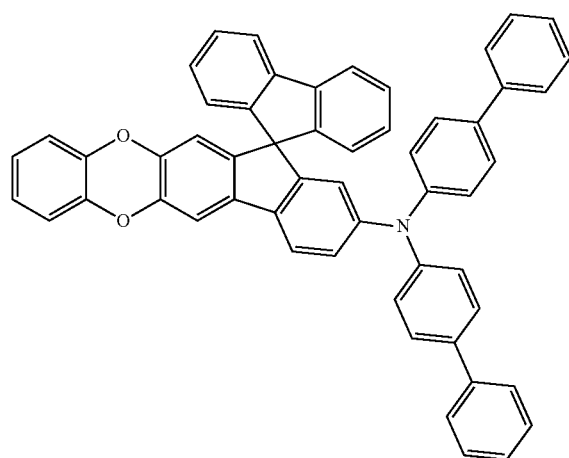
Cpd 151
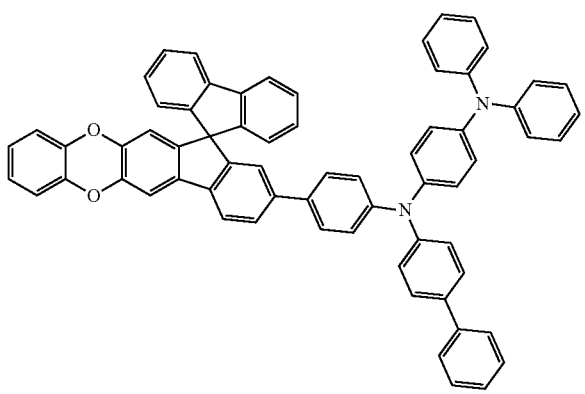
Cpd 152
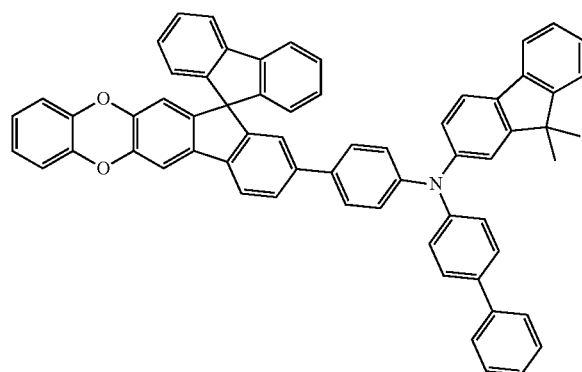
Cpd 153
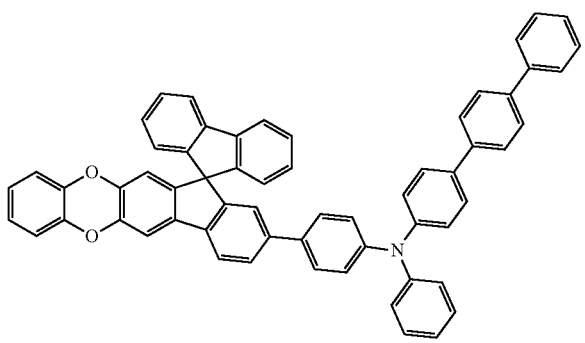
Cpd 154
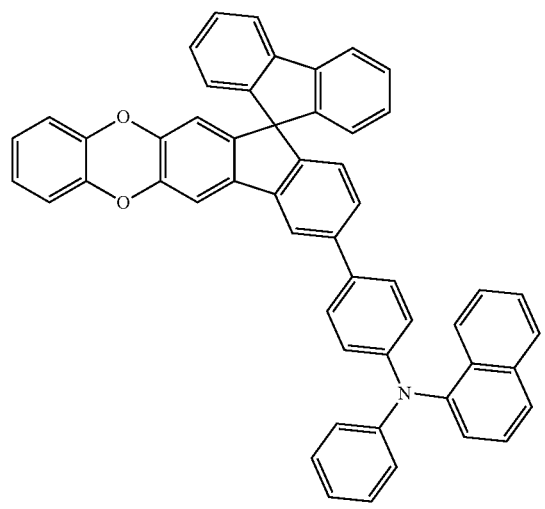
Cpd 155
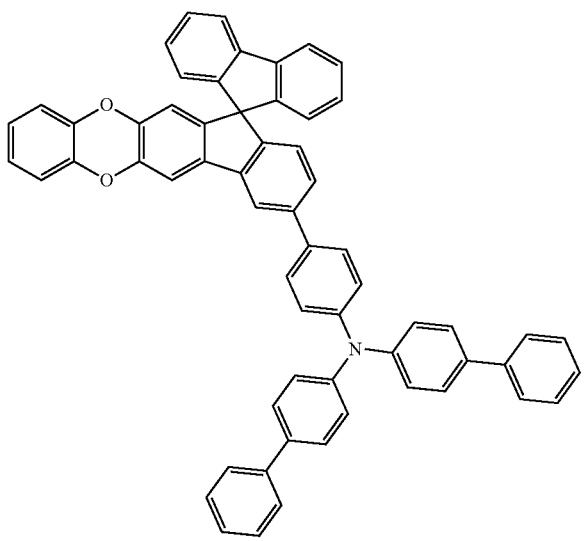

Cpd 157
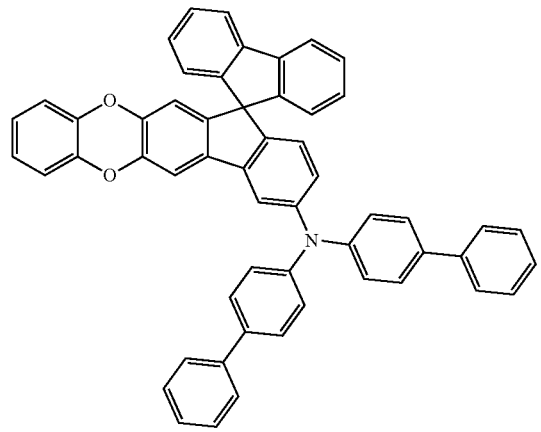
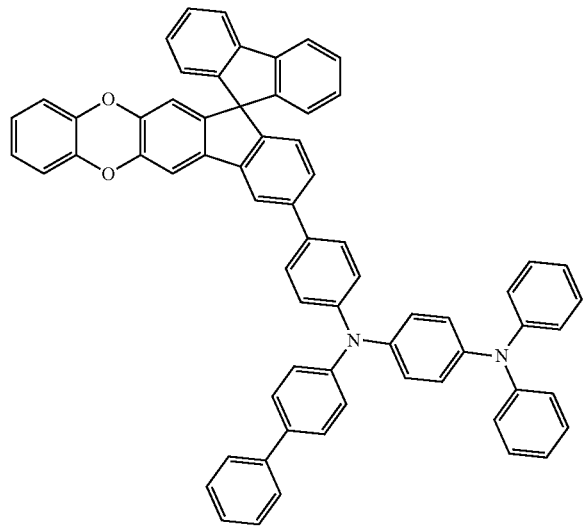
Cpd 158
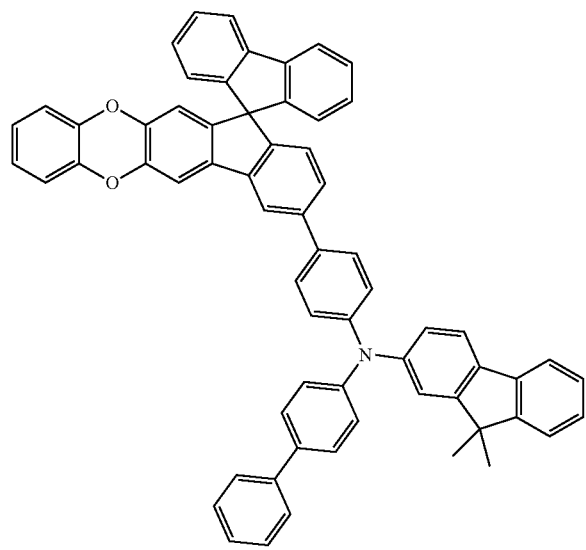
Cpd 159
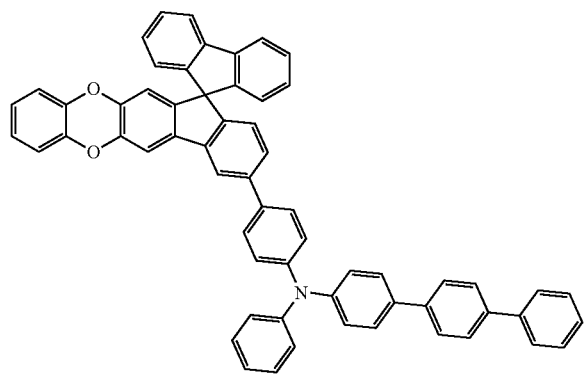

-continued
Cpd 160
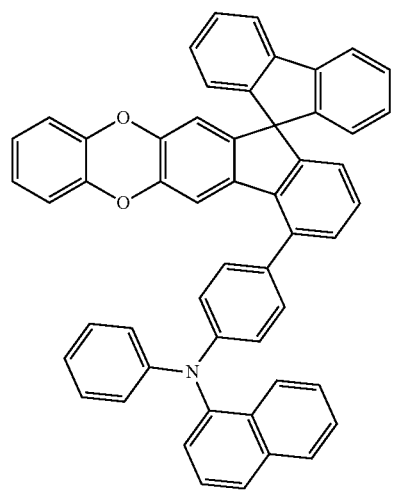
Cpd 161
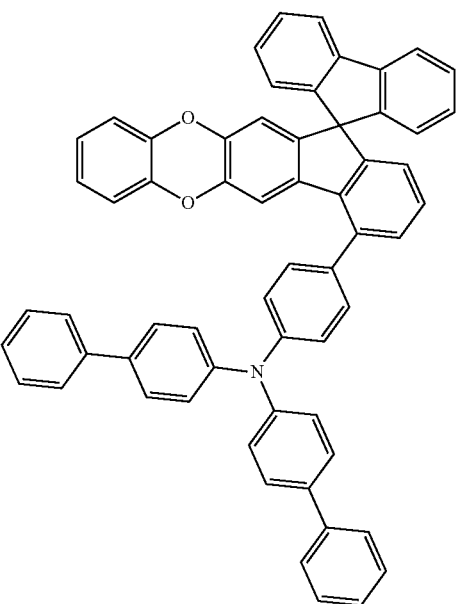
Cpd 162
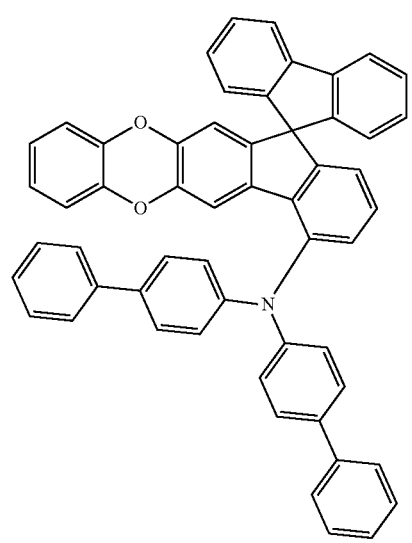
Cpd 163
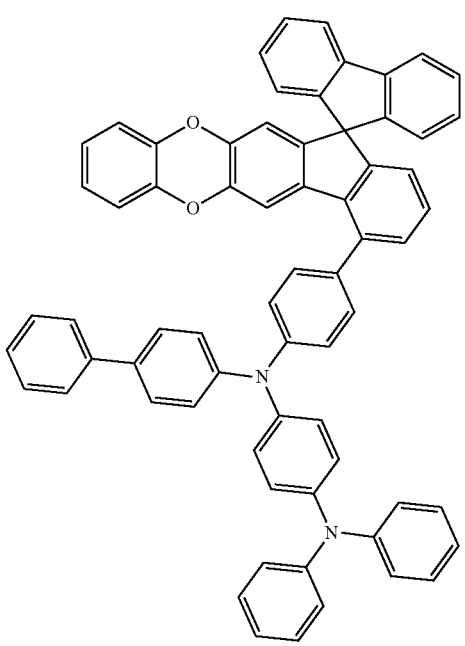

-continued
Cpd 164
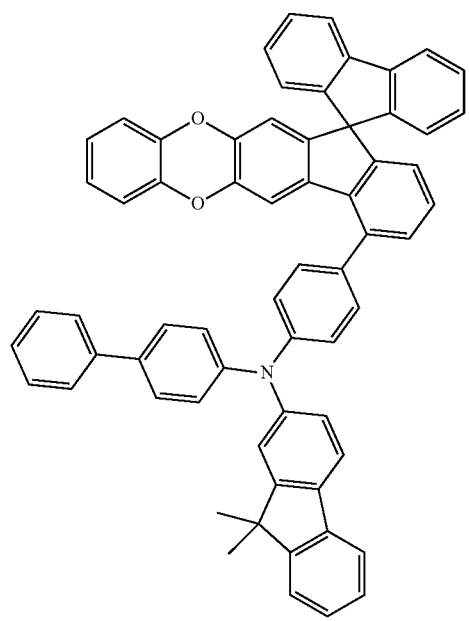
Cpd 165
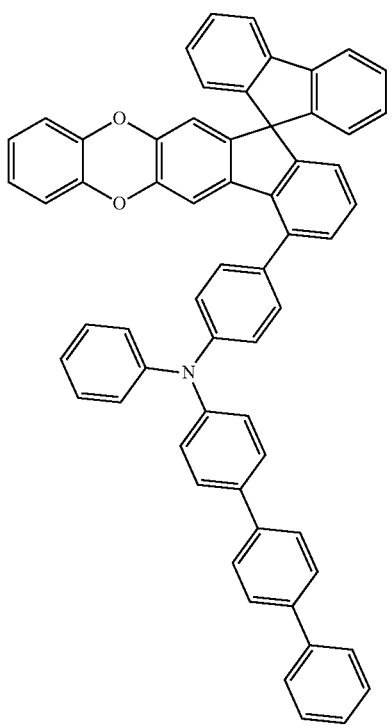
Cpd 166
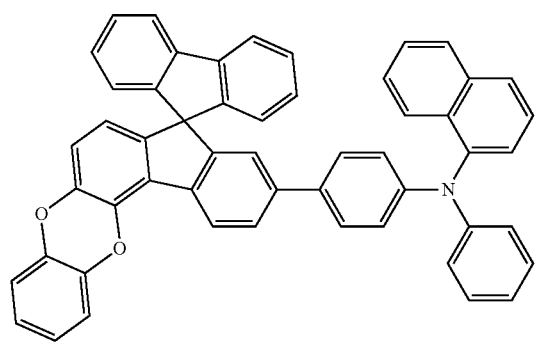
Cpd 167
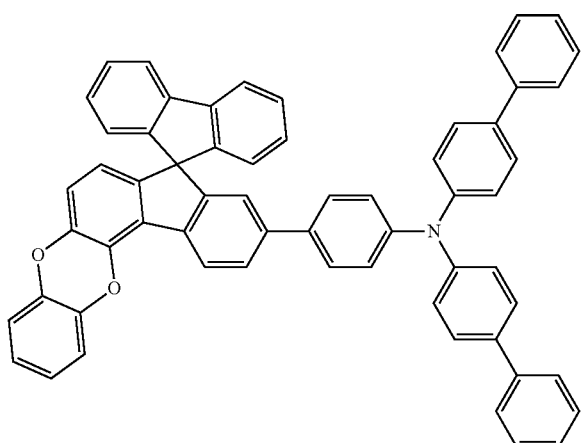
Cpd 168
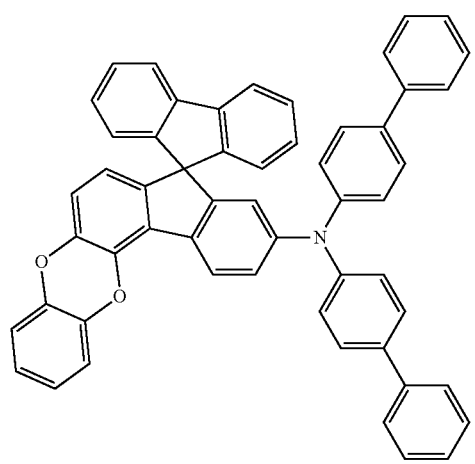
Cpd 169
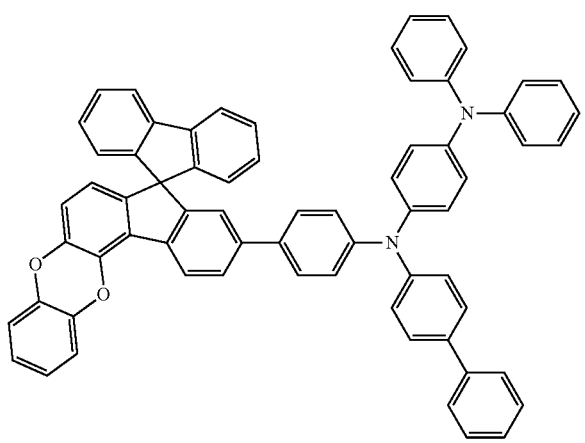

-continued
Cpd 170
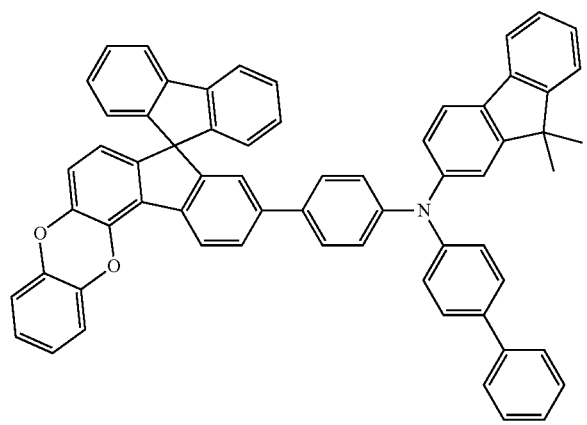
Cpd 171
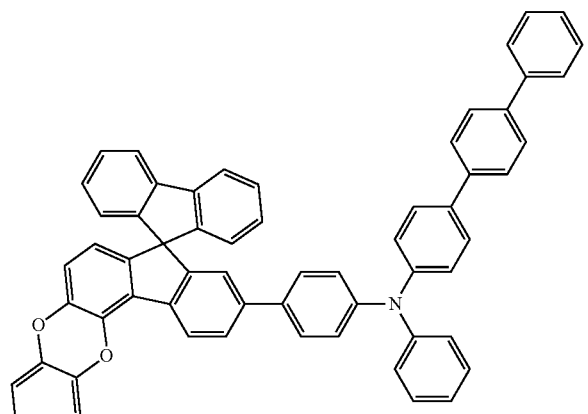
Cpd 172
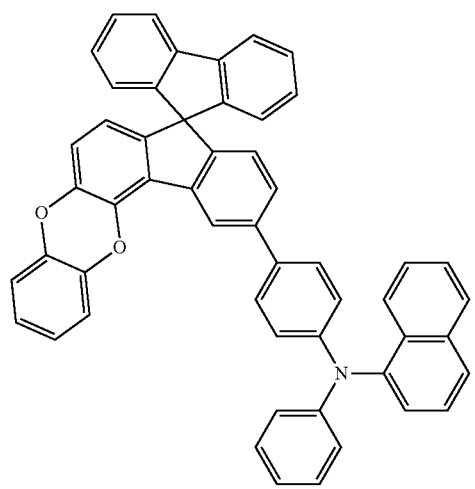
Cpd 173
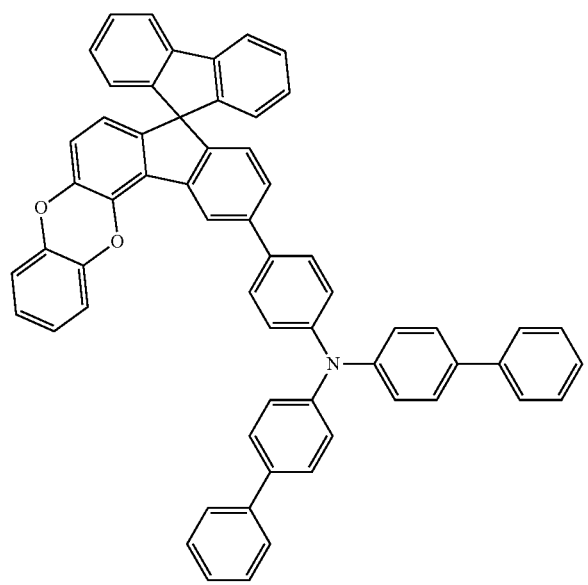
Cpd 174
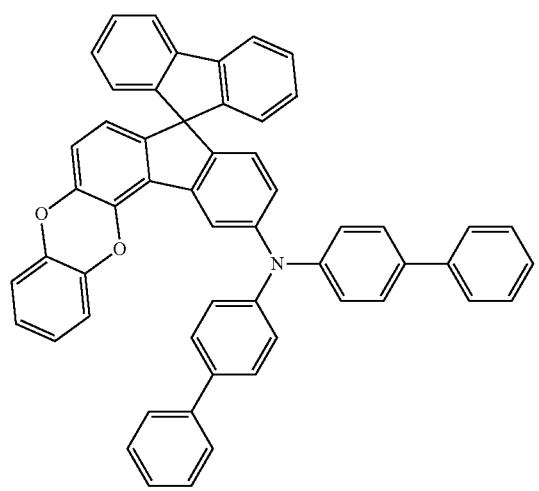
Cpd 175
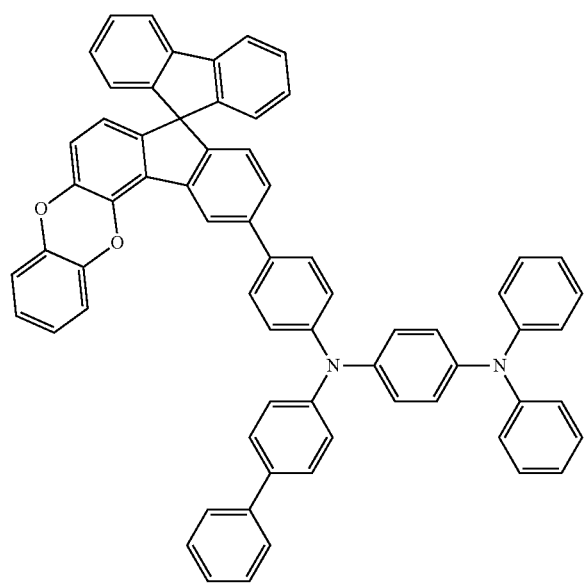

Cpd 176
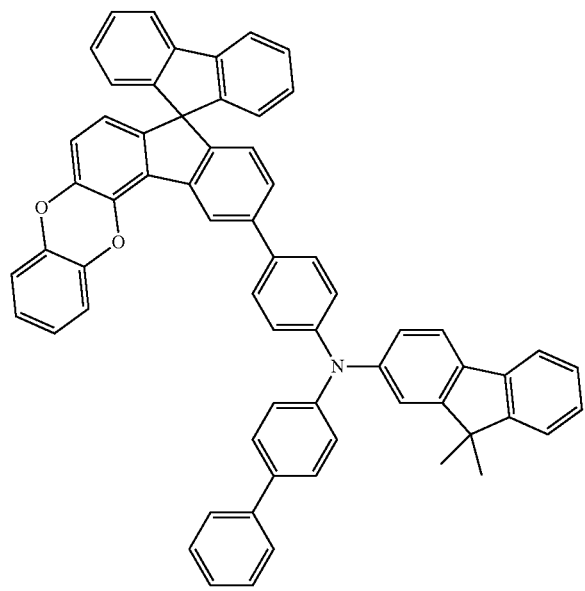
Cpd 177
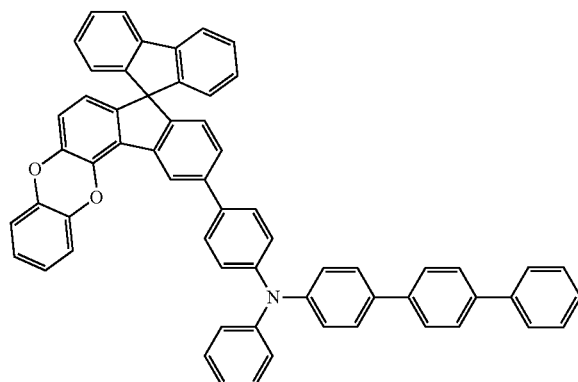
Cpd 178
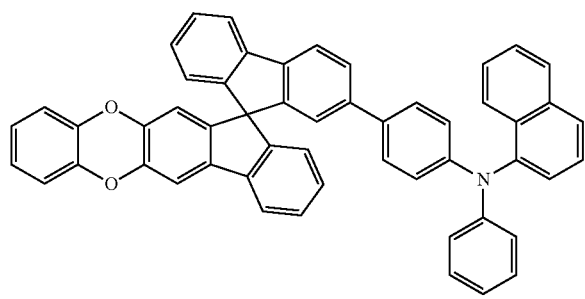
Cpd 179
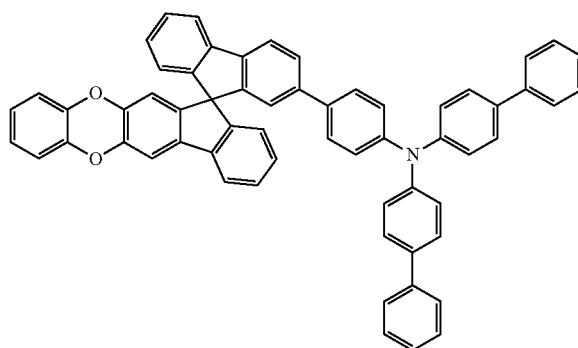
Cpd 180
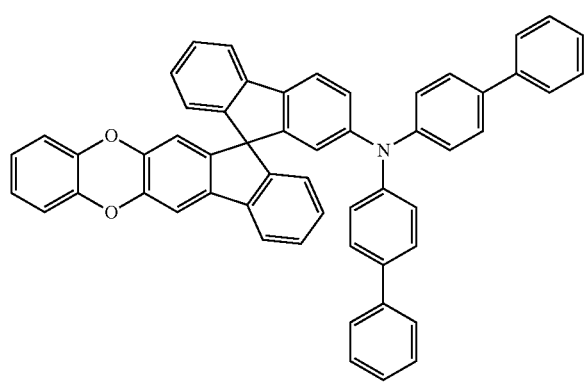

Cpd 181
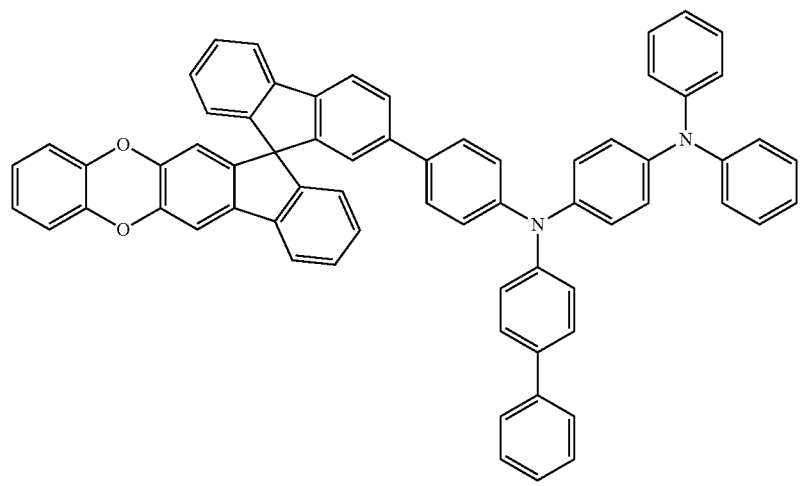
Cpd 182
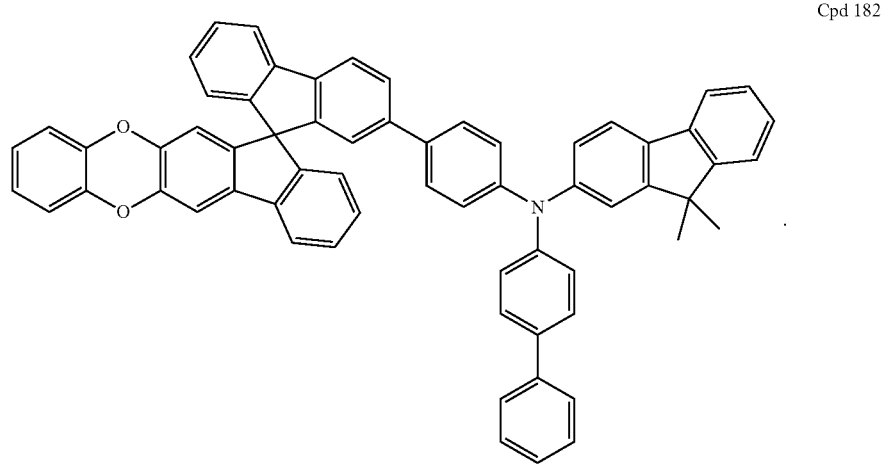
* * * * *